(12) United States Patent
Petersen et al.

(10) Patent No.: US 10,588,904 B2
(45) Date of Patent: *Mar. 17, 2020

(54) METAP2 INHIBITORS AND METHODS OF TREATING OBESITY

(71) Applicant: SynDevRx, Inc., Cambridge, MA (US)

(72) Inventors: John S. Petersen, Acton, MA (US); James Shanahan, Cambridge, MA (US)

(73) Assignee: SynDevRx, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/993,059

(22) Filed: May 30, 2018

(65) Prior Publication Data

US 2018/0271856 A1    Sep. 27, 2018

Related U.S. Application Data

(63) Continuation of application No. 15/665,755, filed on Aug. 1, 2017, now Pat. No. 10,010,544, which is a
(Continued)

(51) Int. Cl.
*A61K 31/77* (2006.01)
*A61K 31/485* (2006.01)
(Continued)

(52) U.S. Cl.
CPC .......... *A61K 31/485* (2013.01); *A61K 31/336* (2013.01); *A61K 31/77* (2013.01);
(Continued)

(58) Field of Classification Search
CPC . A61K 31/77; A61K 31/485; A61K 47/48338
(Continued)

(56) References Cited

U.S. PATENT DOCUMENTS 4,997,878 A    3/1991    Bock et al.
5,037,883 A    8/1991    Kopecek et al.
(Continued)

FOREIGN PATENT DOCUMENTS

CA    1305053    7/1992
EP    0673258 B1    5/2003
(Continued)

OTHER PUBLICATIONS

Chang, Worlld Journal of Biol.Chem. 2017, vol. 8(2), pp. 102-107. (Year: 2017).*
(Continued)

*Primary Examiner* — Craig D Ricci
*Assistant Examiner* — Janet L Coppins
(74) *Attorney, Agent, or Firm* — Cooley LLP; Ivor R. Elrifi; Matthew Pavao

(57) ABSTRACT

The present invention relates to modified or polymer conjugated MetAP2 inhibitors. The present invention also relates to methods of preventing, inducing, causing or increasing weight loss, treating obesity and/or treating metabolic syndrome utilizing the modified or polymer conjugated MetAP2 inhibitors. The present invention also relates to methods of improving insulin sensitivity and glycemic control, reducing insulin levels and/or improving leptin sensitivity utilizing the modified or polymer conjugated MetAP2 inhibitors.

47 Claims, 25 Drawing Sheets

Related U.S. Application Data continuation of application No. 15/226,258, filed on Aug. 2, 2016, now Pat. No. 9,750,737, which is a continuation of application No. 14/851,668, filed on Sep. 11, 2015, now Pat. No. 9,433,600, which is a continuation of application No. 14/248,787, filed on Apr. 9, 2014, now Pat. No. 9,173,956.

(60) Provisional application No. 61/810,468, filed on Apr. 10, 2013, provisional application No. 61/925,918, filed on Jan. 10, 2014.

(51) Int. Cl.

| | | |
|---|---|---|
| *A61K 47/65* | (2017.01) | |
| *A61K 47/54* | (2017.01) | |
| *A61K 47/58* | (2017.01) | |
| *A61P 3/10* | (2006.01) | |
| *A61P 3/04* | (2006.01) | |
| *A61P 3/08* | (2006.01) | |
| *A61P 5/50* | (2006.01) | |
| *A61K 31/336* | (2006.01) | |

(52) U.S. Cl.
CPC ............ *A61K 47/542* (2017.08); *A61K 47/58* (2017.08); *A61K 47/65* (2017.08); *A61P 3/04* (2018.01); *A61P 3/08* (2018.01); *A61P 3/10* (2018.01); *A61P 5/50* (2018.01)

(58) Field of Classification Search
USPC .......................................................... 514/475
See application file for complete search history.

(56) References Cited

U.S. PATENT DOCUMENTS

| | | | |
|---|---|---|---|
| 5,037,957 A | 8/1991 | Grubb et al. | |
| 5,166,172 A | 11/1992 | Kishimoto et al. | |
| 5,258,453 A | 11/1993 | Kopecek et al. | |
| 5,773,522 A | 6/1998 | Angelucci et al. | |
| 6,063,812 A | 5/2000 | Hong et al. | |
| 6,291,671 B1 | 9/2001 | Inoue et al. | |
| 6,306,819 B1 | 10/2001 | Rubnick et al. | |
| 6,436,912 B1 | 8/2002 | Inoue et al. | |
| 6,464,850 B1 | 10/2002 | Zhang et al. | |
| 6,548,477 B1 | 4/2003 | Olson et al. | |
| 6,759,509 B1 | 7/2004 | King et al. | |
| 6,803,438 B1 | 10/2004 | Brocchini et al. | |
| 6,811,788 B2 | 11/2004 | Yu | |
| 6,811,996 B1 | 11/2004 | Inoue et al. | |
| 6,835,807 B1 | 12/2004 | Susaki et al. | |
| 6,949,584 B2 | 9/2005 | Folkman et al. | |
| 7,041,818 B2 | 5/2006 | Susaki et al. | |
| 7,091,186 B2 | 8/2006 | Senter et al. | |
| 7,223,837 B2 | 5/2007 | De Groot et al. | |
| 7,332,523 B2 | 2/2008 | Folkman et al. | |
| 7,553,816 B2 | 6/2009 | Senter et al. | |
| 7,700,280 B2 | 4/2010 | Al-Murrani | |
| 7,943,569 B2 | 5/2011 | Gemeinhart et al. | |
| 8,349,891 B2 | 1/2013 | Crawford et al. | |
| 8,367,721 B2 | 2/2013 | Hughes et al. | |
| 8,399,512 B2 | 3/2013 | Akullian et al. | |
| 9,173,956 B2 * | 11/2015 | Petersen | A61K 31/485 |
| 9,320,805 B2 | 4/2016 | Petersen | |
| 9,433,600 B2 | 9/2016 | Petersen | |
| 9,585,909 B2 | 3/2017 | Petersen | |
| 9,730,955 B2 | 8/2017 | Petersen | |
| 9,750,737 B2 | 9/2017 | Petersen | |
| 9,757,373 B2 * | 9/2017 | Petersen | A61K 31/336 |
| 9,969,722 B2 | 5/2018 | Petersen et al. | |
| 10,010,544 B2 * | 7/2018 | Petersen | A61K 31/336 |
| 10,159,692 B2 | 12/2018 | Petersen et al. | |
| 2002/0076442 A1 | 6/2002 | Burke et al. | |
| 2004/0001801 A1 | 1/2004 | Madison et al. | |
| 2004/0116348 A1 | 6/2004 | Chau et al. | |
| 2004/0229945 A1 | 11/2004 | Satchi-Fainaro et al. | |
| 2005/0036948 A1 | 2/2005 | Kasina et al. | |
| 2006/0206948 A1 | 9/2006 | Zhao | |
| 2006/0276512 A1 | 12/2006 | Han et al. | |
| 2007/0142302 A1 | 6/2007 | Mitra et al. | |
| 2007/0287680 A1 | 12/2007 | Cuchelkar et al. | |
| 2008/0112919 A1 | 5/2008 | Satchi-Fainaro et al. | |
| 2008/0248030 A1 | 10/2008 | Folkman et al. | |
| 2009/0093014 A1 | 4/2009 | Burnet et al. | |
| 2010/0111894 A1 | 5/2010 | Benny-Ratsaby et al. | |
| 2011/0263561 A1 | 10/2011 | Heinrich et al. | |
| 2011/0294952 A1 | 12/2011 | Petersen | |
| 2013/0064832 A1 | 3/2013 | Aikawa et al. | |
| 2013/0137831 A1 | 5/2013 | Petersen | |
| 2013/0216494 A1 | 8/2013 | Petersen | |
| 2014/0308235 A1 | 10/2014 | Petersen | |
| 2015/0141580 A1 | 5/2015 | Petersen et al. | |
| 2015/0374657 A1 | 12/2015 | Petersen | |
| 2016/0184345 A1 | 6/2016 | Petersen | |
| 2016/0256483 A1 | 9/2016 | Petersen | |
| 2016/0346244 A1 | 12/2016 | Petersen | |
| 2017/0028014 A1 | 2/2017 | Petersen | |
| 2017/0196830 A1 | 7/2017 | Shanahan et al. | |
| 2017/0258925 A1 | 9/2017 | Petersen | |
| 2018/0271856 A1 | 9/2018 | Petersen et al. | |
| 2018/0291010 A1 | 10/2018 | Petersen et al. | |

FOREIGN PATENT DOCUMENTS

| | | |
|---|---|---|
| WO | WO 2003/086382 A1 | 10/2003 |
| WO | WO 2004/110358 A2 | 12/2004 |
| WO | WO 2008/011114 | 1/2008 |
| WO | WO 2008/011114 A2 | 1/2008 |
| WO | WO 2009/036108 A1 | 3/2009 |
| WO | WO 2009/051706 A2 | 4/2009 |
| WO | WO 2009/073445 | 6/2009 |
| WO | WO 2009/141826 A2 | 11/2009 |
| WO | WO 2010/003475 A2 | 1/2010 |
| WO | WO 2010/065877 A2 | 6/2010 |
| WO | WO 2010/096603 A2 | 8/2010 |
| WO | WO 2011/127304 A2 | 10/2011 |
| WO | WO 2011/150022 A2 | 12/2011 |
| WO | WO 2011/150088 A1 | 12/2011 |
| WO | WO 2012/122264 A1 | 9/2012 |
| WO | WO 2014/169026 A1 | 10/2014 |
| WO | WO 2017/100553 | 6/2017 |
| WO | WO 2017/123603 | 7/2017 |

OTHER PUBLICATIONS

Martyn et al, Anesthesiology 2008, vol. 109(1), pp. 137-148. (Year: 2008).*
Xavier et al, Diabetes Research and Clinical Practice 2014, vol. 105, pp. 356-363. (Year: 2014).*
Anderson, Chem & Biol 2003, vol. 10, pp. 787-797. (Year: 2013).*
Thiel, Nature Biotechnology 2004, vol. 22(5), pp. 513-519. (Year: 2004).*
Berge et al. "Pharmaceutical Salts" J. Pharm. Sci., 1977, vol. 66, No. 1, p. 1-19.
Arico-Muendel, C.C. et al., "Carbamate Analogues of Fumagillin as Potent, Targeted Inhibitors of Methionine Aminopeptidase-2", *J. Med. Chem.*, 52:8047-8056 (2009).
Bae, *J. Diabetes and its Complications*, (2016) v. 30, pp. 212-220.
Bernier, S.G. et al., "Fumagillin class inhibitors of methionine aminopeptidase-2", *Drugs of the Future*, 30(5):497-508 (2005).
Blencowe, C.A. et al., "Self-immolative linkers in polymeric delivery systems", *Polym. Chem.*, 2:773-790 (2011).
Brakenhielm et al. "Angiogenesis Inhibitor, TNP-470, Prevents Diet-Induced and Genetic Obesity in Mice", *Circulation Research*, 2004, vol. 94, p. 1579-1588.
Chau, Y. et al., "Antitumor efficacy of a novel polymer-peptide-drug conjugate in human tumor xenograft models", *Int. J. Cancer*, 118:1519-1526 (2006).
D'Souza, A.J.M. et al., "Release from Polymeric Prodrugs: Linkages and Their Degradation", *J. Pharm. Sci.*, 93(8):1962-1979 (2004).

(56) References Cited

OTHER PUBLICATIONS

Ducry, L. and Stump, B., "Antibody-Drug Conjugates: Linking Cytotoxic Payloads to Monoclonal Antibodies", *Bioconj. Chem.*, 21:5-13 (2010).

Esposito et al. "The metabolic syndrome and inflammation: association or causation?" Nutr. Metab. Cardiovasc. Dis. 14(5):228-232 (2004).

Golub et al. "Molecular Classification of Cancer: Class Discovery and Class Prediction by Gene Expression Monitoring", *Science*, vol. 286, (1999), pp. 531-537.

Han, C.K. et al., "Design and synthesis of highly potent fumagillin analogues from homology modeling for a human MetAP-2", *Biorg. Med. Chem. Lett.*, 10:39-43 (2000).

Herbst, R.S. et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", *Journal of Clinical Oncology*, 20(22):4440-4447 (2002).

Hughes, Thomas. ZGN-201 (ZGN), a Methionine Aminopeptidase 2 (MetAP2) Inhibitor, Durably Eliminates Excess Body Fat in Obese Mice Through Regulation of Fat Metabolism and Food Intake. American Diabetes Association. 2010. Abstract No. 1803-P.

Jeong, B-S. et al., "Total synthesis and antiangiogenic activity of cyclopentane analogues of fumagillol", *Bioorganic and Medicinal Chemistry Letters*, 15:3580-3583 (2005).

Joharapurkar et al. "Inhibition of the methionine aminopeptidase 2 enzyme for the treatment of obesity." *Diabetes, Metaboloic Syndrome & Obesity: Targets and Therapy*, 2014:7, pp. 73-84.

Kahn et al., "Mechanisms linking obesity to insulin resistance and type 2 diabetes," Nature, v. 444, 2006, pp. 840-846.

Kim et al., "5-Demethoxyfumagillol, a Potent Angiogenesis Inhibitor Isoloated from Aspergillus fumigatus", Chem. Pharm. Bull., 52(4): 447-450 (2004).

Kim et al. "Assessment of the anti-obesity effects of the TNP-470 analog, CKD-732", *Journal of Molecular Endocrinology*, 2007, vol. 38, p. 455-465.

Klok M. D. et al., "The role of leptin and ghrelin in the regulation of food intake and body weight in humans: a review", *Obesity Reviews* (2007), vol. 8, pp. 21-34.

Law and Tung, "Proteolysis: A Biological Process Adapted in Drug Delivery, Therapy, and Imaging", *Bioconjugate Chem.*, 20:1683-1695 (2009).

Lee, H.W. et al., "Design, Synthesis, and Antiangiogenic Effects of a Series of Potent Novel Fumagillin Analogues", *Chem. Pharm. Bull.*, 55(7):1024-1029 (2007).

Lijnen et al. "Fumagillin Reduces Adipose Tissue Formation in Murine Models of Nutritionally Induced Obesity", Obesity, 2010, vol. 18, No. 12, p. 2241-2246.

Mann-Steinberg and Satchi-Fainaro, "TNP-470: The Resurrection of the First Synthetic Angiogenesis Inhibitor", *Folkman and Figg, Angiogenesis: An Integrative Approach from Science to Medicine*, 35:395-414 (2008).

Mason and Joyce. "Proteolytic Networks in Cancer." *Trends in Cell Biology*. 21(4) pp. 228-237 (2011).

Satchi-Fainaro, R. et al., "Targeting angiogenesis with a conjugate of HPMA copolymer and TNP-470", Nature Med., 10(3): 255-261 (2004).

Segal, E. et al., "Design and development of polymer conjugates as anti-angiogenic agents", Adv. Drug. [deliv. Reviews, 61 (13): 1159-1176 (2009).

Shiose, Y. et al., "Relationship between Drug Release of DE-310, Macromolecular Prodrug of DX-8951f, and Cathepsins Activity in Several Tumors", *Biol. Pharm. Bull.*, 30(12):2365-2370 (2007).

Shiose, Y. et al., "Systematic Research of Peptide Spacers Controlling Drug Release from Macromolecular Prodrug System, Carboxymethyldextran Polyalcohol—Peptide—Drug Conjugates", *Bioconjugate Chem.*, 20(1):60-70 (2009).

Subr, V. et al., "Poly[M-)2-hydroxypropyl)methacrylamide] Conjugates of Methotrexate Synthesis and in vitro Drug Release", *J Controlled Release*, 49:123-132 (1997).

Sutherland, J. et al. "The Metabolic Syndrome and Inflammation" *Metabolic Syndrome and Related Disorders* 2(2):82-104 (2004).

Goktas et al., "Prostate Cancer and Adiponectin", Adult Urology, 2005, 65 (6), p. 1168-1172.

\* cited by examiner

METAP2 INHIBITORS AND METHODS OF TREATING OBESITY

CROSS-REFERENCE TO RELATED APPLICATIONS

This application is a continuation of U.S. patent application Ser. No. 15/665,755, filed Aug. 1, 2017 (now allowed), which is a continuation of U.S. patent application Ser. No. 15/226,258, filed Aug. 2, 2016 and patented as U.S. Pat. No. 9,750,737 issued Sep. 5, 2017, which is a continuation of U.S. patent application Ser. No. 14/851,668, filed Sep. 11, 2015 now U.S. Pat. No. 9,433,600, issued Sep. 6, 2016, which is a continuation of U.S. application Ser. No. 14/248,787, filed Apr. 9, 2014, now U.S. Pat. No. 9,173,956, issued Nov. 3, 2015 which claims the benefit of U.S. Provisional Application No. 61/810,468, filed Apr. 10, 2013 and U.S. Provisional Application No. 61/925,918, filed Jan. 10, 2014. The contents of each of these applications are incorporated herein by reference in their entirety.

BACKGROUND OF THE INVENTION

Obesity is a chronic disease and a major health concern in modern society. According to the Centers for Disease Control (CDC), the United States is in the midst of an epidemic of obesity. In the U.S., about 65% of adults are overweight, 30% of adults are obese, with more than 5 million adults classified as morbidly obese. Ten million more are near that mark and may be at risk for obesity-related health problems. The problem is increasing; obesity in children and adolescents increased two-fold in the last two decades.

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. However, these existing therapies are not very effective. Adherence to energy restriction diets is problematic and generally unsuccessful and medical therapies have only modest efficacy for long-term weight management. In most cases, toxicity and side effects have hampered the development of potential weight loss drug candidates. Metabolic syndrome (Sutherland, et al., Metabolic Syndrome and Related Disorders 2:82-104 (2004); Esposito, et al., Nutr. Metab. Cardiovasc. Dis. 14:228-232 (2004)), relates to obesity and is characterized by a group of metabolic risk factors including: 1) abdominal obesity (excessive fat tissue in and around the abdomen); 2) atherogenic dyslipidemia (high triglycerides; low HDL cholesterol and high LDL cholesterol); 3) elevated blood pressure; 4) insulin resistance or glucose intolerance; 5) a prothrombotic state (e.g., high fibrinogen or plasminogen activator inhibitor-1 in the blood); and 6) a proinflammatory state (e.g., elevated CRP in the blood). Metabolic syndrome has become increasingly common in developed countries and is closely associated with risk of coronary heart disease (Malik, et al., Circulation 110:1245-1250 (2004); Irabarren, et al., J. Am. Coll. Cardiol. 48:1800-1807 (2006)).

Cardiometabolic syndrome includes obesity-related metabolic disorders and atherosclerosis. Cardiometabolic disorders also promote arterial and valvular calcification which may lead to devastating clinical complications: acute myocardial infarction and aortic stenosis. In addition, diabetes causes chronic kidney disease that also leads to cardiovascular ectopic calcification and acute myocardial infarction. Collectively, several major components of the cardiometabolic syndrome, developed via interrelated mechanisms, enhance each other through local or systemic inflammation. Further, lack of patient adherence to prescribed medications poses a tremendous challenge to the global healthcare community. In the US alone, avoidable medical spending was estimated at $300 billion in 2009. With blockbuster expiries, drying pipelines and increasing cost-containment by payers, bridging the adherence gap is a "must do" for pharmaceutical companies.

Accordingly, new compounds and methods for causing, inducing and/or increasing weight loss and treating obesity and metabolic syndrome are needed. The present invention addresses these needs.

SUMMARY OF THE INVENTION

The present invention provides methods of inducing or causing weight loss in a subject in need thereof comprising administering at least one compound of the present invention in a therapeutically effective amount to the subject to induce or cause weight loss. In certain embodiments, the subject is overweight or obese. In certain embodiments, inducing or causing weight loss is increasing weight loss.

The present invention also provides methods of treating obesity, metabolic syndrome and/or related co-morbidities in a subject in need thereof comprising administering at least one compound of the present invention, or a pharmaceutically acceptable salt, prodrug, metabolite, analog or derivative thereof, in a therapeutically effective amount on a reasonable schedule to the subject to treat or ameliorate these diseases and conditions.

The present invention also provides methods of improving insulin sensitivity and glycemic control, reducing insulin levels and/or improvements in leptin sensitivity in a subject in need thereof comprising administering at least one compound of the present invention, or a pharmaceutically acceptable salt, prodrug, metabolite, analog or derivative thereof, in a therapeutically effective amount on a reasonable schedule to the subject to treat or ameliorate these diseases and conditions.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

DETAILED DESCRIPTION OF THE INVENTION

Compounds of the Present Invention

Figure 1:
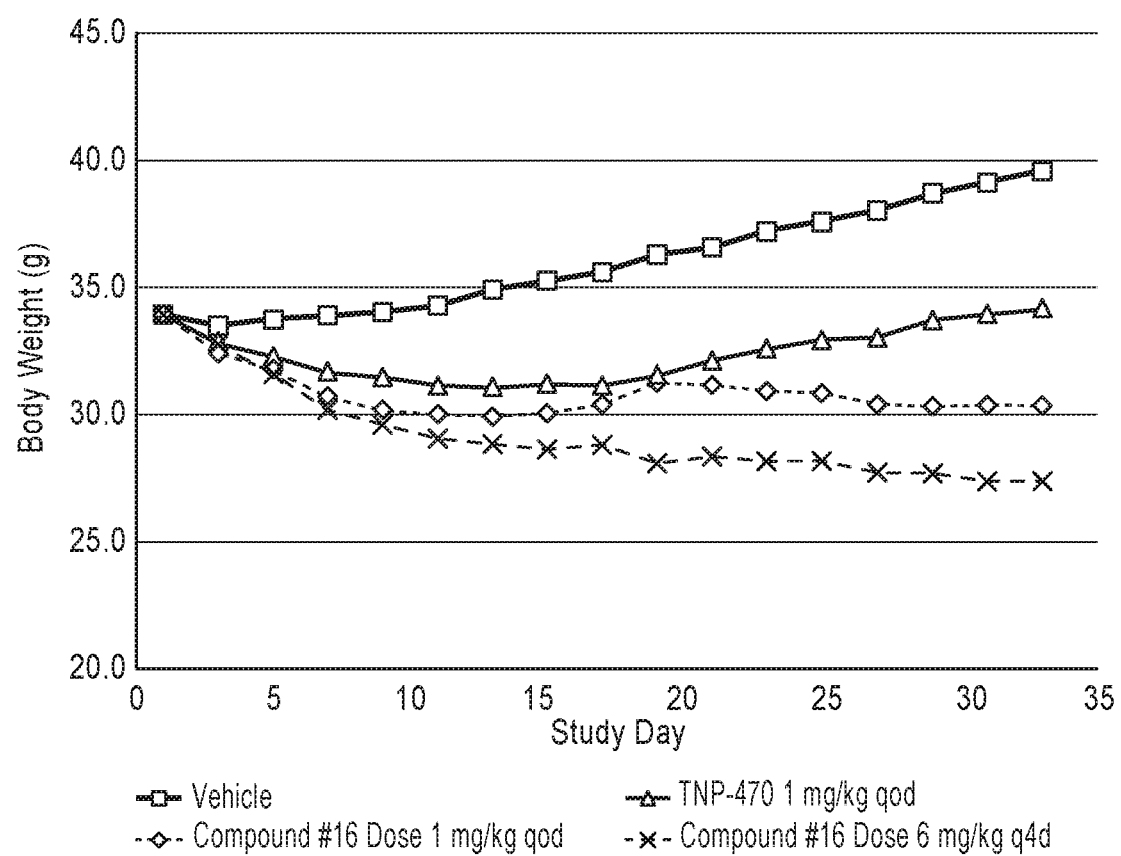
FIG. 1 is a graph showing body weight change over time following administration of compounds of the present invention.

The present invention provides drug conjugate compositions including an active moiety modified, a conjugate moiety, and a cleavable linker, wherein cleavage of the linker occurs substantially in a target tissue to produce a modified active moiety having reduced efflux from target tissue compared to the unmodified active moiety. The present invention also provides compositions including a modified active moiety.

The conjugate moiety used depends on the physicochemical properties of both the conjugate moiety and the active moiety, in addition to biological requirements, e.g., pharmacokinetic and pharmacodynamic properties of the active moiety and knowledge of the disease state. One of skill in the art will be able to select an appropriate conjugate moiety based upon the above considerations. The conjugate moiety may be used to deliver small molecule active moieties or larger molecule active moieties, such as proteins, peptides, or oligonucleotides.

The conjugate moiety improves the delivery of an active moiety to target. The conjugate moiety is chosen to maximize bioavailability of the active moiety, optimize onset, duration, and rate of delivery of the active moiety, and maintain the concentration of an active moiety in a target tissue within a therapeutic range as long as required for effective treatment. The conjugate moiety may also assist in minimizing adverse side effects of an active moiety. Thus the conjugate moiety prolongs pharmacological activity of an active moiety, stabilizes labile active moieties from chemical and proteolytic degradation, minimizes side effects, increases solubility, and targets the active moiety to specific cells or tissues.

Other properties of the conjugate moiety to be considered are that the conjugate moiety is minimally or non-immunogenic and non-toxic. The molecular weight of the conjugate moiety should be sufficiently large to avoid rapid elimination via kidney ultrafiltration and low enough to prevent undesirable accumulation within the body. In certain embodiments, the conjugate moiety is hydrophilic and is biodegradable. Conjugate moieties that are non-biodegradable are also suitable with compositions and methods of the invention. The conjugate moiety should be able to carry the required amount of active moiety and protect against premature metabolism of the active moiety in transit to the target tissue.

Exemplary conjugates include all forms of polymers, synthetic polymers as well as natural product related polymers including peptides, polysaccharides, polynucleic acids, antibodies and aptamers. In preferable embodiments, the conjugate is a synthetic polymer. Exemplary polymers of the invention have been described in U.S. Pat. No. 4,997,878 to Bock et al, U.S. Pat. No. 5,037,883 to Kopecek et al. U.S. Pat. No. 5,258,453 to Kopecek et al., U.S. Pat. No. 6,464,850 to Zhang et al., U.S. Pat. No. 6,803,438 to Brocchini et al., each of which is incorporated by reference in its entirety. Additional exemplary polymers have been described in Subr et al., J Controlled Release, 18, 123-132 (1992). In some embodiments, the method of synthesis of the polymer may lead to the coupling of two or more polymer chains and may increase the weight average molecular weight of the polymer conjugate. It is further recognized that if this coupling occurs, the linkages will be biodegradable.

The active moiety may be any compound or molecule that produces a therapeutic effect in a subject. In certain embodiments, the compound or molecule has a molecular weight of 2000 Daltons or less, 1500 Daltons or less, 1000 Daltons or less, 500 Daltons or less, or 250 Daltons or less. In certain embodiments, the compound or molecule is a MetAP2 inhibitor. In certain embodiments, the compound or molecule is fumagillin, fumagillol, or an analog, derivative, salt or ester thereof. The compound or molecule chosen will depend on the condition or disease to be treated. In certain embodiments, two or more active moieties may be used. In certain embodiments an active moiety and an inactive "capping" moiety may be used. In certain embodiments, the condition to be treated is obesity. In compositions of the invention, the conjugate moiety is joined to the active moiety via a linker. Any linker structure known in the art may be used to join the modified active moiety to the conjugate moiety. The linker used will depend on the physiological conditions of the target tissue, the properties of the active moiety that are being optimized, and the cleavage mechanism. D'Souza et al. review various types of linkers including linkers that operate via proteolytic cleavage "Release from Polymeric Prodrugs: Linkages and Their Degradation" J. Pharm. Sci., 93, 1962-1979 (2004). Blencoe et al. describe a variety of self-immolative linkers, "Self-immolative linkers in polymeric delivery systems" Polym. Chem. 2, 773-790 (2011). Ducry et al. review linkers in Bioconj. Chem. 21, 5-13 (2010) "Antibody-Drug Conjugates: Linking Cytotoxic Payloads to Monoclonal Antibodies". Peptide linkers suitable for cleavage by matrix metalloproteins (MMPs) are described in Chau et al. "Antitumor efficacy of a novel polymer-peptide-drug conjugate in human tumor xenograft models" Int. J. Cancer 118, 1519-1526 (2006) and Chau et al. U.S. patent publication number 2004/0116348. Other linker chemistries suitable with compositions of the invention are shown in Shiose et al. Biol. Pharm. Bull. 30(12) 2365-2370 (2007); Shiose et al. Bioconjugate Chem. 20(1) 60-70 (2009); Senter, U.S. Pat. No. 7,553,816; De Groot, U.S. Pat. No. 7,223,837; King, U.S. Pat. No. 6,759,509; Susaki, U.S. Pat. No. 6,835,807; Susaki U.S. Pat. No. 6,436,912; and Gemeinhart U.S. Pat. No. 7,943,569.

In certain embodiments, the linker is a peptide linker. Exemplary peptide linkers are described in U.S. Pat. No. 6,835,807 to Susaki et al., U.S. Pat. No. 6,291,671 to Inoue et al., U.S. Pat. No. 6,811,996 to Inoue et al., U.S. Pat. No. 7,041,818 to Susaki et al., U.S. Pat. No. 7,091,186 to Senter et al., U.S. Pat. No. 7,553,816 to Senter et al. each of which is incorporated by reference in its entirety. Additional exemplary peptides and their cleavage have been described in Shiose et al. Biol. Pharm. Bull. 30(12) 2365-2370 (2007) and Shiose et al. Bioconjugate Chem. 20(1) 60-70 (2009). Peptide linkers suitable for cleavage by matrix metalloproteins (MMPs) are described in Chau et al. "Antitumor efficacy of a novel polymer-peptide-drug conjugate in human tumor xenograft models" Int. J. Cancer 118, 1519-1526 (2006) and Chau et al. U.S. patent publication number 2004/0116348.

The linker may be cleaved by any mechanism known in the art. For example, the linkers may be designed for proteolytic cleavage or intracellular proteolytic cleavage. In certain embodiments, the linker is designed such that there is no cleavage of the linker in plasma or there is a very low rate of cleavage in the plasma. Exemplary linker structures are described in further detail below.

In certain embodiments, the linker has a structure such that it is to be preferentially cleaved in disease tissue. Since most hydrolases exist in both normal and diseased tissue, the linker should be cleaved by a hydrolase that is more active in disease tissue and/or more prevalent in disease tissue. For example, tumors have generally upregulated metabolic rates and in particular over express proteases including the cathepsins. The upregulation and role of proteases in cancer is described by Mason et al. Trends in Cell Biology 21, 228-237 (2011).

In certain embodiments, the class of active moieties that are modified are moieties that irreversibly bind to their targets, i.e., after release from the conjugate the active moiety covalently binds to the biochemical target. Once bound, the active moiety cannot diffuse or be transported out of the cell. For targeting to occur in the case of irreversible binding, the rate of small molecule binding to target, $k_{rev1}$, should be significant relative to the rate of small molecule efflux, $k_{sm-1}$. If the rate of efflux is high relative to small molecule binding, small molecule equilibrium will be established between the plasma and the intracellular compartment and there will be no advantage to intracellular delivery relative to extracellular delivery.

In other embodiments, the class of active moieties that are modified are moieties that reversibly bind to their targets. For targeting to occur in the case of reversible binding, the equilibrium constant for small molecule binding to target $K=k_{rev1}/k_{rev-1}$ should be large and the "on-rate", $k_{rev1}$, should be large relative to the rate of small molecule efflux, $k_{sm-1}$. If the rate of efflux is high relative to small molecule binding, small molecule equilibrium will be established between the plasma and the intracellular compartment and there will be no advantage to intracellular delivery relative to extracellular delivery. Such a relationship is described schematically below, where: [PC]=concentration of polymer conjugate; [SM]=concentration of released small molecule; plasma=plasma concentration; icell=intracellular concentration; icell-target=small molecule reversibly bound to intracellular target; and inactive=inactive metabolite of small molecule. In certain embodiments, when $k_{rev-1}$=zero, the moiety irreversibly binds to its target.

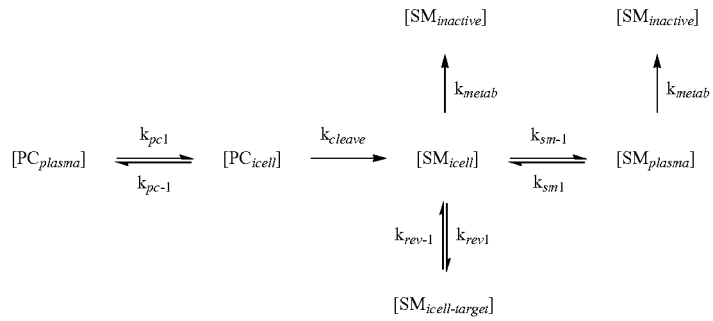

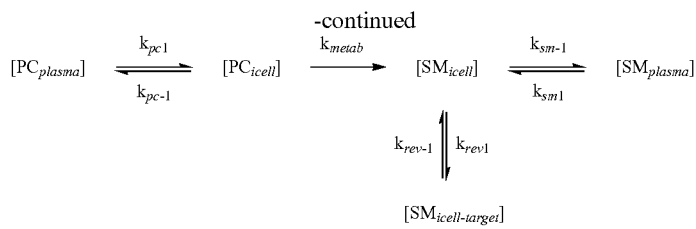

In other embodiments, the class of active moieties that are modified are moieties that have very high equilibrium constants and high "on-rates" relative to efflux. In other embodiments, the class of active moieties that are modified are moieties that undergo intracellular metabolism at a high rate relative to efflux.

In certain embodiments, modifications to the active moiety are accomplished by using a linker having a structure such that upon cleavage, a fragment of the linker remains attached to the active moiety. That fragment may change any of the molecular weight, hydrophobicity, polar surface area, or charge of the active moiety, thereby producing a modified active moiety having reduced efflux from a target cell compared to the unmodified active moiety. For example, coupling MetAP2 inhibitory active moieties via the linkers described herein provide conjugates in which upon cleavage of the linker, produce an active moiety having a fragment of the linker attached thereto (modified active moiety). The modified active moieties described herein may have reduced efflux from a cell compared to the unmodified active moieties, resulting in modified active moieties with superior efficacy to the parent small molecules and superior efficacy to the parent small molecules and superior pharmacokinetic profiles.

The present invention provides conjugates with linkers having the structure:

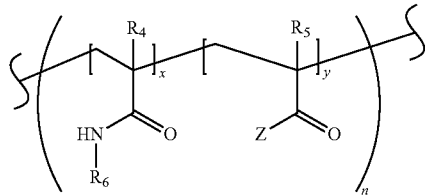

wherein, independently for each occurrence, $R_4$ is H or $C_1$-$C_6$ alkyl; $R_5$ is H or $C_1$-$C_6$ alkyl; $R_6$ is $C_2$-$C_6$ hydroxyalkyl; Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W; $AA_1$ is glycine, alanine, or $H_2N(CH_2)mCO_2H$, wherein m is 2, 3, 4 or 5; $AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; $AA_5$ is a bond, or glycine, valine, tyrosine, tryptophan, phenylalanine, methionine, leucine, isoleucine, or asparagine; $AA_6$ is a bond, or alanine, asparagine, citrulline, glutamine, glycine, leucine, methionine, phenylalanine, serine, threonine, tryptophan, tyrosine, valine, or $H_2N(CH_2)mCO_2H$, wherein m is 2, 3, 4 or 5; L is —OH, —O-succinimide, —O-sulfosuccinimide, alkoxy, aryloxy, acyloxy, aroyloxy, alkoxycarbonyloxy, aryloxycarbonyloxy, —NH$_2$, —NH($C_2$-$C_6$ hydroxyalkyl), halide or perfluoroalkyloxy; Q is NR, O, or S; X is M-(C(R)$_2$)$_p$-M-J-M-(C(R)$_2$)$_p$-M-V; M is a bond, or C(O); J is a bond, or ((CH$_2$)$_q$Q)$_r$, $C_5$-$C_8$ cycloalkyl, aryl, heteroaryl, NR, O, or S; Y is NR, O, or S; R is H or alkyl; V is a bond or

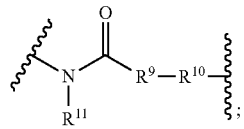

$R^9$ is alkyl, aryl, aralkyl, or a bond; or $R^9$ taken together with Y forms a heterocyclic ring; $R^{10}$ is amido or a bond; $R^{11}$ is H or alkyl; W is a MetAP2 inhibitor moiety or alkyl; x is in the range of 1 to about 450; y is in the range of 1 to about 30; n is in the range of 1 to about 50; p is 0 to 20; q is 2 or 3; and r is 1, 2, 3, 4, 5, or 6.

In certain embodiments, $R_4$ is $C_1$-$C_6$ alkyl. In certain embodiments, $R_4$ is methyl. In certain embodiments, $R_5$ is $C_1$-$C_6$ alkyl. In certain embodiments, $R_5$ is methyl. In certain embodiments, $R_6$ is 2-hydroxyethyl, 2-hydroxypropyl or 3-hydroxypropyl. In certain embodiments, $R_6$ is 2-hydroxypropyl.

In certain embodiments, the compound has a molecular weight of less than about 60 kDa. In other embodiments, the molecular weight is less than about 45 kDa. In other embodiments, the molecular weight is less than about 35 kDa.

In certain embodiments, the ratio of x to y is in the range of about 30:1 to about 3:1. In other embodiments, the ratio of x to y is in the range of about 19:2 to about 7:2. In certain embodiments, the ratio of x to y is in the range of about 9:1 to about 4:1. In certain embodiments, the ratio of x to y is about 11:1. In certain embodiments, the ratio of x to y is about 9:1. In certain embodiments, the ratio of x to y is about 4:1.

In certain embodiments, Z is —NH-$AA_1$-$AA_2$-$AA_3$-$AA_4$-$AA_5$-$AA_6$-C(O)-L. In certain embodiments, L is methoxy, ethoxy, pentafluorophenyloxy, phenyloxy, acetoxy, fluoride, chloride, methoxycarbonyloxy; ethoxycarbonyloxy, phenyloxycarbonyloxy, 4-nitrophenyloxy, trifluoromethoxy, pentafluoroethoxy, or trifluoroethoxy. In certain embodiments, L is 4-nitrophenyloxy.

In certain embodiments, Z is —NH-$AA_1$-$AA_2$-$AA_3$-$AA_4$-$AA_5$-$AA_6$-C(O)-Q-X—Y—C(O)—W. In certain embodiments, $AA_1$ is glycine. In certain embodiments, $AA_2$ is glycine. In certain embodiments, $AA_3$ is glycine. In certain embodiments, $AA_4$ is glycine or phenylalanine. In certain embodiments, $AA_5$ is leucine, phenylalanine, valine or tyrosine. In certain embodiments, $AA_6$ is asparagine, citrulline, glutamine, glycine, leucine, methionine, threonine or tyrosine. In certain embodiments, $AA_5$-$AA_6$ is Leu-Cit, Leu-Gln, Leu-Gly, Leu-Leu, Leu-Met, Leu-Thr, Phe-Cit, Phe-Gln, Phe-Leu, Phe-Met, Phe-Thr, Val-Asn, Val-Cit, Val-Gln, Val-Leu, Val-Met, Val-Thr, Tyr-Cit, Tyr-Leu, or Tyr-Met. In certain embodiments, $AA_1$, $AA_3$ and $AA_5$ are glycine, valine, tyrosine, tryptophan, phenylalanine, methionine, leucine, isoleucine, or asparagine. In certain embodiments, $AA_2$, $AA_4$ and $AA_6$ are glycine, asparagine, citrulline, glutamine, glycine, leucine, methionine, phenylalanine, threonine or tyrosine. In certain embodiments, $AA_2$ is a bond; and $AA_3$ is a bond. In certain embodiments, $AA_1$ is glycine; $AA_4$ is phenylalanine; $AA_5$ is leucine; and $AA_6$ is glycine.

In certain embodiments, W is

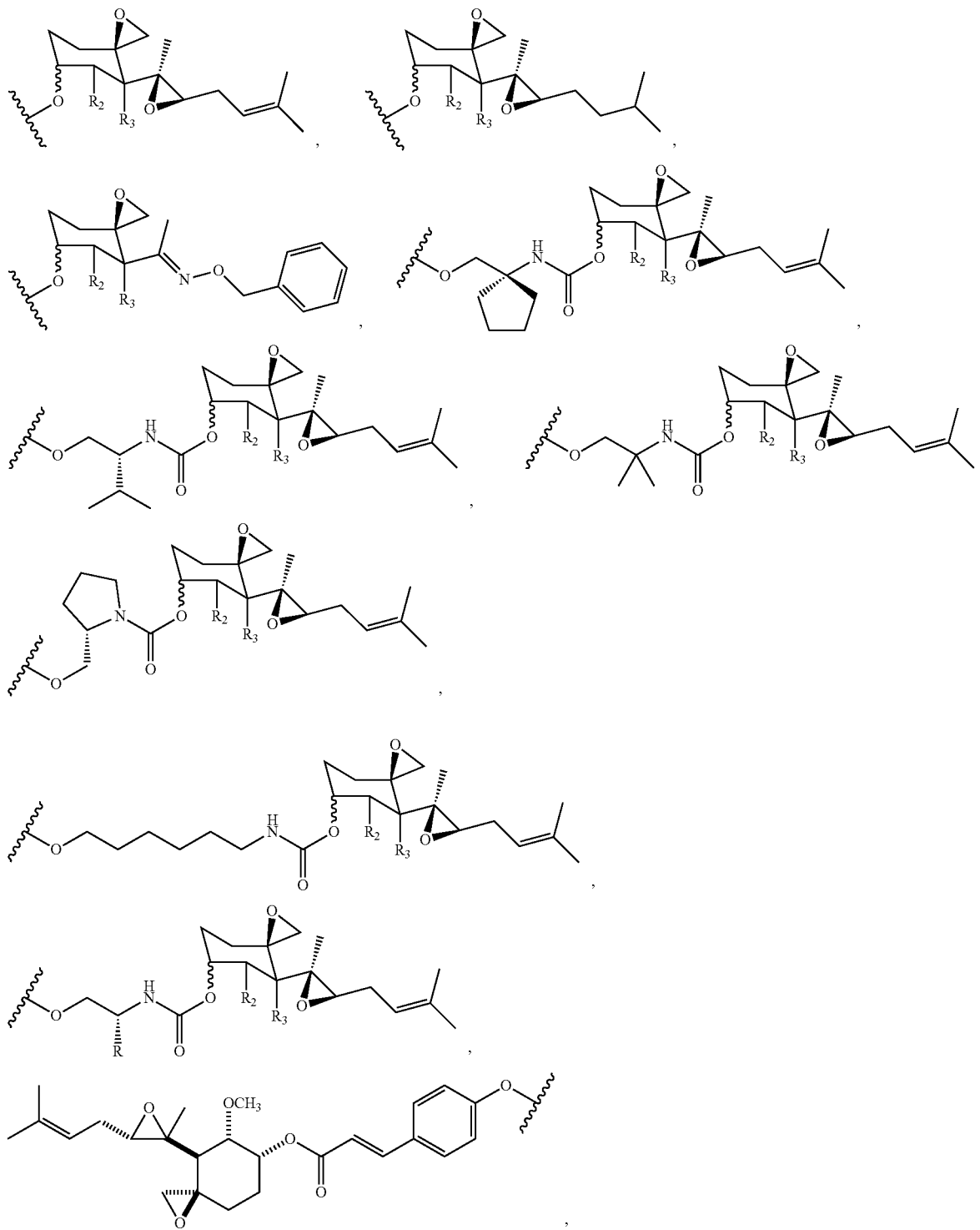

-continued
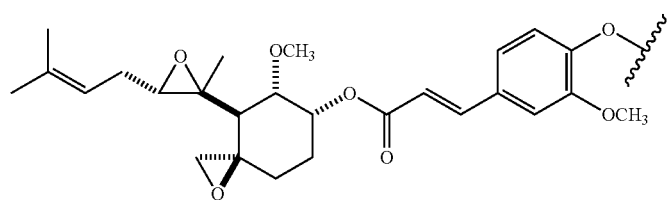
,
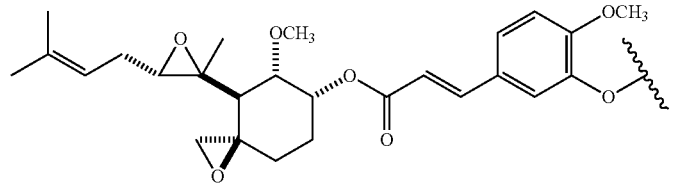
,
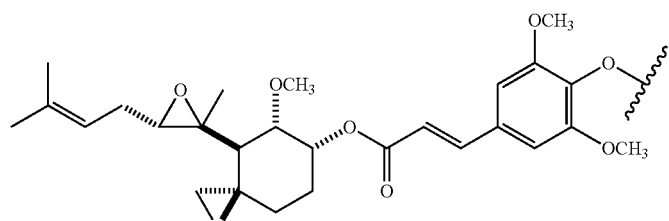
,
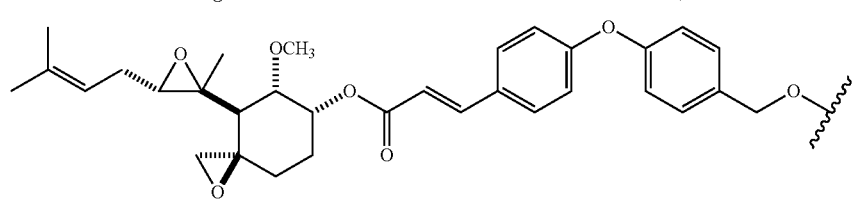
,
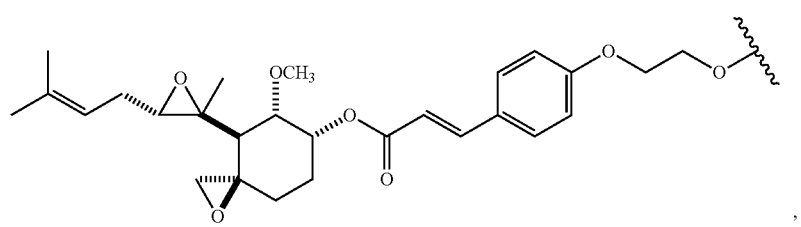
,
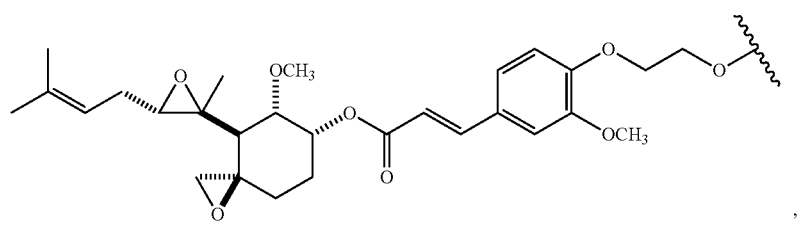
,
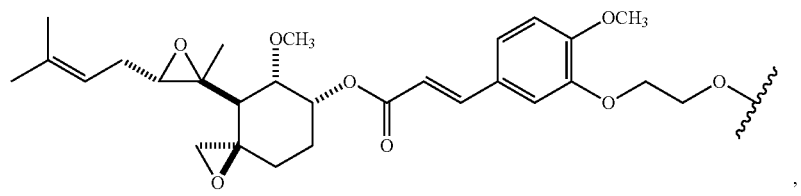
,
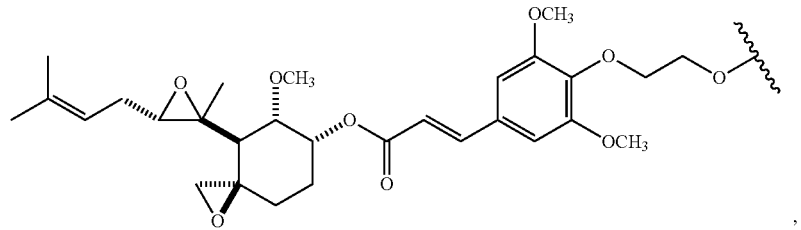
, -continued
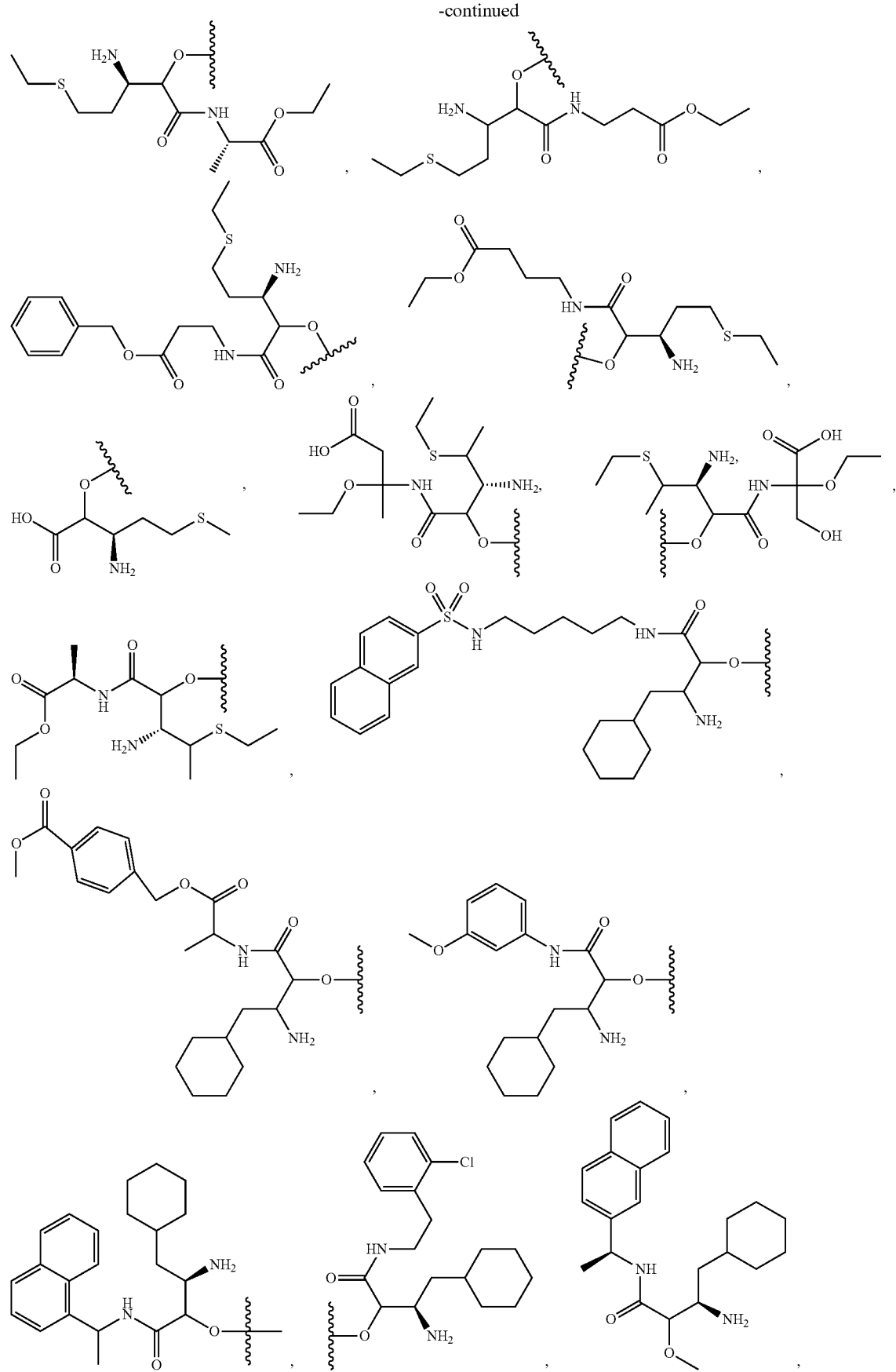

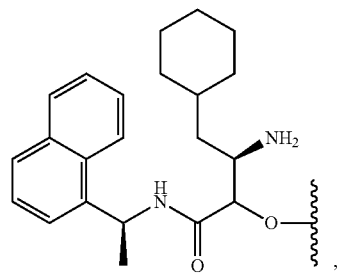
,
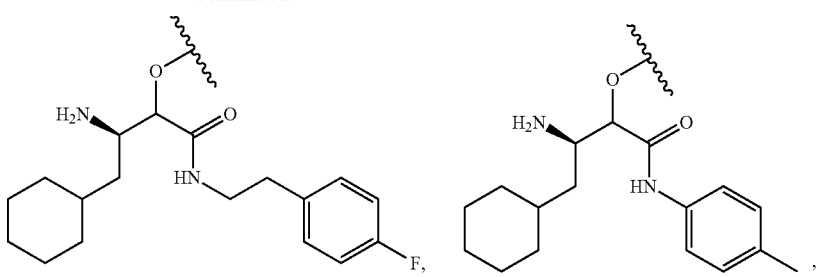
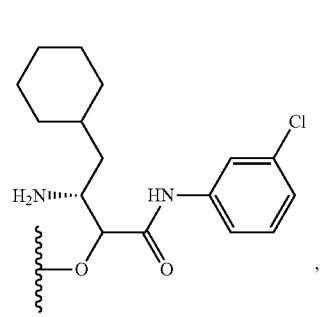
,
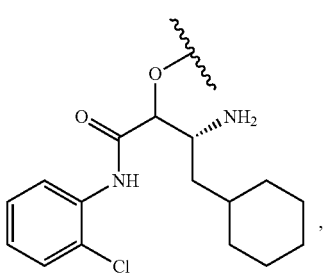
,
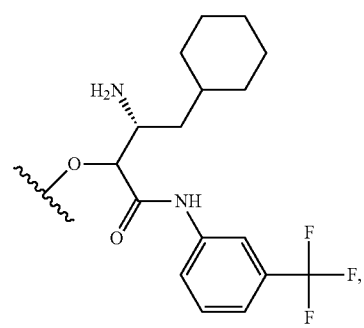
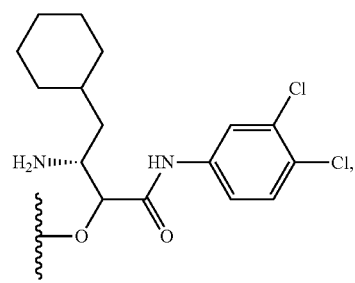
,
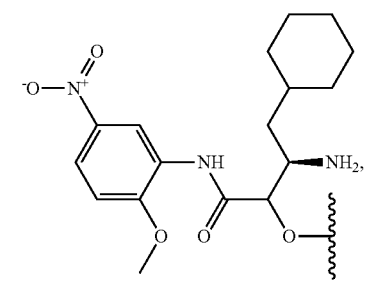
,
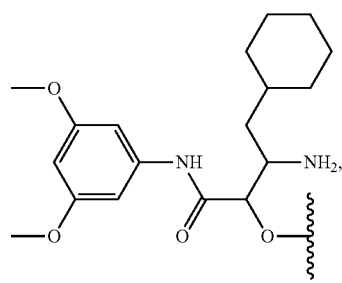
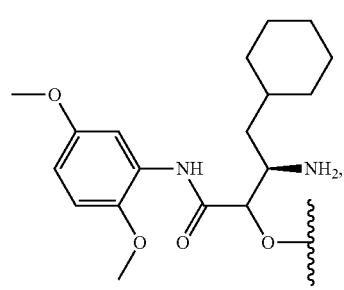
,
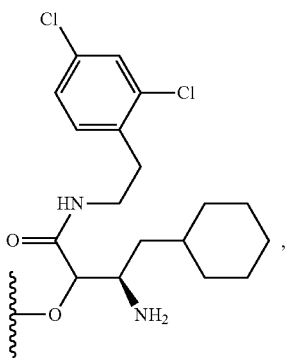
,
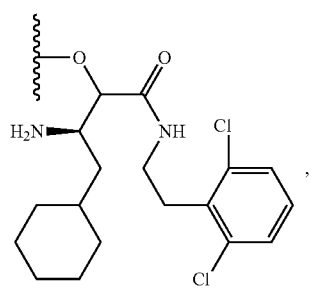
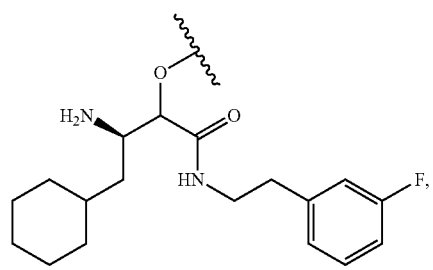
,
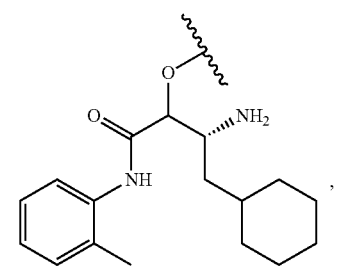
,
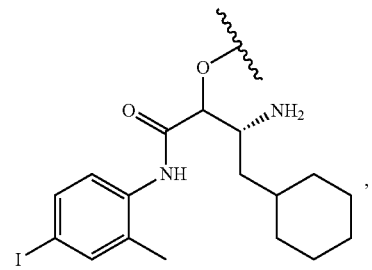
,

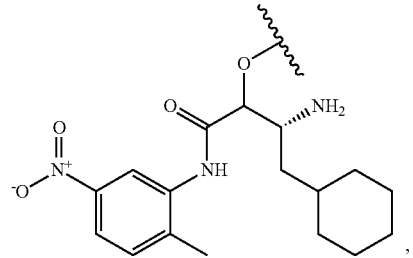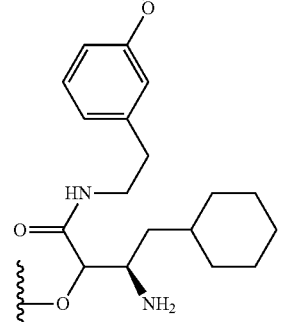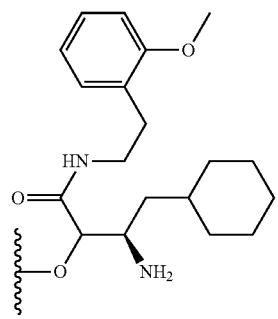
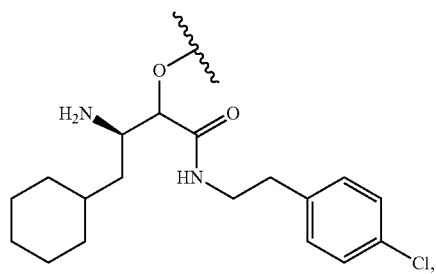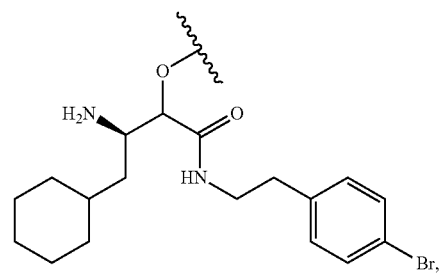
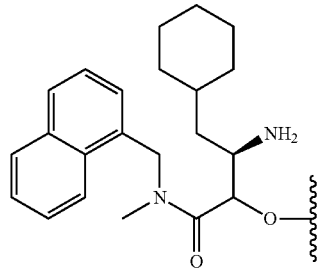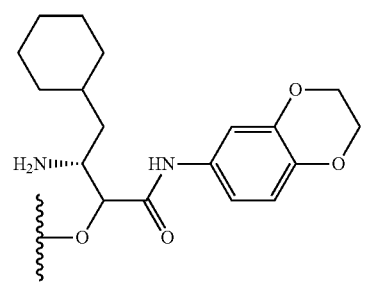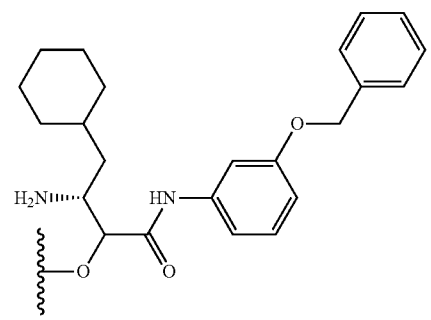
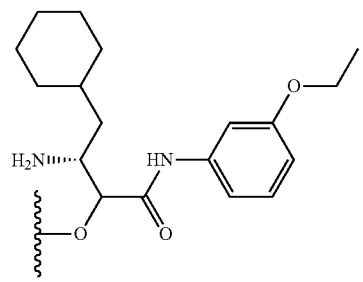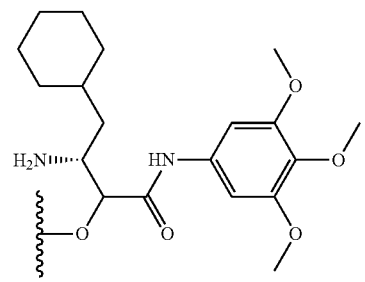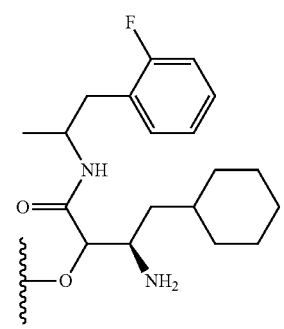
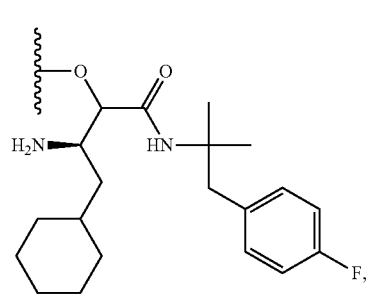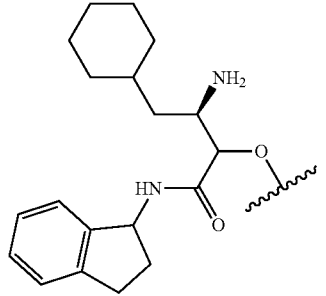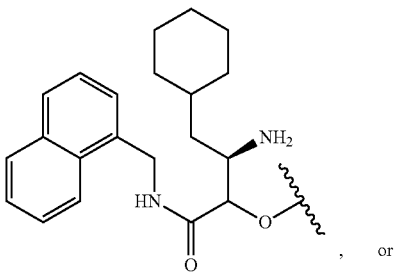

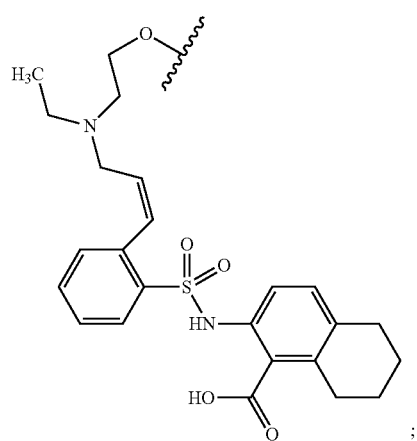
wherein $R_2$ is —OH or methoxy; and $R_3$ is H, —OH or methoxy.
In certain embodiments, W is
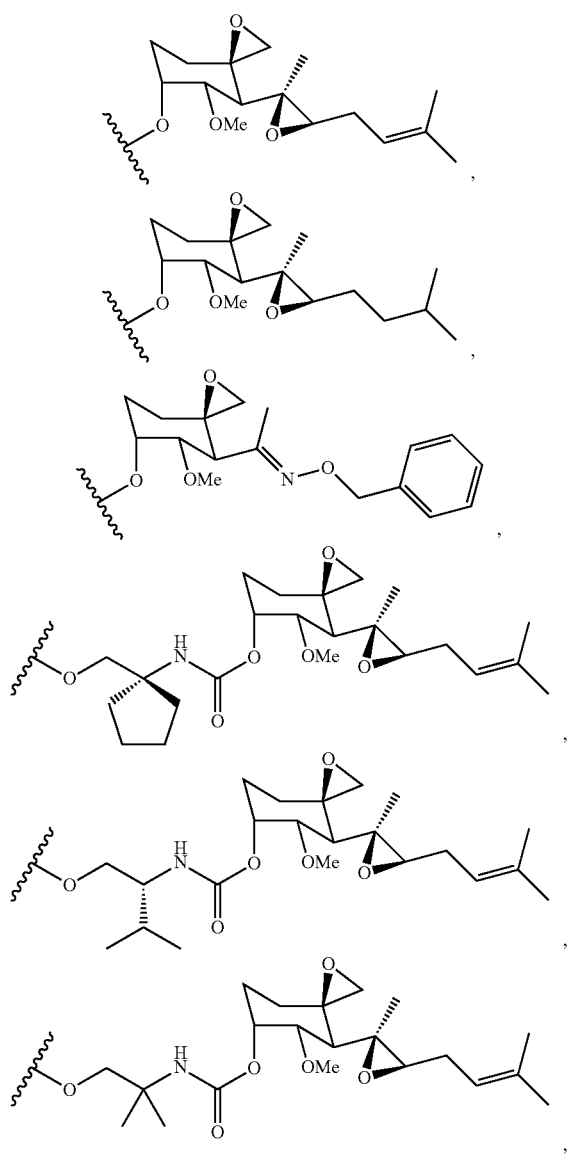
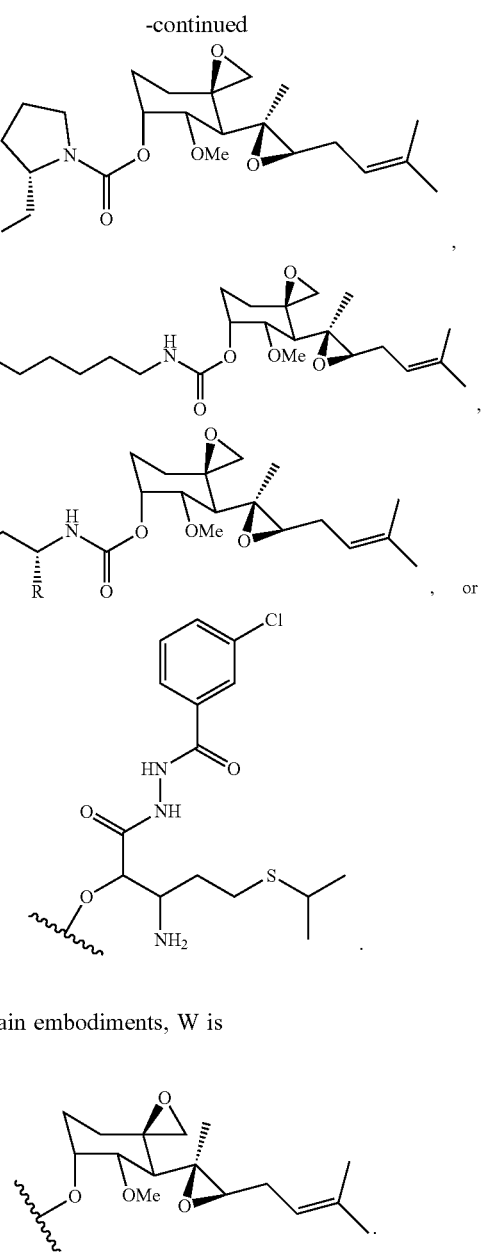
In certain embodiments, W is In certain embodiments, Q is NR. In other embodiments, Q is S.
In certain embodiments, J is NR. In other embodiments, J is $((CH_2)_qQ)_r$. In other embodiments, J is $C_5$-$C_8$ cycloalkyl. In certain embodiments, J is aryl.
In certain embodiments, Y is NR. In other embodiments, Y is S.
In certain embodiments, -Q-X—Y— is
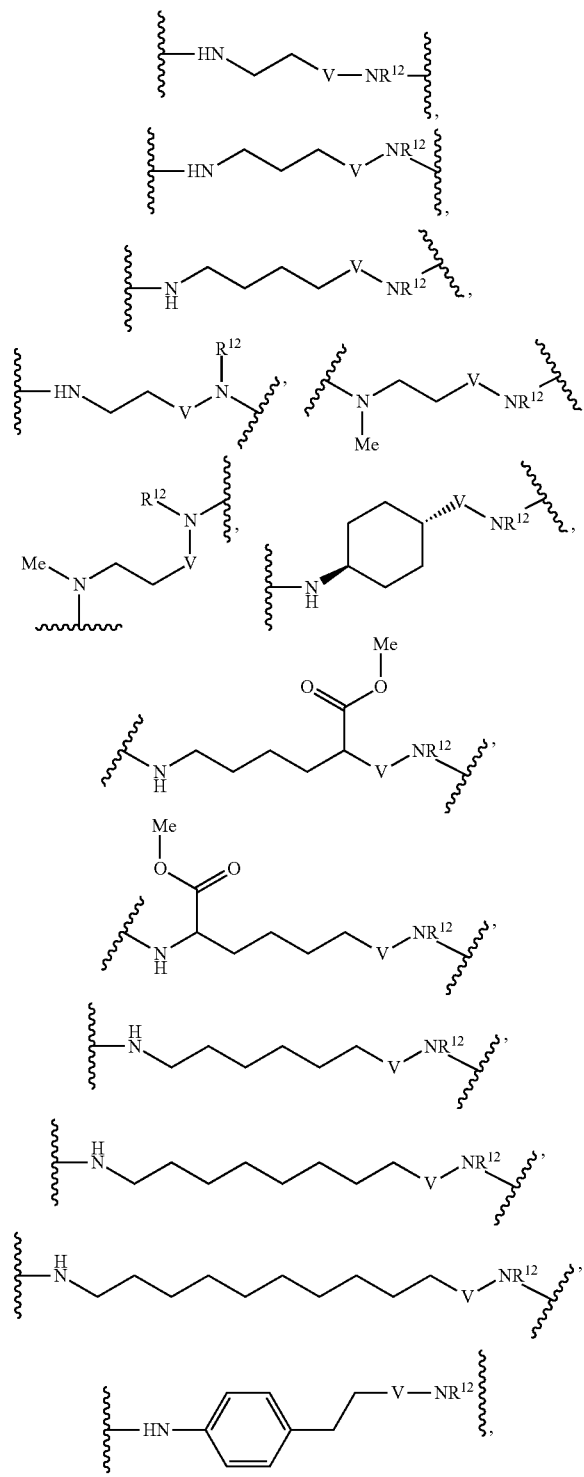
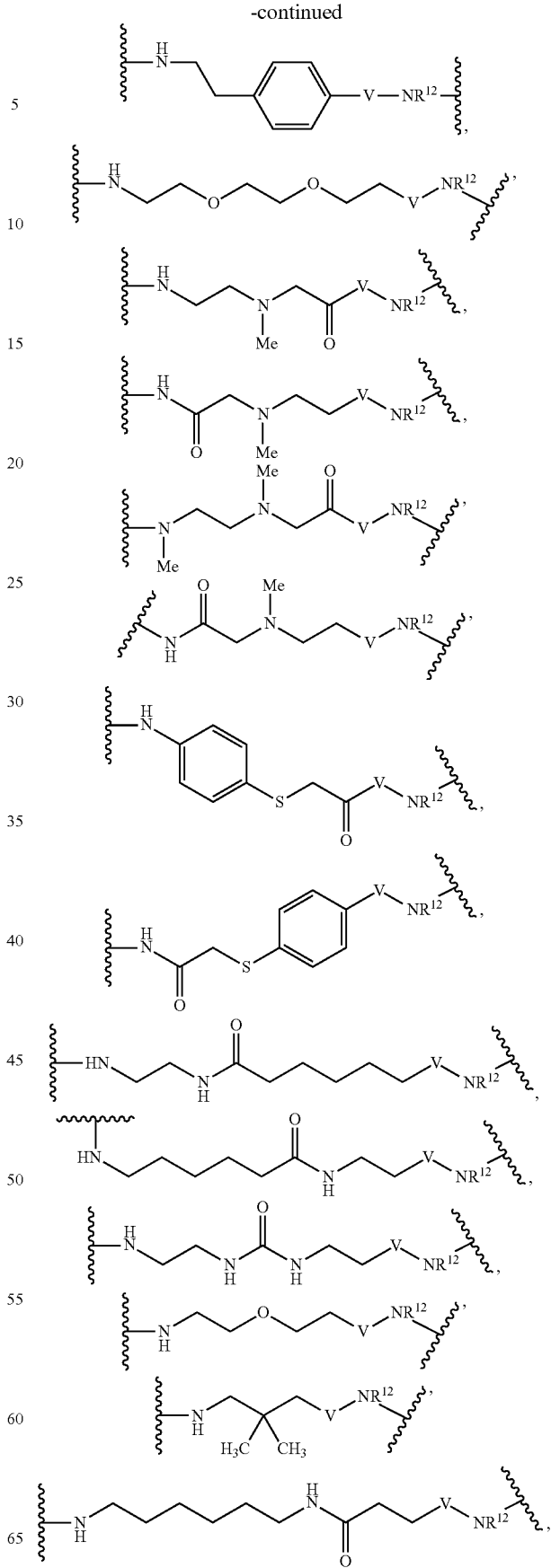

-continued

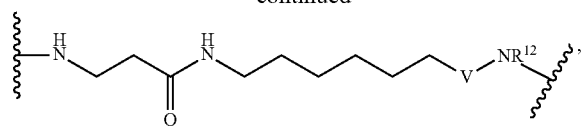

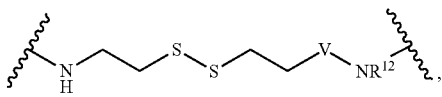

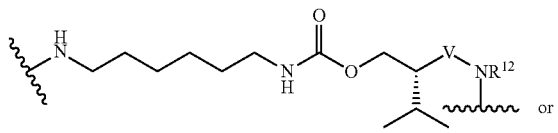 or

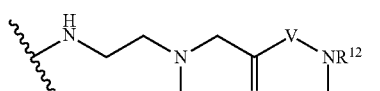

V is:

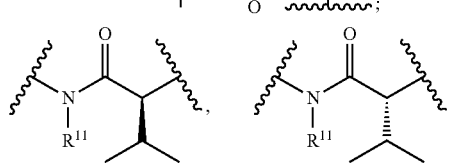

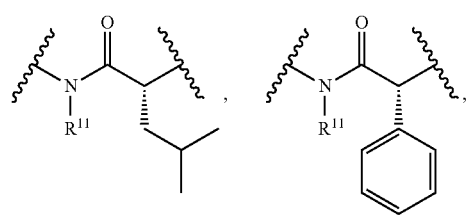

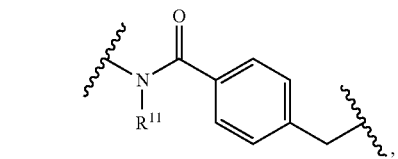

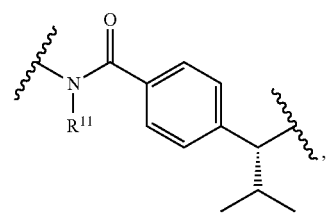

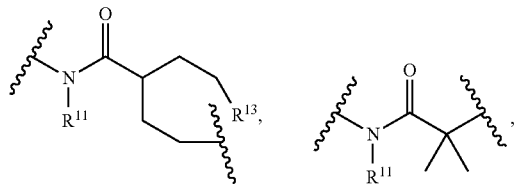

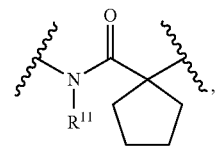

or a bond; $R^{12}$ is H or Me; or $R^{12}$ taken together with $R^{14}$ forms a piperidine ring; $R^{11}$ is H or Me; and $R^{13}$ taken together with $R^{12}$ forms a piperidine ring.

In certain embodiments, -Q-X—Y— is

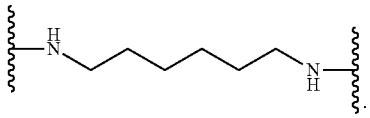 [SMILES: *NCCCCCCN*]

In certain embodiments, -Q-X—Y— is

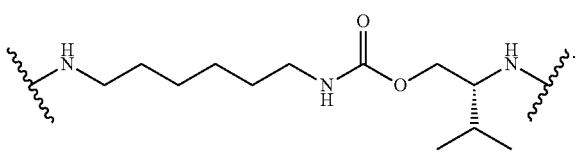 [SMILES: *NCCCCCCNC(=O)OC[C@H](N*)C(C)C]

In certain embodiments, -Q-X—Y— is

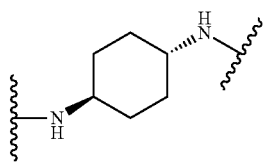

In certain embodiments, -Q-X—Y— is

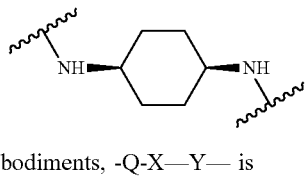

In certain embodiments, -Q-X—Y— is

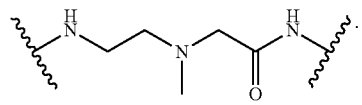 [SMILES: *NCCN(C)CC(=O)N*]

In certain embodiments, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

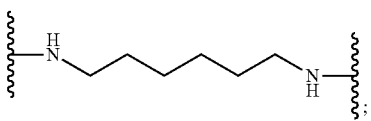 [SMILES: *NCCCCCCN*]

and W is

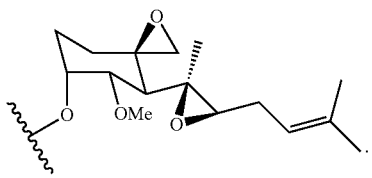

In certain embodiments, $R_4$ and $R_5$ are methyl; $R_6$ is 2-hydroxypropyl; Z is —NH-$AA_1$-$AA_2$-$AA_3$-$AA_4$-$AA_5$-

AA$_6$-C(O)-Q-X—Y—C(O)—W; AA$_1$ is glycine; AA$_2$ is a bond; AA$_3$ is a bond; AA$_4$ is phenylalanine; AA$_5$ is leucine; AA$_6$ is glycine; -Q-X—Y— is

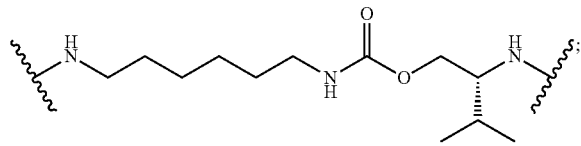 [SMILES: *NCCCCCCNC(=O)OC[C@H](N*)C(C)C]

and W is

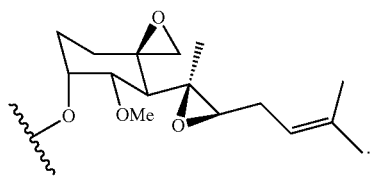

In certain embodiments, R$_4$ and R$_5$ are methyl; R$_6$ is 2-hydroxypropyl; Z is —NH-AA$_1$-AA$_2$-AA$_3$-AA$_4$-AA$_5$-AA$_6$-C(O)-Q-X—Y—C(O)—W; AA$_1$ is glycine; AA$_2$ is a bond; AA$_3$ is a bond; AA$_4$ is phenylalanine; AA$_5$ is leucine; AA$_6$ is glycine; -Q-X—Y— is

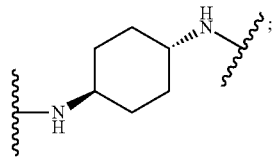 [SMILES: *N[C@H]1CC[C@H](N*)CC1]

and W is

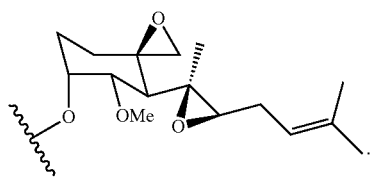

In certain embodiments, -Q-X—Y— is a self-immolating linker that releases the MetAP2 inhibitor in the form of a carbamate derivative as shown in the scheme below:

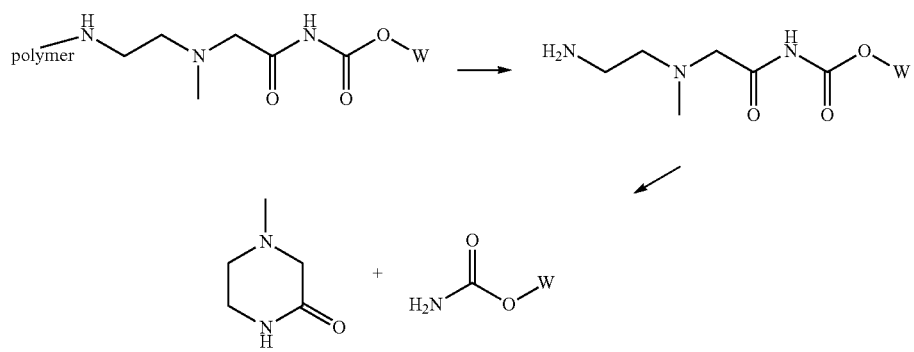

Another aspect of the present invention provides conjugates with linkers having the structure: Z-Q-X—Y—C(O)—W; wherein, independently for each occurrence, Z is H$_2$N-AA$_2$-AA$_3$-AA$_4$-AA$_5$-AA$_6$-C(O)— or H; AA$_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine; AA$_5$ is a bond, alanine, cysteine, glycine, isoleucine, leucine, methionine, phenylalanine, valine, tryptophan, or; AA$_6$ is alanine, asparagine, citrulline, glutamine, glycine, leucine, methionine, phenylalanine, serine, threonine, tryptophan, tyrosine, valine or H$_2$N(CH$_2$)mCO$_2$H, wherein m is 2, 3, 4 or 5; Q is NR, O, or S; X is M-(C(R)$_2$)$_p$-M-J-M-(C(R)$_2$)$_p$-M-V; M is a bond, or C(O); J is a bond, or ((CH$_2$)$_q$Q)$_r$, C$_5$-C$_8$ cycloalkyl, aryl, heteroaryl, NR, O, or S; Y is NR, O, or S; R is H or alkyl; V is a bond or

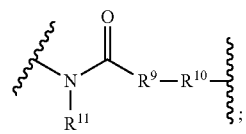

R$^9$ is alkyl, aryl, aralkyl, or a bond; or R$^9$ taken together with Y forms a heterocyclic ring; R$^{10}$ is amido or a bond; R$^{11}$ is H or alkyl; W is a MetAP2 inhibitor moiety; p is 0 to 20; q is 2 or 3; and r is 1, 2, 3, 4, 5, or 6.

In certain embodiments, Z is H$_2$N-AA$_5$-AA$_6$-C(O)—. In certain embodiments, AA$_5$ is alanine, cysteine, glycine, isoleucine, leucine, methionine, phenylalanine, valine, tryptophan, or tyrosine and AA$_6$ is glycine. In certain embodiments, AA$_5$ is leucine and AA$_6$ is glycine. In certain embodiments, AA$_5$ is valine and AA$_6$ is glycine. In certain embodiments, AA$_5$ is phenylalanine and AA$_6$ is glycine. In certain embodiments, AA$_5$ is glycine and AA$_6$ is glycine. In certain embodiments, AA$_5$ is not valine.

In other embodiments, Z is H$_2$N-AA$_3$-AA$_4$-AA$_5$-AA$_6$-C(O)—. In certain embodiments, AA$_5$ is alanine, cysteine, glycine, isoleucine, leucine, methionine, phenylalanine, valine, tryptophan, or tyrosine and each of AA$_3$, AA$_4$, or AA$_6$ is glycine. In certain embodiments, AA$_5$ is leucine and each of AA$_3$, AA$_4$, or AA$_6$ is glycine. In certain embodiments, AA$_5$ is valine and each of AA$_3$, AA$_4$, or AA$_6$ is glycine. In certain embodiments, AA$_5$ is phenylalanine and each of AA$_3$, AA$_4$, or AA$_6$ is glycine. In certain embodiments, AA$_3$ is glycine, AA$_4$ is phenylalanine, AA$_5$ is leucine and AA$_6$ is glycine. In certain embodiments, each of AA$_3$, AA$_4$, AA$_5$ and AA$_6$ is glycine. In certain embodiments, AA$_5$ is not valine.

In certain embodiments, Z is H. In other embodiments, Z is H$_2$N-AA$_6$-C(O)—. In certain embodiments, AA$_6$ is glycine.

In certain embodiments, Q is NR. In certain embodiments, M is a bond. In certain embodiments, J is a bond. In certain embodiments, Y is NR.

In certain embodiments, W is:

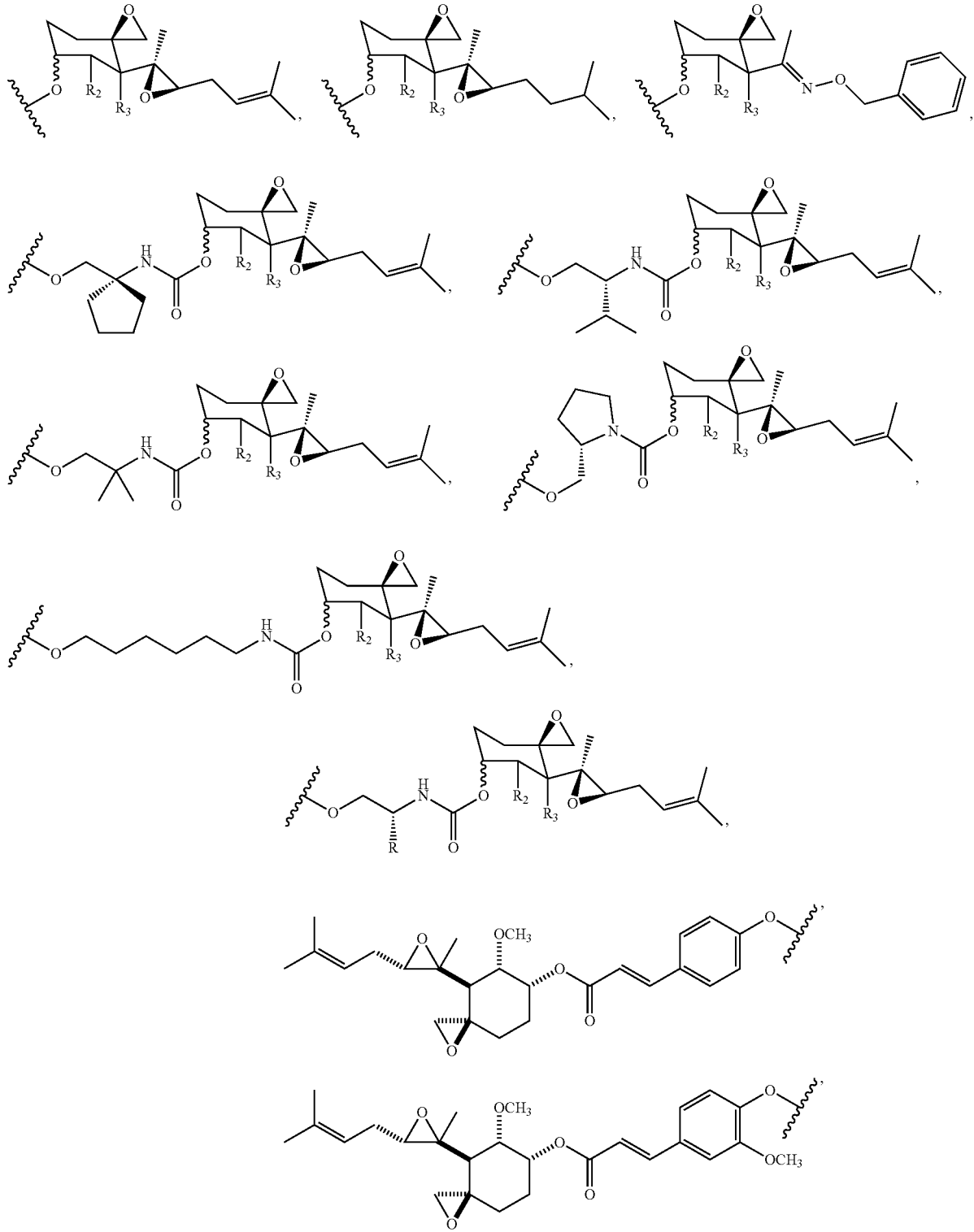

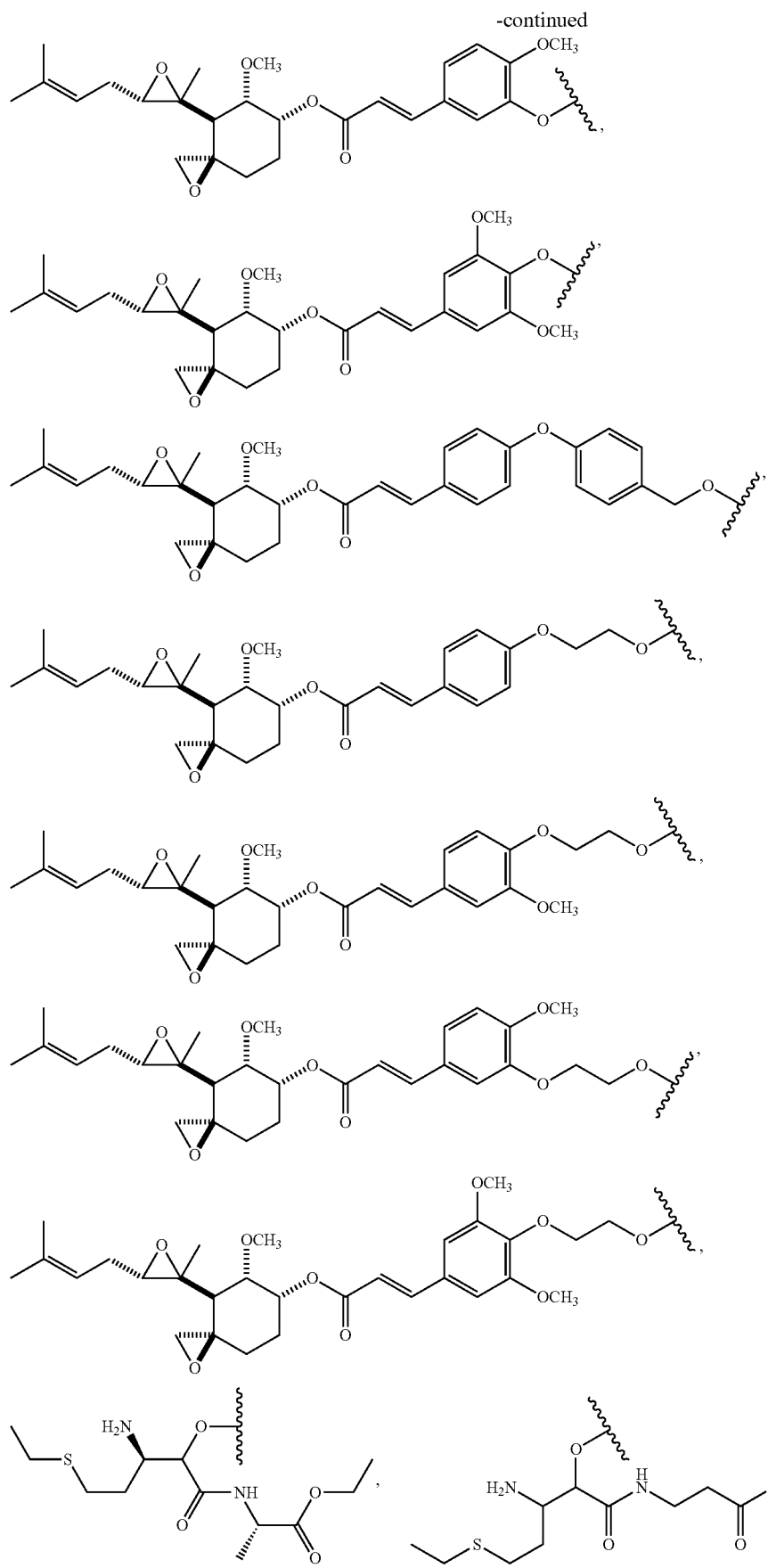

31
32
-continued
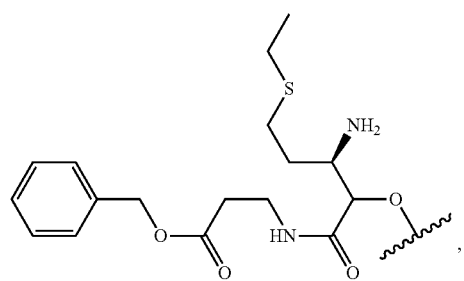
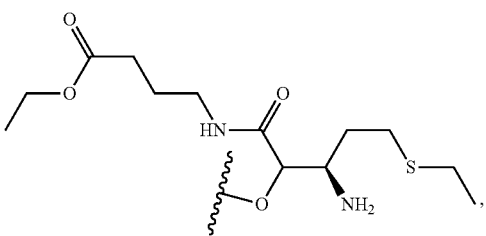
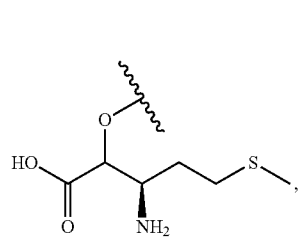
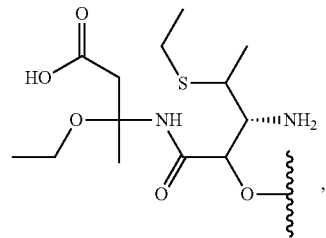
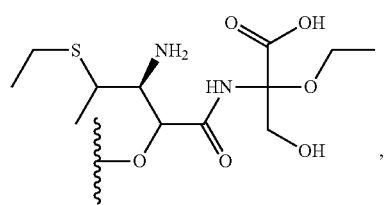
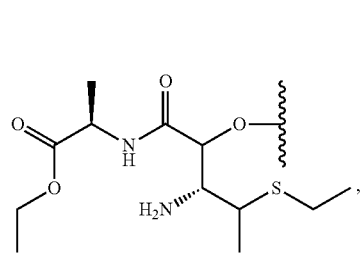
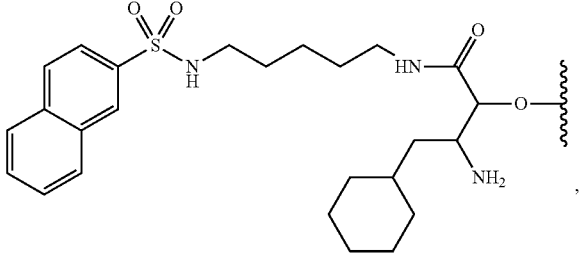
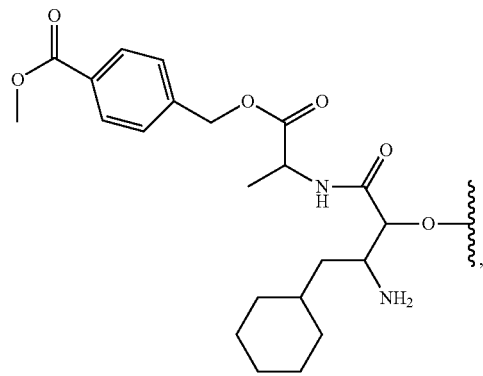
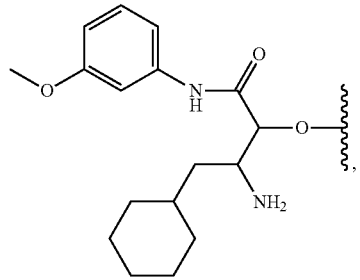
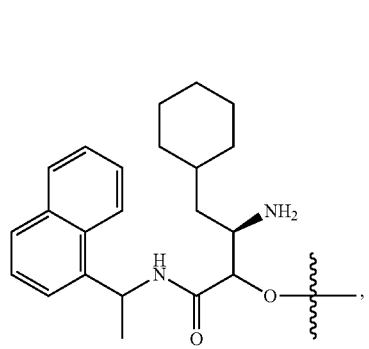
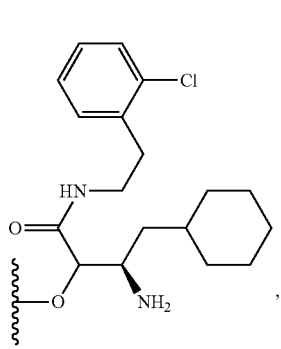
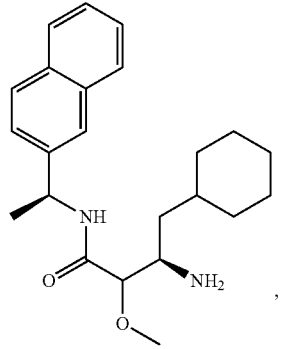

33 34
-continued
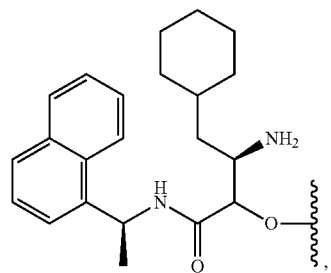
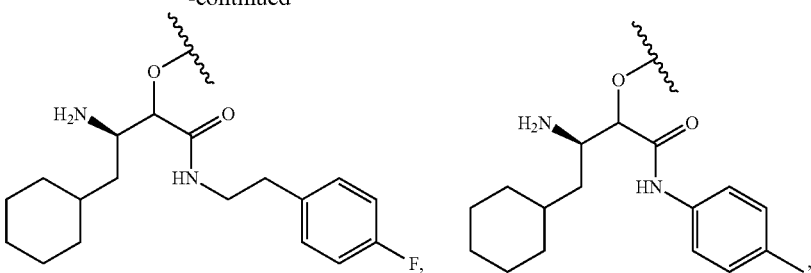
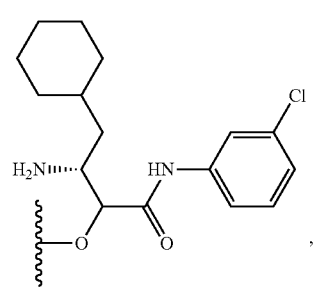
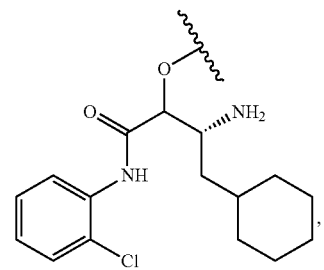
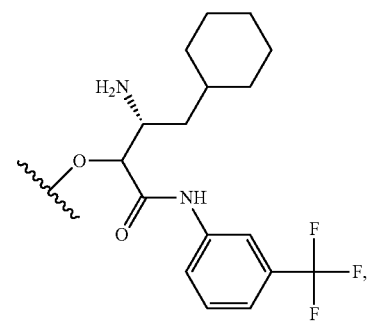
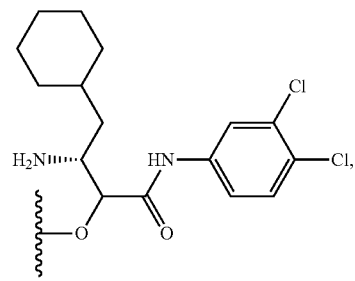
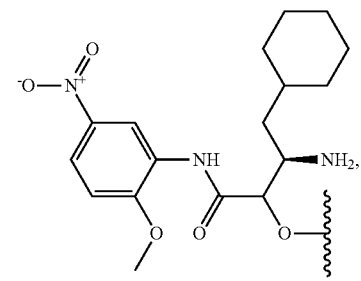
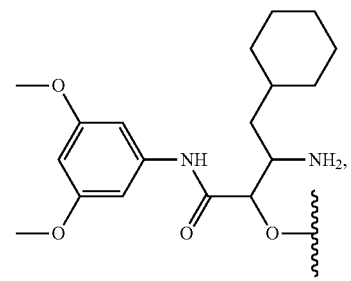
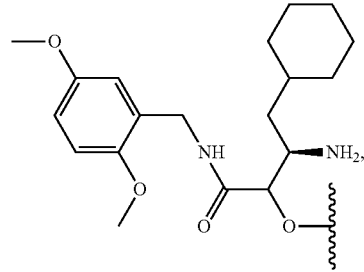
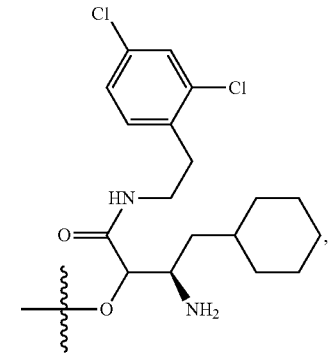
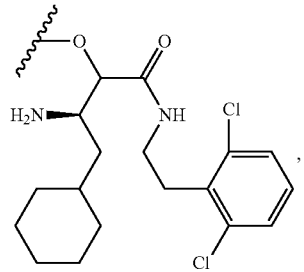
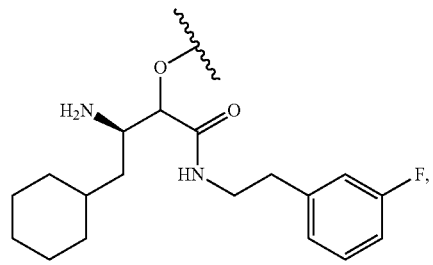
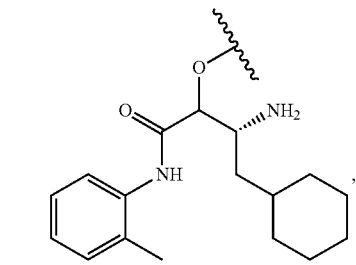
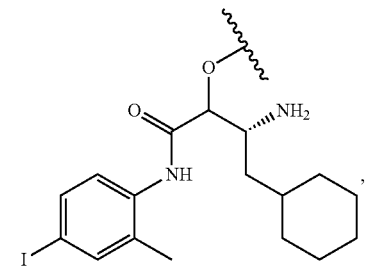

-continued
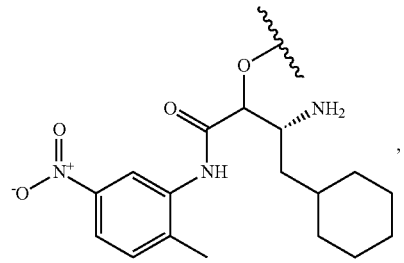 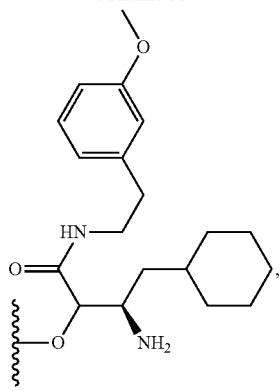 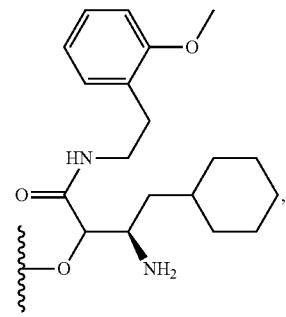
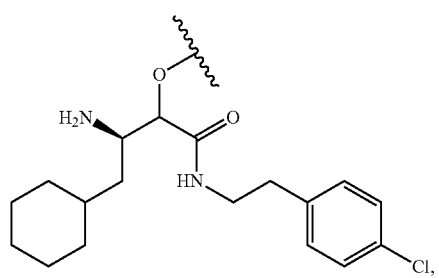 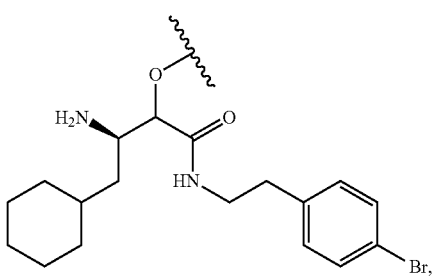
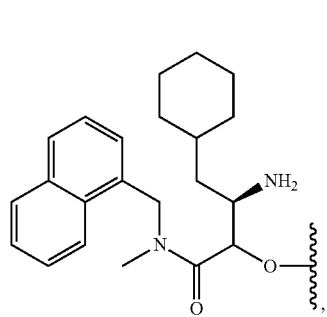 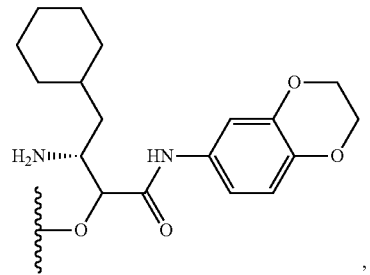 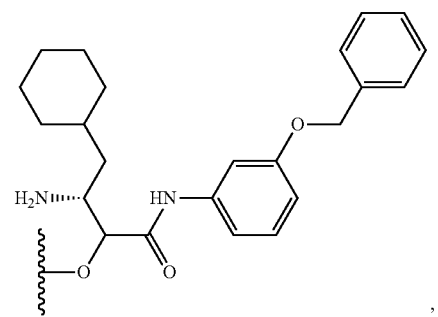
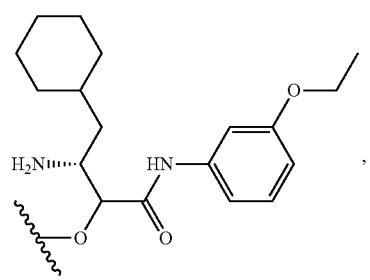 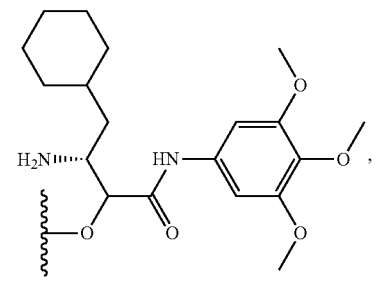 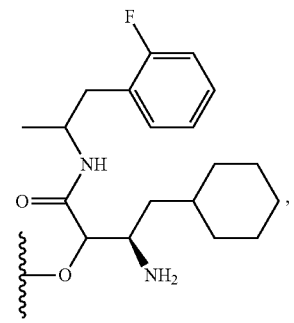
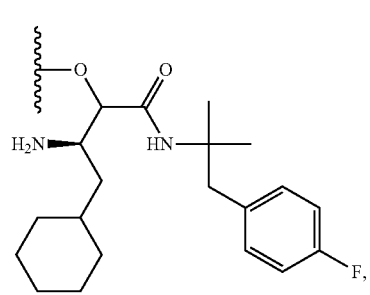 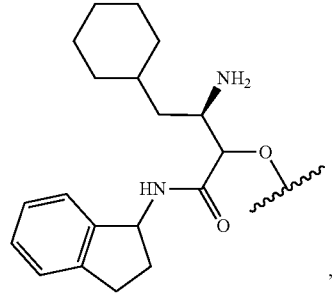 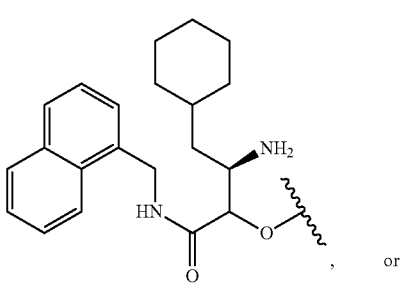 or

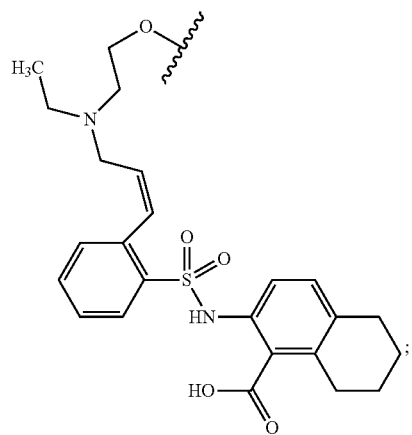
wherein $R_2$ is —OH or methoxy; and $R_3$ is H, —OH or methoxy.
In certain embodiments, W is
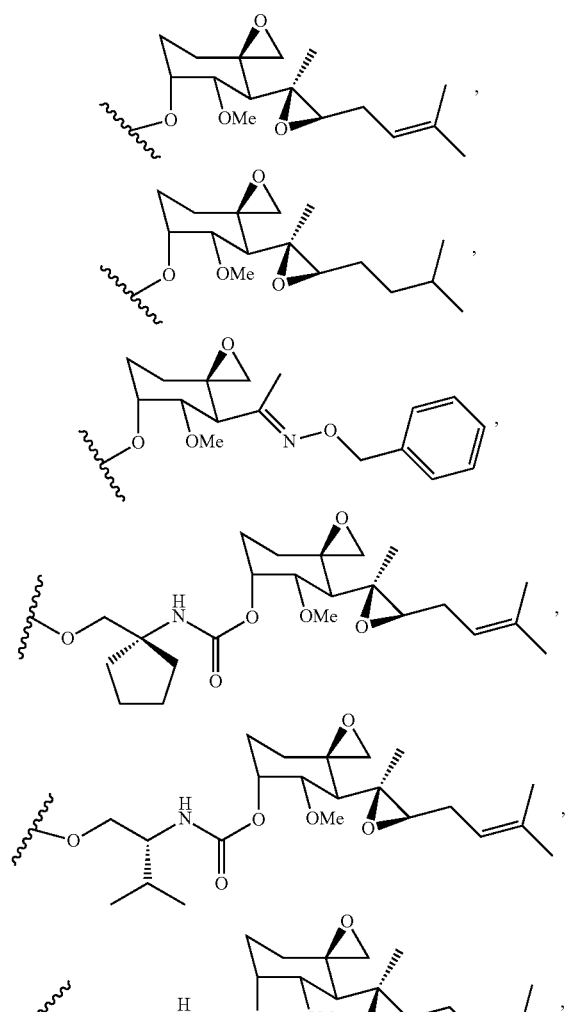
-continued
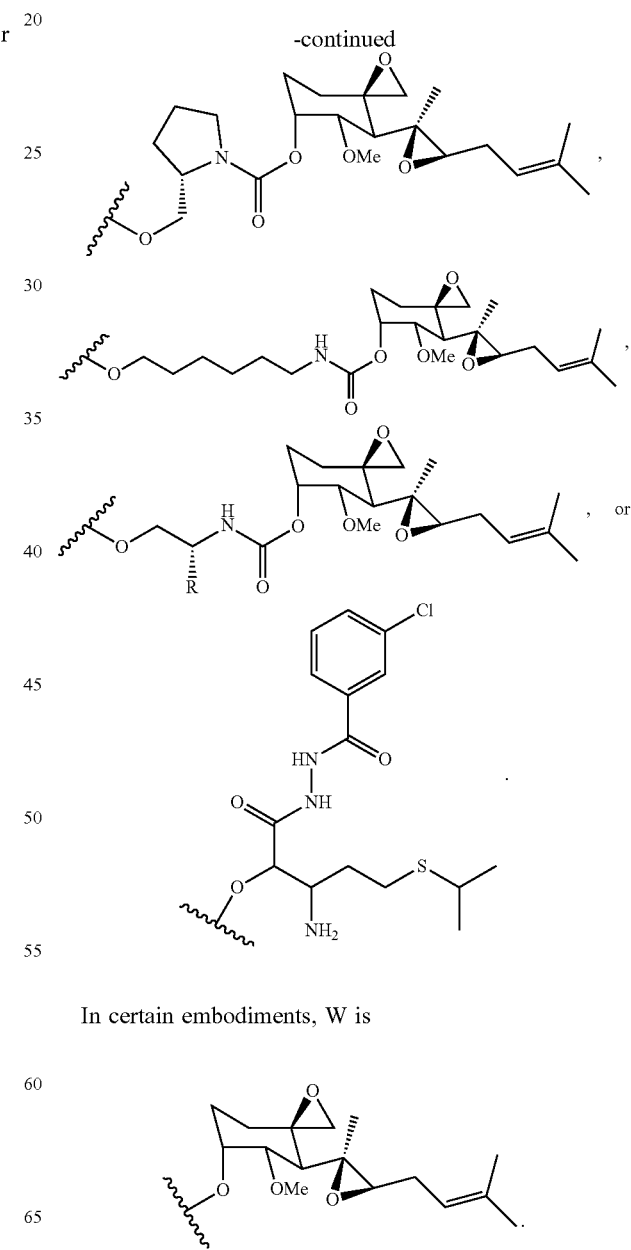
In certain embodiments, W is In certain embodiments, -Q-X—Y— is
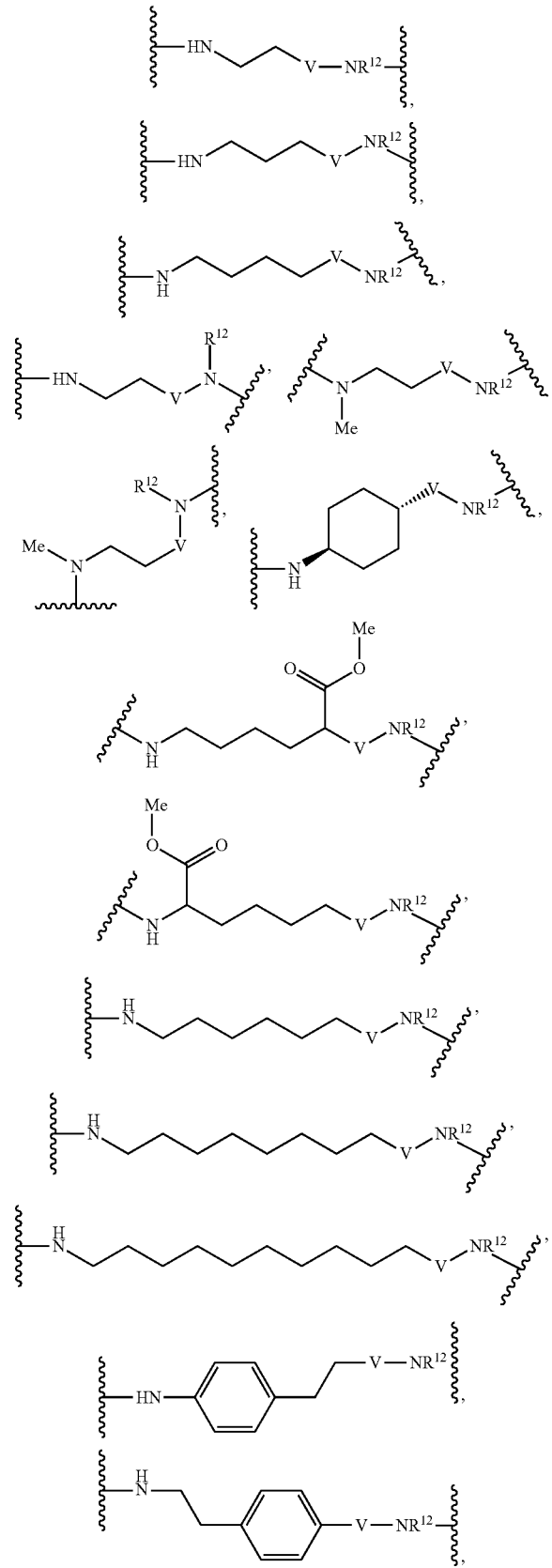
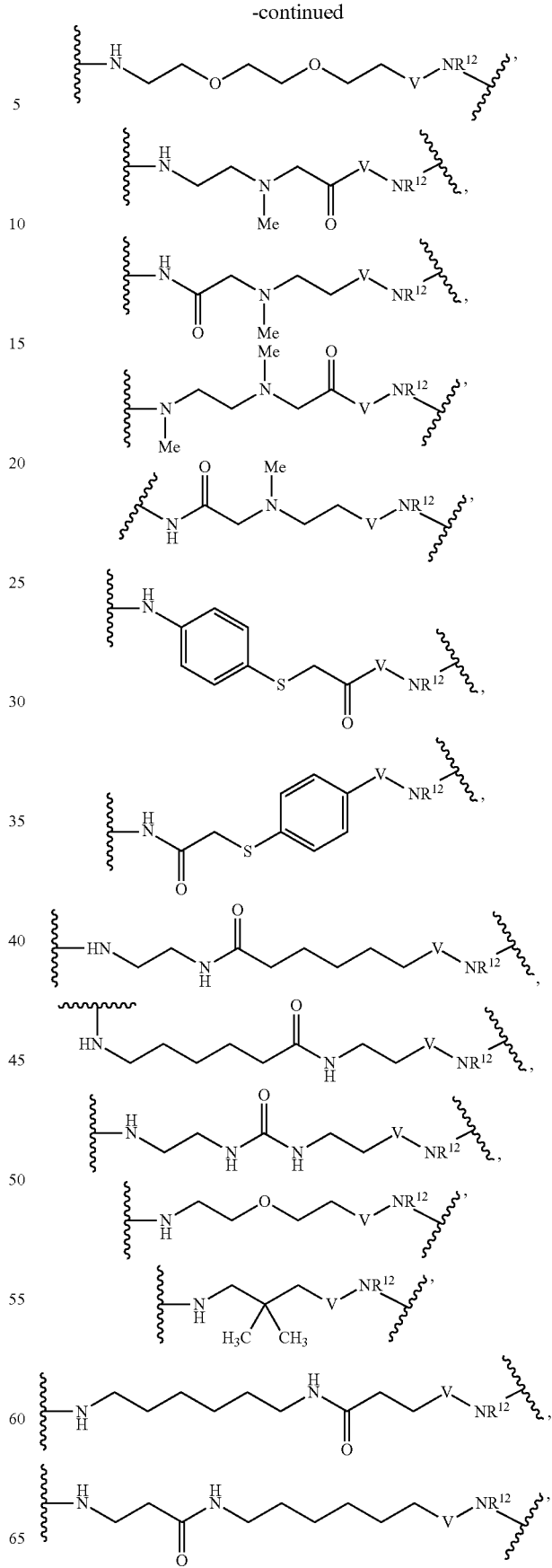

-continued

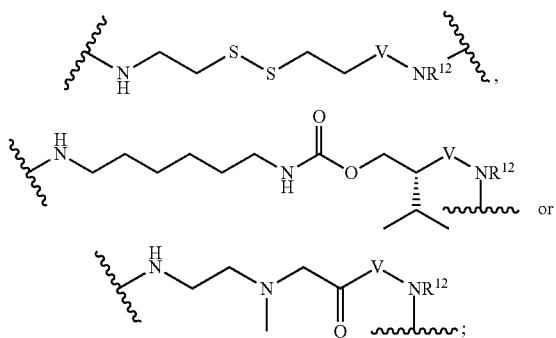

V is:

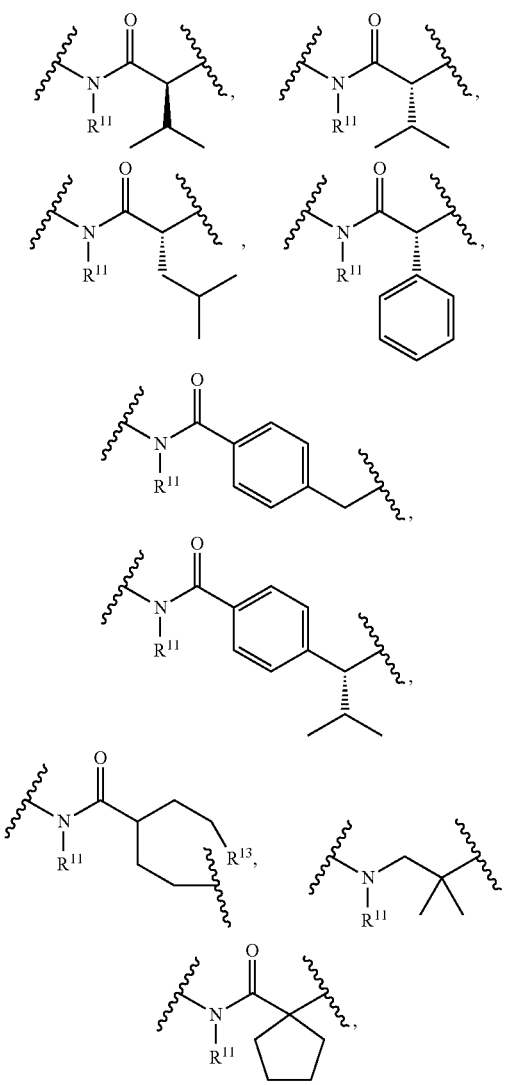

or a bond; $R^{12}$ is H or Me; or $R^{12}$ taken together with $R^{14}$ forms a piperidine ring; $R^{11}$ is H or Me; and $R^{13}$ taken together with $R^{12}$ forms a piperidine ring.

In certain embodiments, Z is $H_2N$-$AA_5$-$AA_6$-C(O)—; $AA_5$ is leucine and $AA_6$ is glycine; Q-X—Y is

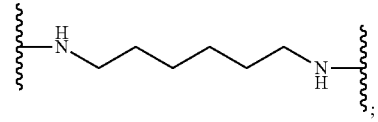

and W is

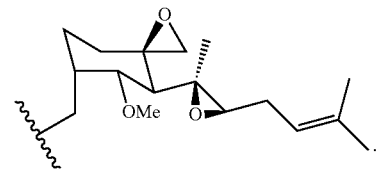

In certain embodiments, Z is $H_2N$-$AA_5$-$AA_6$-C(O)—; $AA_5$ is valine and $AA_6$ is glycine; Q-X—Y is

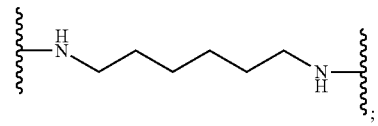 [SMILES: *NCCCCCCN* ; ";"]

and W is

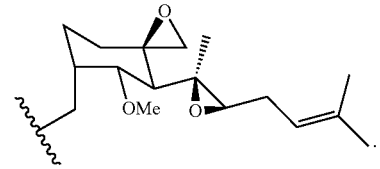

In certain embodiments, Z is $H_2N$-$AA_5$-$AA_6$-C(O)—; $AA_5$ is phenylalanine and $AA_6$ is glycine; Q-X—Y is

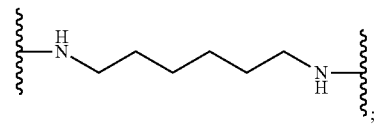

and W is

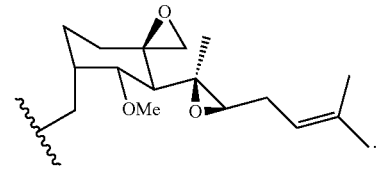

In certain embodiments, Z is $H_2N$-$AA_5$-$AA_6$-C(O)—; $AA_5$ is glycine and $AA_6$ is glycine; Q-X—Y is

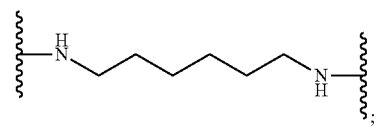 [SMILES: *NCCCCCCN* ; ";"]

and W is

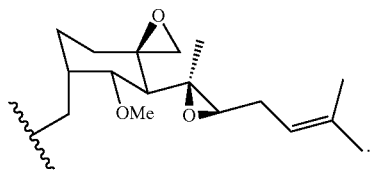

In certain embodiments, Z is H$_2$N-AA$_3$-AA$_4$-AA$_5$-AA$_6$-C(O)—; AA$_5$ is leucine and each of AA$_3$, AA$_4$, or AA$_6$ is glycine; Q-X—Y is

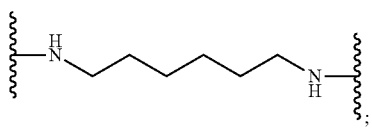 [SMILES: *NCCCCCCN* ; ";"]

and W is

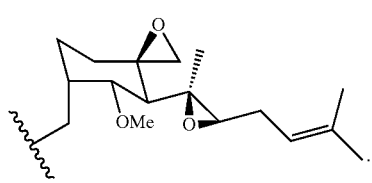

In certain embodiments, Z is H$_2$N-AA$_3$-AA$_4$-AA$_5$-AA$_6$-C(O)—; AA$_5$ is valine and each of AA$_3$, AA$_4$, or AA$_6$ is glycine; Q-X—Y is

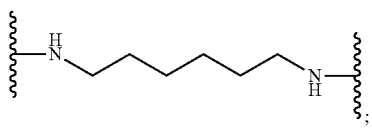 [SMILES: *NCCCCCCN* ; ";"]

and W is

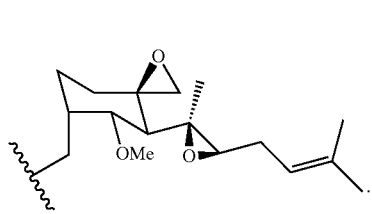

In certain embodiments, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

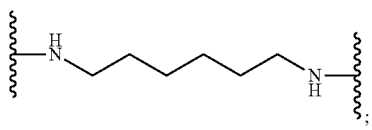

and W is

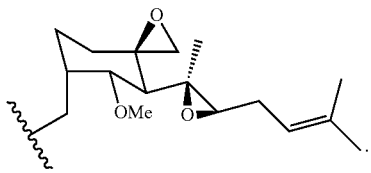

In certain embodiments, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

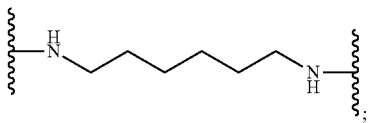 [SMILES: *NCCCCCCN* ; ";"]

and W is

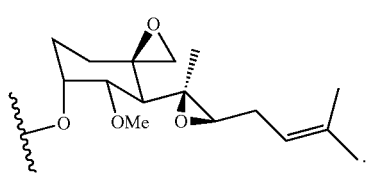

In certain embodiments, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

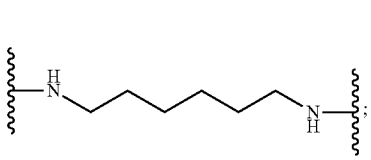 [SMILES: *NCCCCCCN*]

and W is

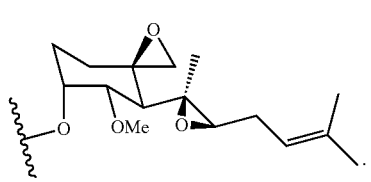

In certain embodiments, Z is H$_2$N-AA$_6$-C(O)—; AA$_6$ is glycine; Q-X—Y is

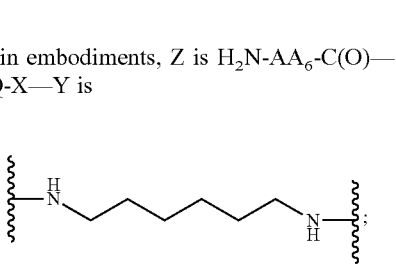

and W is

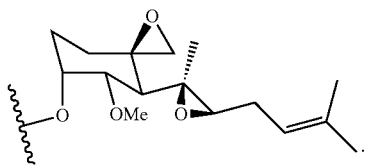

In certain embodiments, Z is H; Q-X—Y is

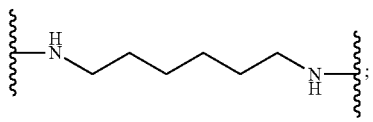 [SMILES: *NCCCCCCN*]

and W is

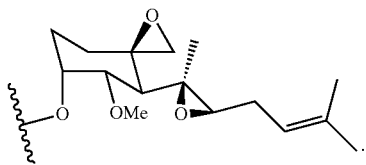

In certain embodiments, Z is H$_2$N-AA$_5$-AA$_6$-C(O)—; AA$_5$ is leucine and AA$_6$ is glycine; Q-X—Y is

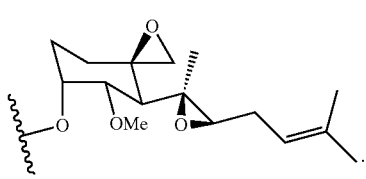

and W is

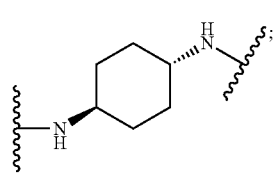 [SMILES: *N[C@H]1CC[C@H](N*)CC1]

In certain embodiments, Z is H$_2$N-AA$_5$-AA$_6$-C(O)—; AA$_5$ is valine and AA$_6$ is glycine; Q-X—Y is and W is

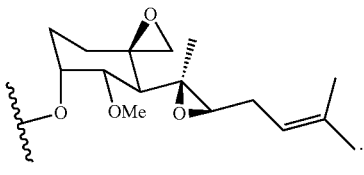

In certain embodiments, Z is H$_2$N-AA$_5$-AA$_6$-C(O)—; AA$_5$ is phenylalanine and AA$_6$ is glycine; Q-X—Y is

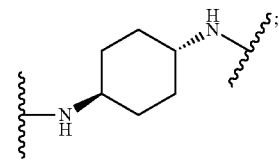 [SMILES: *N[C@H]1CC[C@H](N*)CC1]

and W is

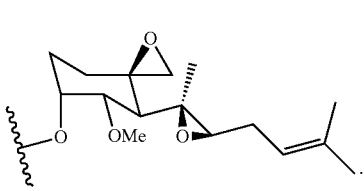

In certain embodiments, Z is H$_2$N-AA$_5$-AA$_6$-C(O)—; AA$_5$ is glycine and AA$_6$ is glycine; Q-X—Y is

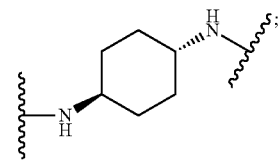 [SMILES: *N[C@H]1CC[C@H](N*)CC1]

and W is

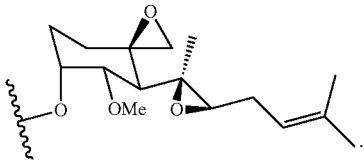

In certain embodiments, Z is H$_2$N-AA$_3$-AA$_4$-AA$_5$-AA$_6$-C(O)—; AA$_5$ is leucine and each of AA$_3$, AA$_4$, or AA$_6$ is glycine; Q-X—Y is

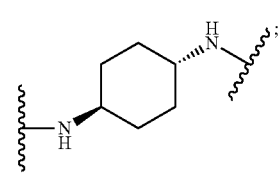 [SMILES: *N[C@H]1CC[C@H](N*)CC1]

and W is

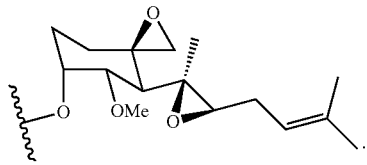

In certain embodiments, Z is H₂N-AA₃-AA₄-AA₅-AA₆-C(O)—; AA₅ is valine and each of AA₃, AA₄, or AA₆ is glycine; Q-X—Y is

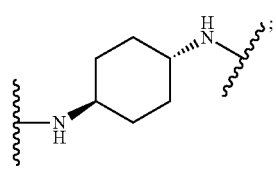 [SMILES: *N[C@H]1CC[C@H](N*)CC1]

and W is

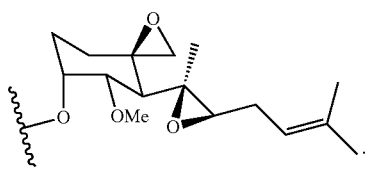

In certain embodiments, Z is H₂N-AA₃-AA₄-AA₅-AA₆-C(O)—; AA₅ is phenylalanine and each of AA₃, AA₄, or AA₆ is glycine; Q-X—Y is

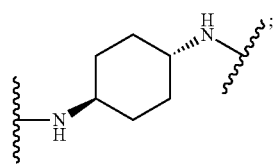 [SMILES: *N[C@H]1CC[C@H](N*)CC1]

and W is

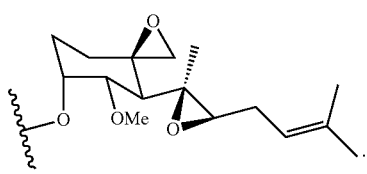

In certain embodiments, Z is H₂N-AA₃-AA₄-AA₅-AA₆-C(O)—; AA₃ is glycine, AA₄ is phenylalanine, AA₅ is leucine and AA₆ is glycine; Q-X—Y is

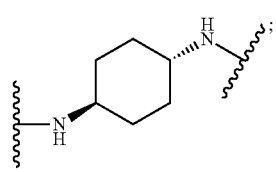 [SMILES: *N[C@H]1CC[C@H](N*)CC1]

and W is

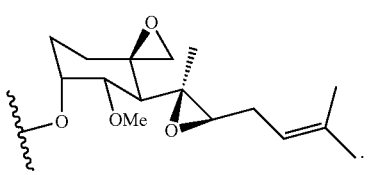

In certain embodiments, Z is H₂N-AA₃-AA₄-AA₅-AA₆-C(O)—; each of AA₃, AA₄, AA₅ and AA₆ is glycine; Q-X—Y is

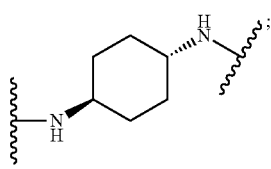 [SMILES: *N[C@H]1CC[C@H](N*)CC1]

and W is

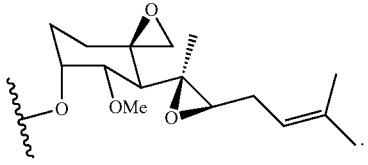

In certain embodiments, Z is H₂N-AA₆-C(O)—; AA₆ is glycine; Q-X—Y is

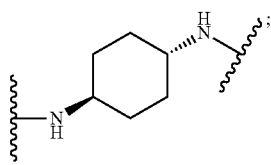 [SMILES: *N[C@H]1CC[C@H](N*)CC1]

and W is

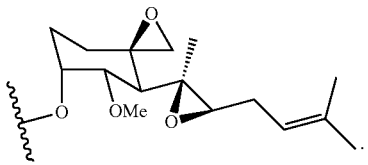

In certain embodiments, Z is H; Q-X—Y is

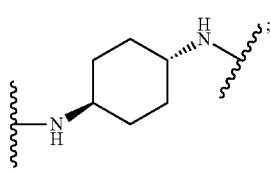 [SMILES: *N[C@H]1CC[C@H](N*)CC1]

and W is

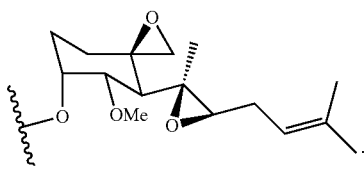

In certain embodiments, Z is $H_2N\text{-}AA_5\text{-}AA_6\text{-}C(O)\text{—}$; $AA_5$ is leucine and $AA_6$ is glycine; Q-X—Y is

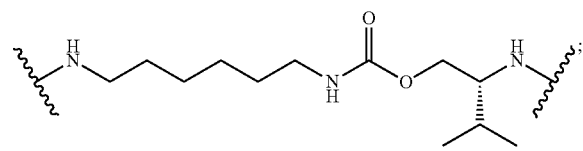 [SMILES: *NCCCCCCNC(=O)OC[C@H](N*)C(C)C]

and W is

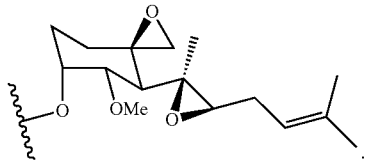

In certain embodiments, Z is $H_2N\text{-}AA_5\text{-}AA_6\text{-}C(O)\text{—}$; $AA_5$ is valine and $AA_6$ is glycine; Q-X—Y is

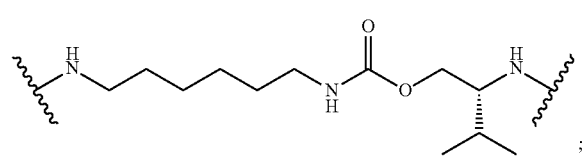 [SMILES: *NCCCCCCNC(=O)OC[C@H](N*)C(C)C]

and W is

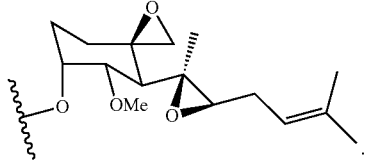

In certain embodiments, Z is $H_2N\text{-}AA_5\text{-}AA_6\text{-}C(O)\text{—}$; $AA_5$ is phenylalanine and $AA_6$ is glycine; Q-X—Y is

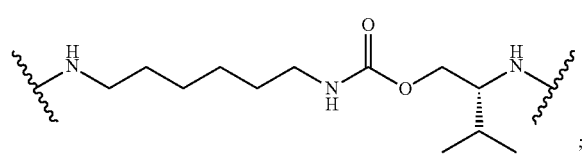 [SMILES: *NCCCCCCNC(=O)OC[C@H](N*)C(C)C]

and W is

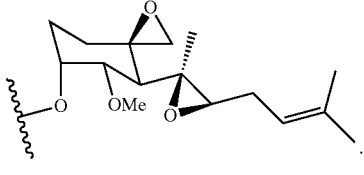

In certain embodiments, Z is $H_2N\text{-}AA_5\text{-}AA_6\text{-}C(O)\text{—}$; $AA_5$ is glycine and $AA_6$ is glycine; Q-X—Y is

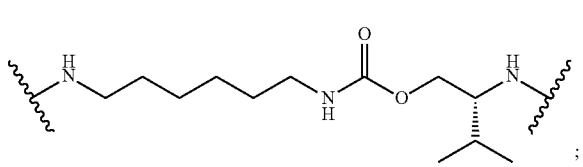 [SMILES: *NCCCCCCNC(=O)OC[C@H](N*)C(C)C]

and W is

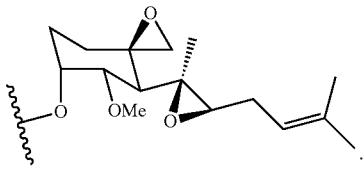

In certain embodiments, Z is $H_2N\text{-}AA_3\text{-}AA_4\text{-}AA_5\text{-}AA_6\text{-}C(O)\text{—}$; $AA_5$ is leucine and each of $AA_3$, $AA_4$, or $AA_6$ is glycine; Q-X—Y is

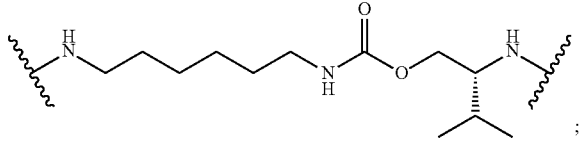 [SMILES: *NCCCCCCNC(=O)OC[C@H](N*)C(C)C]

and W is

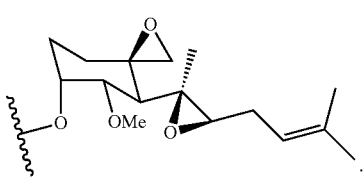

In certain embodiments, Z is $H_2N\text{-}AA_3\text{-}AA_4\text{-}AA_5\text{-}AA_6\text{-}C(O)\text{—}$; $AA_5$ is valine and each of $AA_3$, $AA_4$, or $AA_6$ is glycine; Q-X—Y is

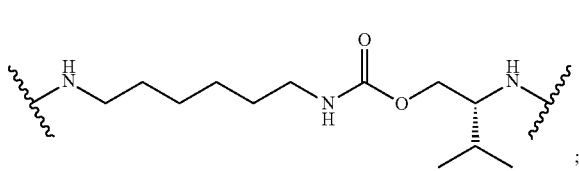 [SMILES: *NCCCCCCNC(=O)OC[C@H](N*)C(C)C]

and W is

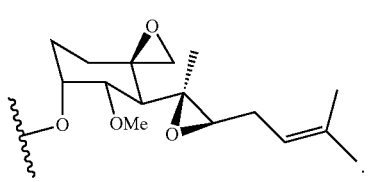

In certain embodiments, Z is H$_2$N-AA$_3$-AA$_4$-AA$_5$-AA$_6$-C(O)—; AA$_5$ is phenylalanine and each of AA$_3$, AA$_4$, or AA$_6$ is glycine; Q-X—Y is

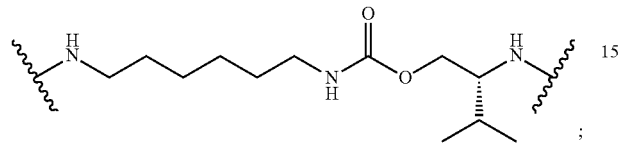

and W is

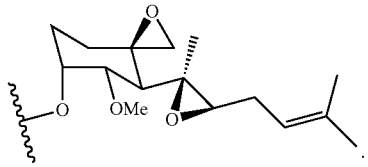

In certain embodiments, Z is H$_2$N-AA$_3$-AA$_4$-AA$_5$-AA$_6$-C(O)—; AA$_3$ is glycine, AA$_4$ is phenylalanine, AA$_5$ is leucine and AA$_6$ is glycine; Q-X—Y is

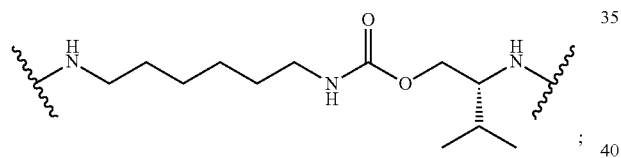

and W is

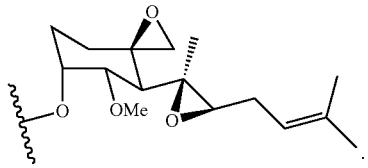

In certain embodiments, Z is H$_2$N-AA$_3$-AA$_4$-AA$_5$-AA$_6$-C(O)—; each of AA$_3$, AA$_4$, AA$_5$ and AA$_6$ is glycine; Q-X—Y is

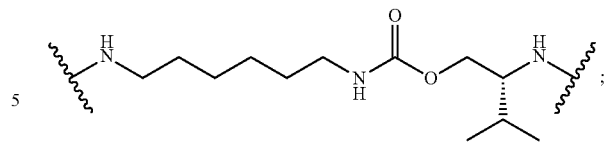

and W is

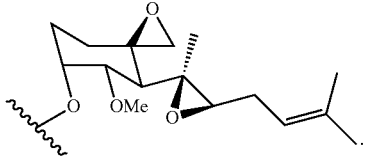

In certain embodiments, Z is H$_2$N-AA$_6$-C(O)—; AA$_6$ is glycine; Q-X—Y is

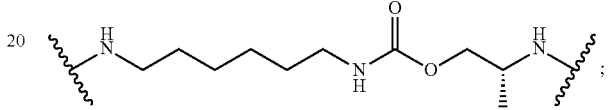

and W is

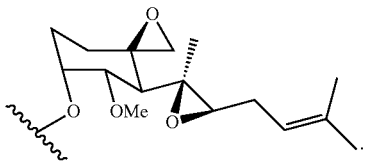

In certain embodiments, Z is H; Q-X—Y is

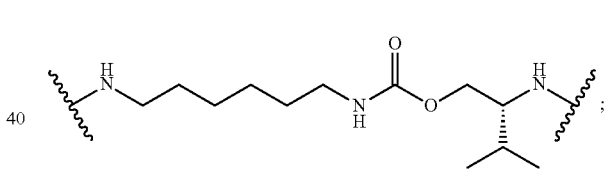

and W is

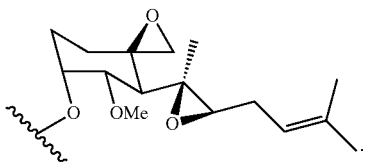

Other active moieties that may be modified to be used in conjugates of the invention include the following structures:

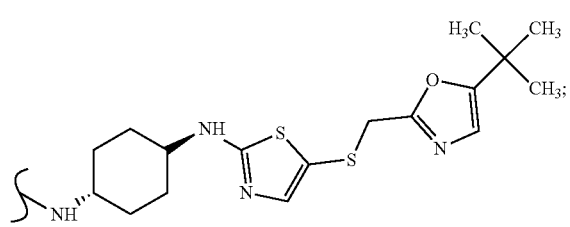

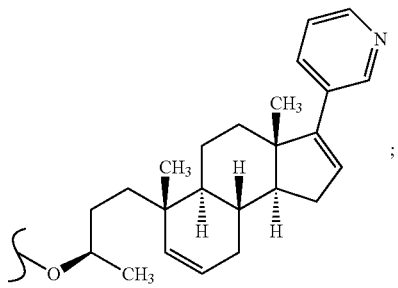

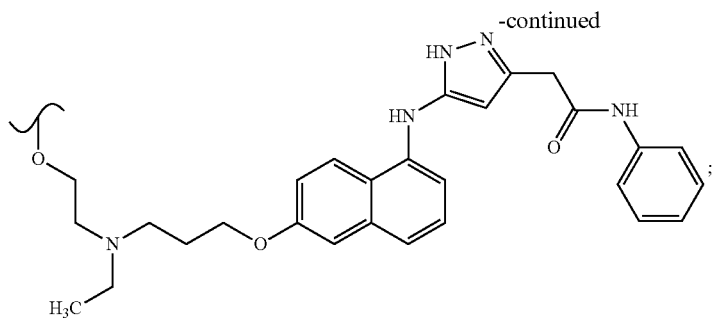 and 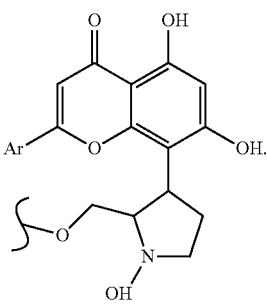

In certain embodiments, the active moiety is an anti-obesity compound. In other embodiments, the active moiety is a molecule that inhibits methionine aminopeptidase-2 (MetAP2), such as fumagillin, fumagillol, or an analog, derivative, salt or ester thereof. Further exemplary MetAP2 inhibitors have been described in U.S. Pat. No. 6,242,494 to Craig et al, U.S. Pat. No. 6,063,812 to Hong et al., U.S. Pat. No. 6,887,863 to Craig et al., U.S. Pat. No. 7,030,262 to BaMaung et al., U.S. Pat. No. 7,491,718 to Comess et al., each of which is incorporated by reference in its entirety. Additional exemplary MetAP2 inhibitors have been described in Wang et al. "Correlation of tumor growth suppression and methionine aminopeptidase-2 activity blockade using an orally active inhibitor," PNAS 105(6) 1838-1843 (2008); Lee at al. "Design, Synthesis, and Antiangiogenic Effects of a Series of Potent Novel Fumagillin Analogues," Chem. Pharm. Bull. 55(7) 1024-1029 (2007); Jeong et al. "Total synthesis and antiangiogenic activity of cyclopentane analogues of fumagillol," Bioorganic and Medicinal Chemistry Letters 15, 3580-3583 (2005); Arico-Muendel et al. "Carbamate Analogues of Fumagillin as Potent, Targeted Inhibitors of Methionine Aminopeptidase-2," J. Med. Chem. 52, 8047-8056 (2009); and International Publication No. WO 2010/003475 to Heinrich et al.

Fumagillin is a small molecule which has been used as an antimicrobial and antiprotozoal agent. Its physiochemical properties and method of production are well known (See U.S. Pat. No. 2,803,586 and Turner, J. R. et al., The Stereochemistry of Fumagillin, Proc. Natl. Acad. Sci. 48, 733-735 (1962)). The fermentation product, fumagillin, may be hydrolyzed to yield the alcohol fumagillol which in turn may be converted into various derivatives including carbamoylfumagillol, MW 325. The synthesis and preparation of carbamoylfumagillol and some small molecule derivatives are described in U.S. Pat. No. 5,166,172.

Fumagillin and related compounds are believed to exert their biological effects through the inhibition of MetAP2. This enzyme removes N-terminal methionine from nascent cellular proteins. (See Tucker, L. A., et al. "Ectopic Expression of Methionine Aminopeptidase-2 Causes Cell Transformation and Stimulates Proliferation", Oncogene 27, 3967 (2008).)

Carbamoylfumagillol and derivatives as well as other inhibitors of MetAP2 have shown therapeutic benefits in preclinical and clinical studies. These compounds inhibit cell proliferation and angiogenesis as described in U.S. Pat. No. 5,166,172. Fumagillin analogs or derivatives, such as CKD-732 and PI-2458, are well studied in various systems as described in detail in Bernier et al., "Fumagillin class inhibitors of methionine aminopeptidase-2" Drugs of the Future 30(5): 497-508, 2005.

The anti-obesity effects of fumagillin and its analogs are well-known. Rupnick et al. "Adipose tissue mass can be regulated through the vasculature" PNAS 99, 10730-10735, 2002 describes weight loss in ob/ob mice with daily doses of TNP-470 ranging from 2.5 mg/kg to 10 mg/kg. Brakenhielm describes prevention of obesity at TNP-470 doses of 15 or 20 mg/kg every other day, "The Angiogenesis Inhibitor, TNP-470, Prevents Diet-Induced and Genetic Obesity in Mice" Circulation Research 94: 1579-1588, 2004. Kim, et al., in the "Assessment of the anti-obesity effects of the TNP-470 analog, CKD-732" J Molecular Endocrinology 38, 455-465, 2007 describe weight loss in C57BL/6J mice and SD rats at doses of 5 mg/kg/day. Lijnen et al. "Fumagillin reduces adipose tissue formation in murine models of nutritionally induced obesity" Obesity 12, 2241-2246, 2010 describes oral delivery of 1 mg/kg fumagillin daily resulting in weight loss in C57BL/6 mice.

One of these derivatives, chloroacetylcarbamoylfumagillol (TNP-470) has been extensively studied. (See H. Mann-Steinberg, et al., "TNP-470: The Resurrection of the First Synthetic Angiogenesis Inhibitor", Chapter 35 in Folkman and Figg, Angiogenesis: An Integrative Approach from Science to Medicine, Springer NY (2008).) TNP-470 has shown activity against many cancers including lung cancer, cervical cancer, ovarian cancer, breast cancer and colon cancer. Because of dose-limiting neurotoxicity, TNP-470 has been tested using multiple dosing regimens, but these attempts to limit its toxicity have been unsuccessful. Thus, TNP-470 has been found to be too toxic for human use. TNP-470 has a short half-life and requires extended intravenous administration for therapeutic use. A metabolite of TNP-470, carbamoylfumagillol has a half-life of 12 minutes in man. (See Herbst et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", Journal of Clinical Oncology 20(22) 4440-4447 (2002). In addition, fumagillin and its derivatives are hydrophobic and difficult to formulate.

Despite the known usefulness of fumagillin derivatives, they have not been used successfully as treatments because of the failure to overcome the problems of the low water solubility, short half-life values, and neurotoxic side-effects of these compounds. TNP-470 in combination with paclitaxel was determined to have an MTD of 60 mg/m2 dosed three times per week based on the previously observed dose limiting neuropsychiatric toxicities Herbst et al., "Safety and pharmacokinetic effects of TNP-470, an angiogenesis inhibitor, combined with paclitaxel in patients with solid tumors: evidence for activity in non-small-cell lung Cancer" Journal of Clinical Oncology 20, 4440-4447, 2002. Similarly Shin et al. "A Phase 1 pharmacokinetic and pharmacodynamics study of CKD-732, an antiangiogenic agent, in patients with refractory solid cancer" Investigational New Drugs 28, 650-658, 2010 reports that the MTD of CKD-732 was 15 mg/m2/day dosed on an every fourth day schedule due to confusion and insomnia. Accordingly, the compounds of the present invention are more potent, show reduced toxicity (less neurotoxic), improved water solubility, more stable, and/or have longer half-life (serum half-life) than presently known fumagillin derivatives.

The phrase "reduced toxicity" as used herein has its ordinary meaning as understood by persons of skill in the art. Merely by way of example, and by no means as a limitation on the meaning of the term, the administration of the fumagillin analog conjugate causes less side effects in open field tests with mice, as compared to the fumagillin analog alone.

The phrase "improved water solubility" has its ordinary meaning as understood by persons of skill in the art. Merely by way of example, and by no means as a limitation on the meaning of the term, the following description of the term is informative: an increased amount of a fumagillin analog will dissolve in water as a result of its covalent incorporation into a conjugate as compared to the amount of the unconjugated fumagillin analog that will dissolve in water alone.

The phrase "longer half-life" has its ordinary meaning as understood by persons of skill in the art. Merely by way of example, and by no means as a limitation on the meaning of the term, the following description of the term is informative: any appreciable increase in the length of time required to deactivate fumagillin conjugate either in vivo or in vitro as compared to the half-life of the fumagillin analog alone either in vivo or in vitro.

Without being bound by any theory, non-enzymatic actions of MetAP2 to suppress activity of extra-cellular signal regulated kinases 1 and 2 (ERK1/2) may be important as may be the binding of eukaryotic initiation factor, eIF, by MetAP2. Cellular responses to MetAP2 inhibition reflective of potential ERK-related processes may include suppression of sterol regulatory element binding protein (SREBP) activity, leading to reduced lipid and cholesterol biosynthesis. Interesting, changes in the expression patterns of hepatic and adipose tissue genes after prolonged (approximately 9 months) fumagillin exposure suggest that MetAP2 inhibition also may alter the relative abundance of factors involved in inflammation, consistent with reduced ERK-dependent cellular processes. The putative mechanism of MetAP2 inhibition leading to mobilization of adipose depot and catabolism of free fatty acids as energy source by the body is supported by changes in plasma β-hydroxybutyrate, adiponectin, leptin, and FGF21 observed in previous studies. Elevation in the levels of key catabolic hormones adiponectin and FGF21, coupled with the appearance of ketone bodies β-hydroxybutyrate), suggest MetAP2 inhibition with the conjugated or modified fumagillin, fumagillol, or an analog, derivative, salt or ester thereof compounds of the present invention stimulates energy expenditure, fat utilization and lipid excretion. The reduction in leptin observed in previous studies and the studies provided herein is also consistent with a decrease in total adipose tissue and negative energy balance. It is also possible that the conjugated or modified fumagillin, fumagillol, or an analog, derivative, salt or ester thereof compounds of the present invention form a covalent bond with MetAP2, thereby irreversibly inhibiting and silencing existing enzyme until a newly produced pool of MetAP2 is generated in target tissues (e.g., liver and adipose tissue.

In certain embodiments, the conjugated or modified fumagillin, fumagillol, or an analog, derivative, salt or ester thereof compounds of the present invention, for example have the following formula as shown in Table 1:

TABLE 1

| Compound No. | Chemical Structure |
|---|---|
| 1 | 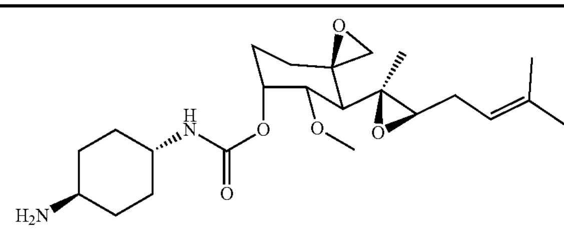 |
| 2 | 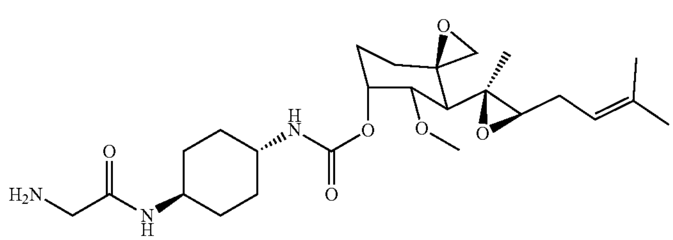 |
| 3 | 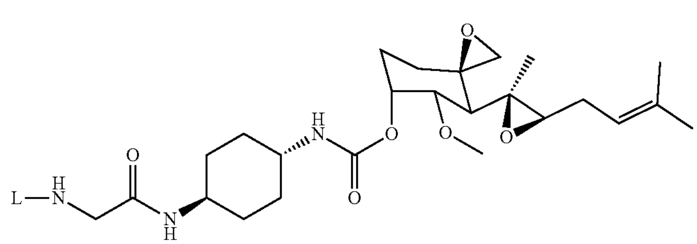 |

TABLE 1-continued

| Compound No. | Chemical Structure |
|---|---|
| 4 | V-NH-CH2-C(O)-NH-[cyclohexyl]-NH-C(O)-O-[fumagillol core] |
| 5 | F-NH-CH2-C(O)-NH-[cyclohexyl]-NH-C(O)-O-[fumagillol core] |
| 6 | G-NH-CH2-C(O)-NH-[cyclohexyl]-NH-C(O)-O-[fumagillol core] |
| 7 | GGL-NH-CH2-C(O)-NH-[cyclohexyl]-NH-C(O)-O-[fumagillol core] |
| 8 | GGV-NH-CH2-C(O)-NH-[cyclohexyl]-NH-C(O)-O-[fumagillol core] |
| 9 | GGF-NH-CH2-C(O)-NH-[cyclohexyl]-NH-C(O)-O-[fumagillol core] |

TABLE 1-continued

| Compound No. | Chemical Structure |
|---|---|
| 10 | GGG—NH—...—NH—(cyclohexyl)—NH—C(=O)—O—[fumagillol core] |
| 11 | GFL—NH—...—NH—(cyclohexyl)—NH—C(=O)—O—[fumagillol core] |
| 12 | Polymer—GGL—NH—...—NH—(cyclohexyl)—NH—C(=O)—O—[fumagillol core] |
| 13 | Polymer—GGV—NH—...—NH—(cyclohexyl)—NH—C(=O)—O—[fumagillol core] |
| 14 | Polymer—GGF—NH—...—NH—(cyclohexyl)—NH—C(=O)—O—[fumagillol core] |
| 15 | Polymer—GGG—NH—...—NH—(cyclohexyl)—NH—C(=O)—O—[fumagillol core] |

TABLE 1-continued

| Compound No. | Chemical Structure |
|---|---|
| 16 | Polymer—GFL—NH—C(O)—CH₂—NH—[cyclohexyl]—NH—C(O)—O—[epoxide-containing terpenoid moiety] |
| 17 | H₂N—(CH₂)₅—NH—C(O)—O—[epoxide-containing terpenoid moiety] |
| 18 | H₂N—CH₂—C(O)—NH—(CH₂)₅—NH—C(O)—O—[epoxide-containing terpenoid moiety] |
| 19 | L—NH—CH₂—C(O)—NH—(CH₂)₅—NH—C(O)—O—[epoxide-containing terpenoid moiety] |
| 20 | V—NH—CH₂—C(O)—NH—(CH₂)₅—NH—C(O)—O—[epoxide-containing terpenoid moiety] |
| 21 | F—NH—CH₂—C(O)—NH—(CH₂)₅—NH—C(O)—O—[epoxide-containing terpenoid moiety] |
| 22 | G—NH—CH₂—C(O)—NH—(CH₂)₅—NH—C(O)—O—[epoxide-containing terpenoid moiety] |

TABLE 1-continued

| Compound No. | Chemical Structure |
|---|---|
| 23 | 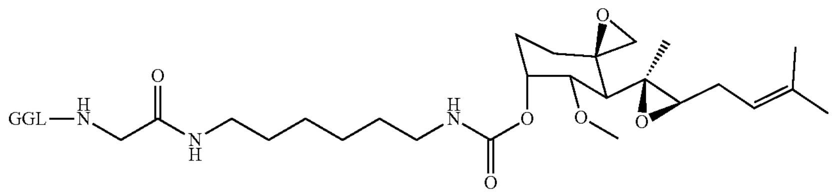 |
| 24 | 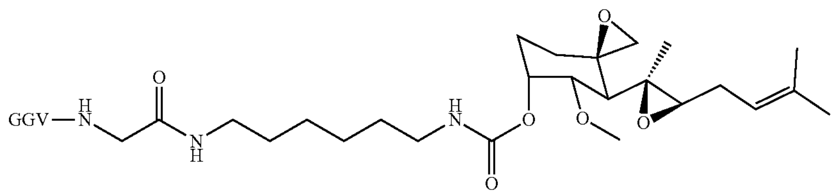 |
| 25 | 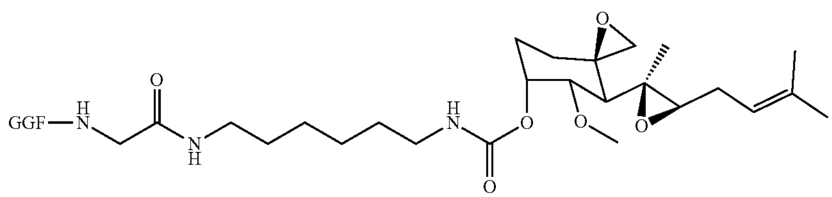 |
| 26 | 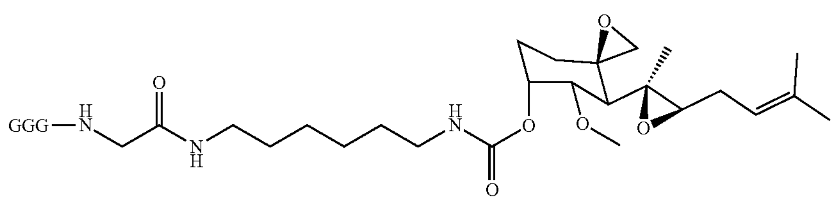 |
| 27 | 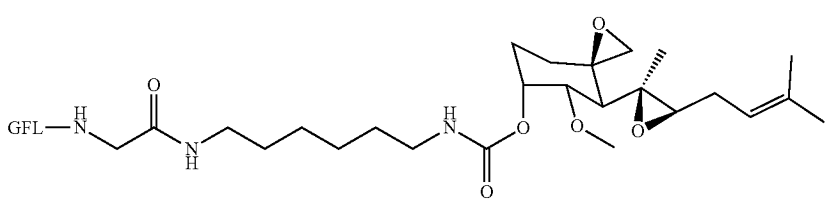 |
| 28 | 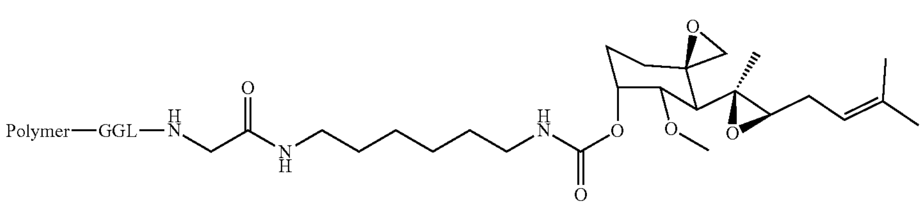 |
| 29 | 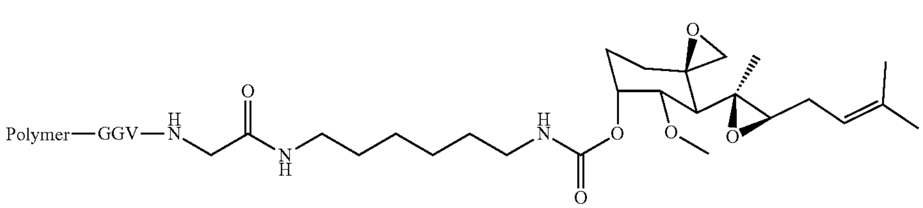 |

TABLE 1-continued
| Compound No. | Chemical Structure |
| --- | --- |
| 30 | 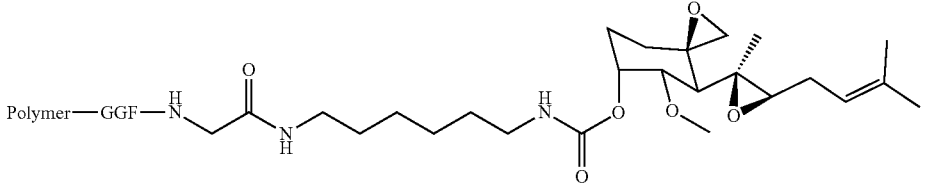 |
| 31 | 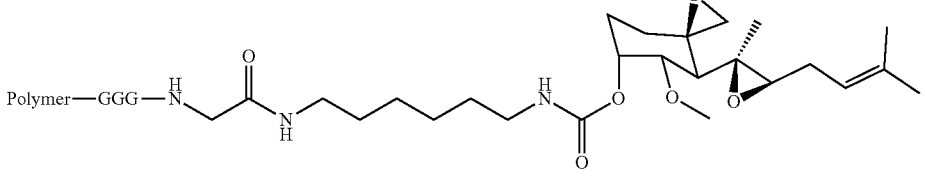 |
| 32 | 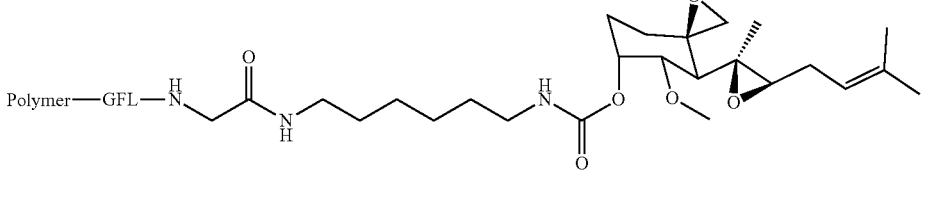 |
| 33 | 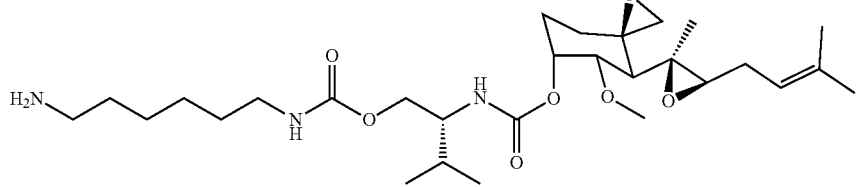 |
| 34 | 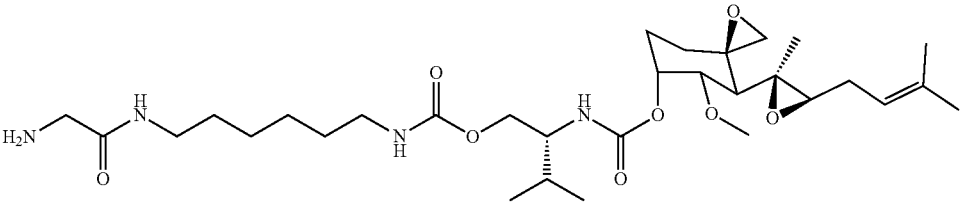 |
| 35 | 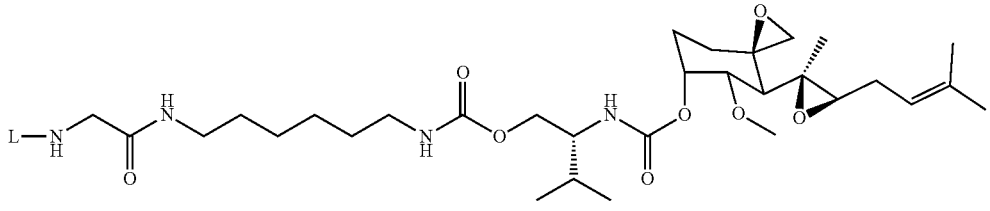 |
| 36 | 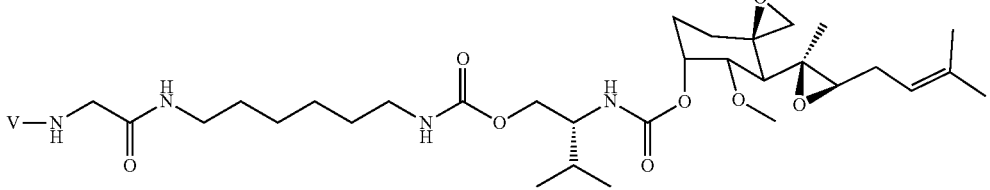 |

TABLE 1-continued

| Compound No. | Chemical Structure |
|---|---|
| 37 | F-NH-Gly-NH-(CH2)6-NH-C(O)-O-CH2-CH(iPr)-NH-C(O)-O-[fumagillol core] |
| 38 | G-NH-Gly-NH-(CH2)6-NH-C(O)-O-CH2-CH(iPr)-NH-C(O)-O-[fumagillol core] |
| 39 | GGL-NH-Gly-NH-(CH2)6-NH-C(O)-O-CH2-CH(iPr)-NH-C(O)-O-[fumagillol core] |
| 40 | GGV-NH-Gly-NH-(CH2)6-NH-C(O)-O-CH2-CH(iPr)-NH-C(O)-O-[fumagillol core] |
| 41 | GGF-NH-Gly-NH-(CH2)6-NH-C(O)-O-CH2-CH(iPr)-NH-C(O)-O-[fumagillol core] |
| 42 | GGG-NH-Gly-NH-(CH2)6-NH-C(O)-O-CH2-CH(iPr)-NH-C(O)-O-[fumagillol core] |
| 43 | GFL-NH-Gly-NH-(CH2)6-NH-C(O)-O-CH2-CH(iPr)-NH-C(O)-O-[fumagillol core] |

TABLE 1-continued
| Compound No. | Chemical Structure |
|---|---|
| 44 | 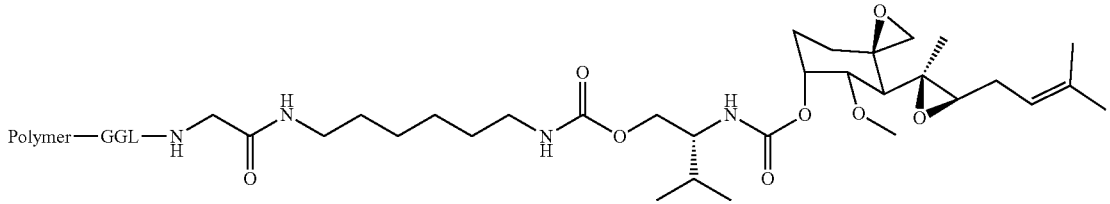 |
| 45 | 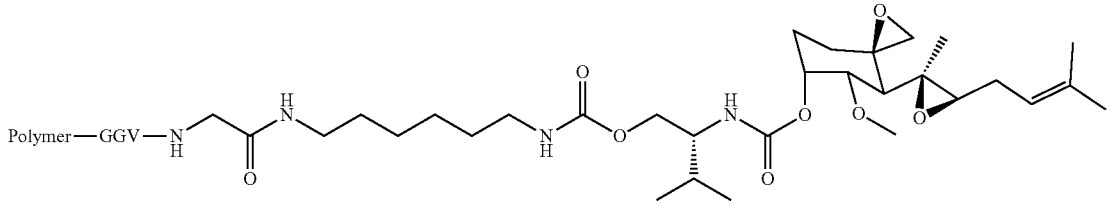 |
| 46 | 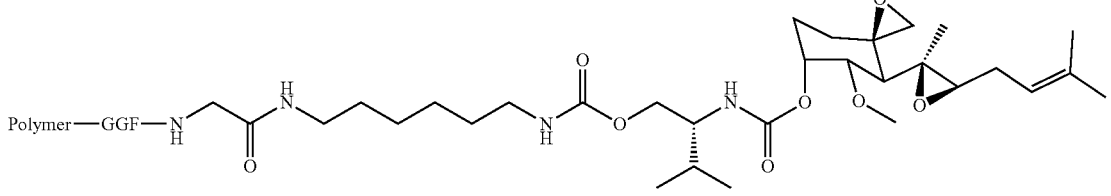 |
| 47 | 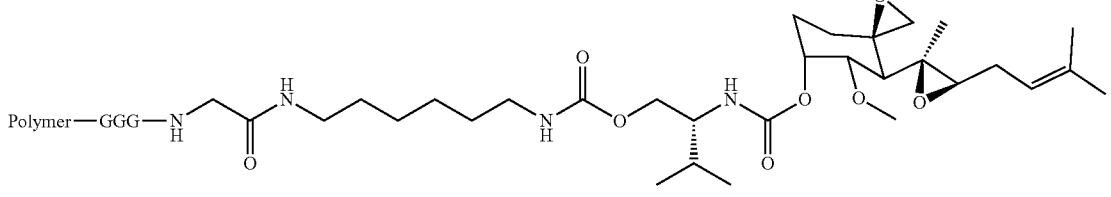 |
| 48 | 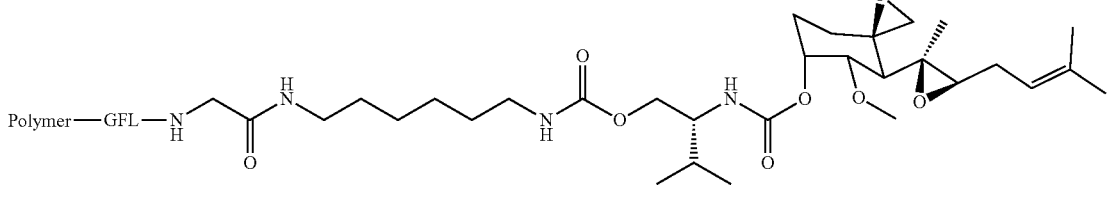 |
| 49 | 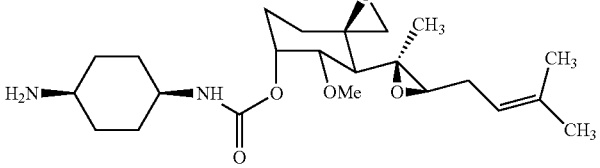 |
*wherein Polymer has the structure of:
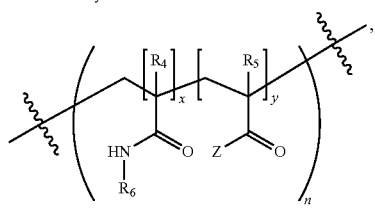

and preferably the structure of:

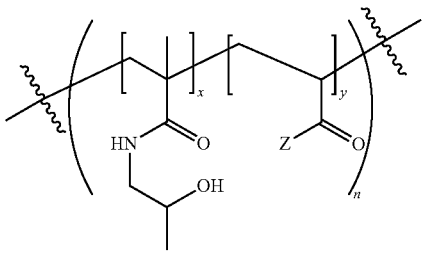

For purposes of this invention, the chemical elements are identified in accordance with the Periodic Table of the Elements, CAS version, Handbook of Chemistry and Physics, 67th Ed., 1986-87, inside cover.

The term "alkyl" refers to a fully saturated branched or unbranched carbon chain radical having the number of carbon atoms specified, or up to 30 carbon atoms if no specification is made. For example, a "lower alkyl" refers to an alkyl having from 1 to 10 carbon atoms, such as methyl, ethyl, propyl, butyl, pentyl, hexyl, heptyl, and octyl, and those which are positional isomers of these alkyls. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, certain cycloalkyls have from 3-10 carbon atoms in their ring structure, and may have 5, 6, or 7 carbons in the ring structure.

Unless the number of carbons is otherwise specified, "lower alkyl", as used herein, means an alkyl group, as defined above, but having from one to ten carbons, or from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, certain alkyl groups are lower alkyls. In certain embodiments, a substituent designated herein as alkyl is a lower alkyl.

The term "carbocycle", as used herein, refers to an aromatic or non-aromatic ring in which each atom of the ring is carbon.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

"Alkenyl" refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

The term "alkynyl" refers to hydrocarbyl radicals of the scope of alkenyl, but having one or more triple bonds in the radical.

The terms "alkoxyl" or "alkoxy" as used herein refers to an alkyl group, as defined below, having an oxygen radical attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, or the like.

The term "alkylthio" refers to an alkyl group, as defined above, having a sulfur radical attached thereto. In certain embodiments, the "alkylthio" moiety is represented by one of —(S)-alkyl, —(S)-alkenyl, —(S)-alkynyl, and —(S)—$(CH_2)_m$—$R_1$, wherein m and $R_1$ are defined below. Representative alkylthio groups include methylthio, ethylthio, and the like.

As used herein, the term "nitro" means —$NO_2$; the term "halogen" designates F, Cl, Br or I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formulae:

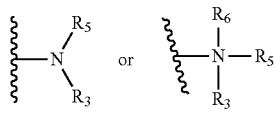

wherein $R_3$, $R_5$ and $R_6$ each independently represent a hydrogen, an alkyl, an alkenyl, —$(CH_2)_m$—$R_1$, or $R_3$ and $R_5$ taken together with the N atom to which they are attached complete a heterocycle having from 4 to 8 atoms in the ring structure; $R_1$ represents an alkenyl, aryl, cycloalkyl, a cycloalkenyl, a heterocyclyl or a polycyclyl; and m is zero or an integer in the range of 1 to 8. In certain embodiments, only one of $R_3$ or $R_5$ can be a carbonyl, e.g., $R_3$, $R_5$ and the nitrogen together do not form an imide. In certain embodiments, $R_3$ and $R_5$ (and optionally $R_6$) each independently represent a hydrogen, an alkyl, an alkenyl, or —$(CH_2)_m$—$R_1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a $pK_a \geq 7.00$. The protonated forms of these functional groups have $pK_a$s relative to water above 7.00.

The term "carbonyl" (C(O)) is art-recognized and includes such moieties as can be represented by the general formula:

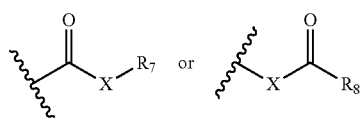

wherein X is a bond or represents an oxygen or a sulfur, and $R_7$ represents a hydrogen, an alkyl, an alkenyl, —$(CH_2)_m$—$R_1$ or a pharmaceutically acceptable salt, $R_8$ represents a hydrogen, an alkyl, an alkenyl or —$(CH_2)_m$—$R_1$, where m and $R_1$ are as defined above. Where X is an oxygen and $R_7$ or $R_8$ is not hydrogen, the formula represents an "ester". Where X is an oxygen, and $R_7$ is as defined above, the moiety is referred to herein as a carboxyl group, and particularly when $R_7$ is a hydrogen, the formula represents a "carboxylic acid". Where X is an oxygen, and $R_8$ is hydrogen, the formula represents a "formate". In general, where the oxygen atom of the above formula is replaced by sulfur, the formula represents a "thiocarbonyl" group. Where X is a sulfur and $R_7$ or $R_8$ is not hydrogen, the formula represents a "thioester" group. Where X is a sulfur and $R_7$ is hydrogen, the formula represents a "thiocarboxylic acid" group. Where X is a sulfur and $R_8$ is hydrogen, the formula represents a "thioformate" group. On the other hand, where X is a bond, and $R_7$ is not hydrogen, the above formula represents a "ketone" group. Where X is a bond, and $R_7$ is hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

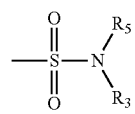

in which $R_3$ and $R_5$ are as defined above.

The term "sulfate" is art recognized and includes a moiety that can be represented by the general formula:

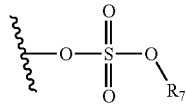

in which $R_7$ is as defined above.

The term "sulfamido" is art recognized and includes a moiety that can be represented by the general formula:

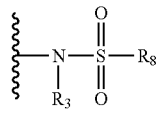

in which $R_2$ and $R_4$ are as defined above.

The term "sulfonate" is art-recognized and includes a moiety that can be represented by the general formula:

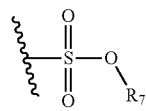

in which $R_7$ is an electron pair, hydrogen, alkyl, cycloalkyl, or aryl.

The terms "sulfoxido" or "sulfinyl", as used herein, refers to a moiety that can be represented by the general formula:

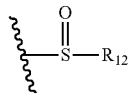

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The term "amino acid" is intended to embrace all compounds, whether natural or synthetic, which include both an amino functionality and an acid functionality, including amino acid analogs and derivatives. In certain embodiments, the amino acids contemplated in the present invention are those naturally occurring amino acids found in proteins, or the naturally occurring anabolic or catabolic products of such amino acids, which contain amino and carboxyl groups. Naturally occurring amino acids are identified throughout by the conventional three-letter and/or one-letter abbreviations, corresponding to the trivial name of the amino acid, in accordance with the following list. The abbreviations are accepted in the peptide art and are recommended by the IUPAC-IUB commission in biochemical nomenclature.

By the term "amino acid residue" is meant an amino acid. In general the abbreviations used herein for designating the naturally occurring amino acids are based on recommendations of the IUPAC-IUB Commission on Biochemical Nomenclature (see Biochemistry (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are —$CH_2CH_2SCH_3$ (the side chain of methionine), —$CH_2$($CH_3$)—$CH_2CH_3$ (the side chain of isoleucine), —$CH_2CH$($CH_3$)$_2$ (the side chain of leucine) or H-(the side chain of glycine). These side chains are pendant from the backbone Cα carbon.

The term "peptide," as used herein, refers to a sequence of amino acid residues linked together by peptide bonds or by modified peptide bonds. The term "peptide" is intended to encompass peptide analogs, peptide derivatives, peptidomimetics and peptide variants. The term "peptide" is understood to include peptides of any length. Peptide sequences set out herein are written according to the generally accepted convention whereby the N-terminal amino acid is on the left, and the C-terminal amino acid is on the right (e.g., $H_2N$-$AA_1$-$AA_2$-$AA_3$-$AA_4$-$AA_5$-$AA_6$-$CO_2H$).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. Any representation of a particular isomer is merely exemplary (e.g., the exemplification of a trans-isomer, also encompasses a cis-isomer).

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

Synthesis of the Compounds of the Invention

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of the present invention may be prepared according to the schemes and examples provided herein from commercially available starting materials or starting materials which can be prepared using literature procedures. The compounds of the present invention, and their synthesis, are further described in PCT Publication Nos. WO 2011/150088 and WO 2011/150022. Each of these publications is incorporated by reference in their entireties for all purposes.

Pharmaceutical Compositions

The present invention also provides pharmaceutical compositions comprising a compound of the present invention, or pharmaceutically acceptable salts, solvates, diastereomers, and polymorphs thereof, and a pharmaceutically acceptable carrier or excipient.

As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions. In certain embodiments, the pharmaceutical composition comprises DMSO.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (See, for example, Berge et al. (1977) "Pharmaceutical Salts", *J. Pharm. Sci.* 66:1-19)

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

As used herein, the term "metabolite" means a product of metabolism of the compound of present invention, or pharmaceutically acceptable salts, solvates, diastereomers, and polymorphs thereof, that exhibits a similar activity in vivo to the compound of present invention, or pharmaceutically acceptable salts, solvates, diastereomers, and polymorphs thereof.

As used herein, the term "prodrug" means the compound of present invention, or pharmaceutically acceptable salts, solvates, diastereomers, and polymorphs thereof covalently linked to one or more pro-moieties, such as an amino acid moiety or other water solubilizing moiety. The compound of present invention, or pharmaceutically acceptable salts, solvates, diastereomers, and polymorphs thereof may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate within R4, may be selected based on solubility, stability, bioavailability, and/or in vivo delivery or uptake. Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

Methods of Treatment

The present invention provides methods of inducing or causing weight loss in a subject in need thereof comprising administering at least one compound of the present invention in a therapeutically effective amount to the subject to induce or cause weight loss. In certain embodiments, the subject is overweight or obese. In certain embodiments, inducing or causing weight loss is increasing weight loss.

The present invention also provides methods for preventing or delaying weight increase in a subject at risk thereof comprising administering at least one compound of the present invention in a therapeutically effective amount to the subject to prevent or delay the increase in weight. In certain embodiments, the subject is at risk of becoming overweight or becoming obese.

The present invention provides methods of treating obesity in a subject in need thereof comprising administering at least one compound of the present invention in a therapeutically effective amount to the subject to treat or ameliorate obesity.

The present invention also provides methods for preventing or delaying the development of obesity in a subject at risk thereof comprising administering at least one compound of the present invention in a therapeutically effective amount to the subject to prevent or delay the development of obesity.

The present invention provides methods of treating metabolic syndrome or one or more of the components thereof in a subject in need thereof comprising administering at least one compound of the present invention in a therapeutically effective amount to the subject to treat or ameliorate metabolic syndrome or one or more of the components thereof.

The present invention also provides methods for preventing or delaying the development of metabolic syndrome or one or more of the components thereof in a subject at risk thereof comprising administering at least one compound of the present invention in a therapeutically effective amount to the subject to prevent or delay the development of metabolic syndrome or one or more of the components thereof.

The present invention also provides methods of decreasing body weight in a subject in need thereof comprising administering at least one compound of the present invention in a therapeutically effective amount to the subject to decrease body weight. In certain embodiments, the subject is overweight or obese. In certain embodiments the subject is in need of reducing excess adipose tissue.

Obesity and being overweight refer to an excess of fat in a subject in proportion to lean body mass. Excess fat accumulation is associated with an increase in size (hypertrophy or steatosis) as well as number (hyperplasia) of adipose tissue cells. Obesity may be due to any cause, whether genetic (e.g. Prader-Willi Syndrome) or environmental. Obesity is variously measured in terms of absolute weight, weight:height ratio, degree of excess body fat, distribution of visceral or subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using the formulas: SI units: BMI=weight(kg)/(height$^2$(m$^2$), or US units: BMI=(weight(lb)*703)/(height$^2$ (in$^2$).

As described herein, "overweight" refers to a condition whereby an otherwise healthy adult that has a BMI of 25 kg/m$^2$ to 29.9 kg/m$^2$. As described herein, "obese" or "obesity" refers to a condition whereby an otherwise healthy adult that has a BMI of 30 kg/m$^2$ or greater. Obesity has several subcategories. An adult that has a BMI of 35 kg/m$^2$ or greater is referred to as "severely obese" or "severe obesity". An adult that has a BMI of ≥40-44.9 kg/m$^2$ or and adult that has a BMI of 35 kg/m$^2$ or greater and at least one obesity-related health condition is referred to as "morbidly obese" or "morbid obesity". An adult that has a BMI of 45 kg/m$^2$ or greater is referred to as "super obese" or "super obesity". For children, the definitions of overweight and obese take into account age and gender effects on body fat.

Different countries may define obesity and overweight with different BMI. The term "obesity" is meant to encompass definitions in all countries. For example, the increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25.0 kg/m$^2$. Ethnic South and Central Americans tend to be categorized more closely to Asians than Europeans or North Americans.

BMI does not account for the fact that excess adipose tissue can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Assessment of disease is performed using standard methods known in the arts, for example, by monitoring appropriate marker(s). For example, the following markers may be monitored for obesity: body weight, BMI, body composition study, body fat distribution, central fat distribution, food or calorie intake, behavioral measurement of hunger and satiety, metabolic rate, and obesity-related co-morbidities.

Methods of determining whether a subject is overweight or obese that account for the ratio of excess adipose tissue to lean body mass may involve obtaining a body composition of the subject. Body composition can be obtained by measuring the thickness of subcutaneous fat in multiple places on the body, such as the abdominal area, the sub-scapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink. Another method is fan-beam dual energy X-ray absorptiometry (DEXA). DEXA allows body composition, particularly total body fat and/or regional fat mass, to be determined non-invasively. MRI may also be used to determine composition non-invasively.

With respect to all methods described herein, reference to the compounds of the instant invention also include compositions, such as pharmaceutical compositions as described herein, comprising one or more of these compounds. These compositions may further comprise suitable excipients, such as pharmaceutically acceptable excipients including buffers, which are well known in the art. The present invention can be used alone or in combination with other conventional methods of treatment.

A subject in need of treatment as provided by the present invention may also have (i.e., be diagnosed with or suffering from) at least one obesity-induced or obesity-related co-morbidity, i.e., diseases and other adverse health conditions associated with, exacerbated by, or precipitated by being overweight or obese. In other embodiments, the subject may have at least two obesity-induced or obesity-related co-morbidities.

Obesity-induced or obesity-related co-morbidities include, but are not limited to, diabetes, non-insulin dependent diabetes mellitus-type II, impaired glucose tolerance, impaired fasting glucose, dysglycaemia, elevated plasma insulin concentrations, insulin resistance syndrome, hyperlipidemia, dyslipidemia, elevated free fatty acids, hypertension, hyperuricacidemia, gout, coronary artery disease, cardiac disease, myocardial infarction, angina pectoris, microvascular disease, sleep apnea, obstructive sleep apnea, Pickwickian syndrome, fatty liver; cerebral infarction, stroke, cerebral thrombosis, respiratory complications, cholelithiasis, gallbladder disease, kidney disease, gastroesophageal reflux, stress urinary incontinence, arteriosclerosis, heart disease, abnormal heart rhythms, heart arrhythmias, transient ischemic attack, orthopedic disorders, osteoarthritis, arthritis deformans, lumbodynia, emmeniopathy, hormonal imbalances, endocrinopathies and infertility. In particular, co-morbidities include: hypertension, hyperlipidemia, dyslipidemia, glucose intolerance, cardiovascular disease, sleep apnea, diabetes mellitus, and other obesity-related conditions.

The present invention provides, in addition to treating obesity or inducing, causing or increasing weight loss (decreasing weight) in a subject in need thereof, methods of treating one or more of these obesity-induced or obesity-related co-morbidities in a subject suffering from said co-morbidities comprising administering at least one compound of the present invention in a therapeutically effective amount to the subject to treat or ameliorate obesity or decrease body weight, and treat or ameliorate one or more of obesity-induced or obesity-related co-morbidities.

The present invention provides methods for treating metabolic disorders or metabolic syndrome in a subject in need thereof wherein said syndrome is characterized by a group of metabolic risk factors including: 1) abdominal obesity (excessive fat tissue in and around the abdomen); 2) atherogenic dyslipidemia (high triglycerides; low HDL cholesterol and high LDL cholesterol or a low HDL:LDL ratio); 3) elevated blood pressure; 4) insulin resistance or glucose intolerance; 5) a prothrombotic state (e.g., high fibrinogen or plasminogen activator inhibitor-1 in the blood); 6) a proinflammatory state (e.g., elevated CRP in the blood); and 7) pre-diabetes or type 2 diabetes. The present invention can treat metabolic disease(s) alone or in combination with treating obesity or inducing, causing or increasing weight loss.

The present invention also provides, in addition to treating obesity or inducing, causing or increasing weight loss in a subject in need thereof, methods of treating, decreasing or improving one or more cardiometabolic risk factors selected from but not limited to the group consisting of plasma triglyceride levels, LDL-cholesterol levels, C-reactive protein (CRP) levels, and blood pressure (systolic and/or diastolic) in a subject suffering from said risk factors comprising administering at least one compound of the present invention in a therapeutically effective amount to the subject to treat or ameliorate obesity or decrease body weight, and treat or ameliorate one or more of risk factors.

A compound of the present invention, or a pharmaceutically acceptable salt, prodrug, metabolite, analog or derivative thereof, may be administered in combination with a second active agent. The second active agent may also be conjugated to a polymer.

Contemplated second active agents include those administered to treat type 2 diabetes such as sulfonylureas (e.g., chlorpropamide, glipizide, glyburide, glimepiride); meglitinides (e.g., repaglinide and nateglinide); biguanides (e.g., metformin); thiazolidinediones (rosiglitazone, troglitazone, and pioglitazone); glucagon-like 1 peptide mimetics (e.g. exenatide and liraglutide); sodium-glucose cotransporter inhibitors (e.g., dapagliflozin), dipeptidyl peptidase 4 inhibitors (e.g. gliptins), sodium-glucose linked transporter inhibitors, renin inhibitors, and alpha-glucosidase inhibitors (e.g., acarbose and meglitol), and/or those administered to treat cardiac disorders and conditions, such as hypertension, dyslipidemia, ischemic heart disease, cardiomyopathy, cardiac infarction, stroke, venous thromboembolic disease and pulmonary hypertension, which have been linked to overweight or obesity, for example, chlorthalidone; hydrochlorothiazide; indapamide, metolazone; loop diuretics (e.g., bumetanide, ethacrynic acid, furosemide, lasix, torsemide); potassium-sparing agents (e.g., amiloride hydrochloride, spironolactone, and triamterene); peripheral agents (e.g., reserpine); central alpha-agonists (e.g., clonidine hydrochloride, guanabenz acetate, guanfacine hydrochloride, and methyldopa); alpha-blockers (e.g., doxazosin mesylate, prazosin hydrochloride, and terazosin hydrochloride); beta-blockers (e.g., acebutolol, atenolol, betaxolol, nisoprolol fumarate, carteolol hydrochloride, metoprolol tartrate, metoprolol succinate, Nadolol, penbutolol sulfate, pindolol, propranolol hydrochloride, and timolol maleate); combined alpha- and beta-blockers (e.g., carvedilol and labetalol hydrochloride); direct vasodilators (e.g., hydralazine hydrochloride and minoxidil); calcium antagonists (e.g., diltiazem hydrochloride and verapamil hydrochloride); dihydropyridines (e.g., amlodipine besylate, felodipine, isradipine, nicardipine, nifedipine, and nisoldipine); ACE inhibitors (benazepril hydrochloride, captopril, enalapril maleate, fosinopril sodium, lisinopril, moexipril, quinapril hydrochloride, ramipril, trandolapril); angiotensin II receptor blockers (e.g., losartan potassium, valsartan, and Irbesartan); and combinations thereof, as well as statins such as mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin, typically for treatment of dyslipidemia.

Other second active agents that may be co-administered (e.g. sequentially or simultaneously) include agents administered to treat ischemic heart disease including statins, nitrates (e.g., Isosorbide Dinitrate and Isosorbide Mononitrate), beta-blockers, and calcium channel antagonists, agents administered to treat cardiomyopathy including inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers, agents administered to treat cardiac infarction including ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase), agents administered to treat strokes including anti-platelet agents (e.g., Aspirin, Clopidogrel, Dipyridamole, and Ticlopidine), anticoagulant agents (e.g., Heparin), and thrombolytic agents, agents administered to treat venous thromboembolic disease including anti-platelet agents, anticoagulant agents, and thrombolytic agents, agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil, agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex, agents administered to treat sleep apnea include Modafinil and amphetamines, agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents, agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid, agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax), agents administered to treat polycystic ovary syndrome include insulin-sensitizers, combinations of synthetic estrogen and progesterone, Spironolactone, Eflornithine, and Clomiphene, agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone, agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta, agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic, agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate), agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers, and other weight loss agents, including serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, and topamax.

The present invention also provides methods of decreasing adipocytes in a subject in need thereof comprising administering at least one compound of the present invention in a therapeutically effective amount to the subject to decrease adipocytes or adipose tissue. The present invention also provides methods of preventing an increase in adipocytes in a subject at risk thereof comprising administering at least one compound of the present invention in a therapeutically effective amount to the subject to prevent an increase in adipocytes. Decreasing adipocytes means decreasing the number or decreasing the size (fat content) of the adipocytes. Preventing an increase in adipocytes means decreasing or maintaining the number or decreasing or maintaining the size of the adipocytes. In certain embodiments, administration of the compounds of the present invention shrink the adipocytes in the subject in need thereof. The adipose tissue can be white adipose tissue or brown adipose tissue.

The present invention also provides methods of decreasing food intake in a subject in need thereof comprising administering at least one compound of the present invention in a therapeutically effective amount to the subject to decrease food intake.

A reduction in food intake means a decrease in daily food intake. A decrease in daily food intake can be about a 5% decrease to about a 50% decrease (e.g., about 5%, about 10%, about 20%, about 30%, about 40% or about 50%). Based on a 2000 kcal daily diet, the decrease is about 100 kcal to about 1000 kcal decrease per day (e.g., about 100 kcal, about 200 kcal, about 400 kcal, about 600 kcal, about 800 kcal or about 1000 kcal).

The present invention also provides methods for reducing a sense of hunger in a subject in need thereof comprising administering at least one compound of the present invention in a therapeutically effective amount to the subject to reduce a sense of hunger. The subject may also have a decrease in food intake.

Sense of hunger can be assessed in a fasted state using a 10-point visual analog scale (VAS), which is well utilized in appetite research. See, Flint et al. *Int. J. Obes. Relat. Metab. Disord.* 24(1): 38-48, 2000. Specifically, subjects are asked to rate their overall sense of hunger for the previous 2 days on a scale of 1-10, where 10 was extremely hungry and 1 was not hungry at all.

The methods of present invention can also decrease waist circumference in a subject in need thereof. Waist circumference is assessed by using a tape measure placed around the abdomen 1 cm above the iliac crest. The subjects of the present invention may have a decrease in waist circumference from about 1 inch to about 20 inches (e.g., 1, 2, 3, 4, 5, 6, 7, 8, 9, 10, 11, 12, 13, 14, 15, 16, 17, 18, 19 or 20 inches).

In the methods of the present invention, administration of the compounds results in decreased body fat and a substantial maintenance of muscle mass in said patient. In certain embodiments, upon administration, fat oxidation is enhanced in a patient as compared to a patient on a restricted food intake diet alone. For example, provided herein is a method of decreasing body fat in a patient in need thereof. Such a patient may retain substantially more muscle mass as compared to body fat reduction in a patient using an energy restricted diet alone.

The present invention also provides methods for improving surgical outcome in a subject in need thereof comprising administering, prior to surgery, at least one compound of the present invention in a therapeutically effective amount to the subject to improve surgical outcome. In certain embodiments, administration reduces liver and/or abdominal fat in said patient and improves surgical outcome. In certain embodiments, the surgery is non-acute surgery. Such surgeries may include bariatric surgery, cardiovascular surgery, abdominal surgery, or orthopedic surgery.

A "patient" or "subject" as recited herein can mean either a human or non-human subject. In certain embodiments, the subject is a vertebrate. In certain embodiments, the vertebrate is a mammal. Mammals also include, but are not limited to, farm animals, sport animals, pets, primates (including humans), horses, dogs, cats, mice and rats. In certain embodiments, the mammal is a human.

As used herein, a "subject in need thereof" is a subject that is overweight or obese (who may or may not have one or more co-morbidities), or a subject having an increased risk of becoming overweight or developing obesity relative to the population at large. In certain aspects, a subject in need thereof is obese having a BMI of 30 kg/m$^2$ or greater. In certain aspects, the subject in need thereof is a subject that is overweight or obese or having an increased risk of becoming overweight or developing obesity relative to the population at large who is not suffering from, or is not diagnosed with, a disorder selected from the group consisting of cancer, hyper-proliferative disorder, retinal neovascularization due to macular degeneration, psoriasis and pyogenic granuloma, rheumatoid, immune and degenerative arthritis.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

As used herein, "treatment" is an approach for obtaining beneficial or desired clinical results. For purposes of this invention, beneficial or desired clinical results include, but are not limited to, one or more of the following: improving, lessening severity, alleviation of one or more symptoms associated with a disease. For obesity, beneficial or desired clinical results include any one or more of the following: reducing or maintaining body weight; controlling (including reducing) food intake or calorie intake; increasing metabolic rate or inhibiting reduction of metabolic rate; and improving, lessening severity, and/or alleviating any of the disorders associated with obesity, such as diabetes, non-insulin dependent diabetes mellitus, hyperglycemia, low glucose tolerance, insulin resistance, lipid disorder, dyslipidemia, hyperlipidemia, hypertriglyceridemia, hypercholesterolemia, abdominal obesity, eating disorder, metabolic syndrome, hypertension, osteoarthritis, myocardial infarction, fatty liver disease, steatohepatitis, non-alcoholic steatohepatitis (NASH), non-alcoholic fatty liver disease (NAFLD), stroke and other associated diseases; increasing the quality of life of those suffering from the obesity, and/or prolonging lifespan.

As used herein, "delaying" development of obesity means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. For example, one outcome of delaying development may be reducing the body weight of a subject at risk of obesity relative to that subject's body weight immediately before the administration of the compositions described herein. Another outcome of delaying development may be preventing regain of body weight previously lost as a result of diet, exercise, or pharmacotherapy. Another outcome of delaying development may be preventing obesity from occurring if the treatment is administered prior to the onset of obesity in a subject at risk of obesity. Another outcome of delaying development may be decreasing the occurrence and/or severity of obesity-related disorders if the treatment is administered prior to the onset of obesity in a subject at risk of obesity.

An individual "at risk" of obesity may or may not have detectable disease, and may or may not have displayed detectable disease prior to the treatment methods described herein. "At risk" denotes that an individual has one or more so-called risk factors, which are measurable parameters that correlate with development of obesity. An individual having one or more of these risk factors has a higher probability of being obese than an individual without these risk factor(s). These risk factors include, but are not limited to, age, diet, physical inactivity, metabolic syndrome, family history of obesity, ethnicity, hereditary syndromes, history of previous disease (e.g. eating disorder, metabolic syndrome, and obesity), presence of precursor disease (e.g., overweight). For example, an otherwise healthy individual with a BMI of 25.0 to less than 30.0 kg/m$^2$ or an individual with at least one co-morbidity with a BMI of 25.0 kg/m$^2$ to less than 27.0 kg/m$^2$ is at risk of obesity.

"Development" of obesity means the onset and/or progression of the disease within an individual (which can be different embodiments of the invention). Obesity development can be detectable using standard clinical techniques as described herein. However, development also refers to disease progression that may be initially undetectable. For purposes of this invention, progression refers to the biological course of the disease state, in this case, as determined by assessing height and weight for estimating BMI, measuring waist circumference, assessing co-morbidities, as well as the onset and/or worsening of obesity complications such as arteriosclerosis, Type II diabetes, polycystic ovary disease, cardiovascular diseases, osteoarthritis, dermatological disorders, hypertension, insulin resistance, hypercholesterolemia, hypertriglyceridemia, and cholelithiasis. A variety of these diagnostic tests are known in the art. "Development" includes occurrence, recurrence, and onset. As used herein "onset" or "occurrence" of obesity includes initial onset and and/or recurrence.

As used herein, "controlling body weight" or "improvement in body weight" refers to reducing or maintaining the body weight in an individual (as compared to the level before treatment). In some embodiments, the body weight is generally maintained within the normal range. The body weight may be reduced by reducing the calorie intake and/or reducing the body fat accumulation. In some embodiments, the body weight is reduced at least about any of 3%, 4%, 5%, 10%, 20%, 30%, 40%, or 50% in the individual as compared to the level before treatment.

As used herein, "controlling food intake" refers to reducing or maintaining the food intake in an individual (as compared to the level before treatment). In some embodiments, the food intake is generally maintained in the normal range. In some embodiments, the food intake is reduced by about any of 3%, 4%, 5%, 10%, 20%, 30%, 40%, or 50%, in the individual as compared to the level before treatment.

A "therapeutically effective amount" of a compound, with respect to use in treatment, refers to an amount of a compound in a preparation which, when administered as part of a desired dosage regimen (to a mammal, preferably a human) alleviates a symptom, ameliorates a condition, or slows or prevents the onset of disease conditions according to clinically acceptable standards for the disorder or condition to be treated or the cosmetic purpose, e.g., at a reasonable benefit/risk ratio applicable to any medical treatment. A "therapeutically effective amount" is synonymous with "efficacious dose".

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing intensity, duration, or frequency of attack of the disease, and decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved. For example, an effective amount of a compound of the present invention for treating obesity is an amount sufficient to treat or ameliorate one or more symptoms associated with obesity. An "effective amount" is an amount sufficient to result in one or more of the following (which can also correspond to various embodiments of the invention): decreasing, reducing or controlling body weight, decreasing, reducing or controlling food intake, increasing metabolic rate, decreasing one or more symptoms resulting from the diseases associated with obesity, increasing the quality of life of those suffering from the obesity, and/or prolonging lifespan.

In providing a subject with one or more of the compounds described herein, the dosage of administered compound(s) will vary depending upon such factors as the subject's age, weight, height, sex, general medical condition, previous medical history, disease progression, route of administration, formulation and the like.

Dosages for a compound of the present invention may be determined empirically in individuals who have been given one or more administration(s). Individuals are given incremental dosages of a compound of the present invention. To assess efficacy of a compound of the present invention, markers of the disease state can be monitored. It will be apparent to one of skill in the art that the dosage will vary depending on the individual, the stage of the disease (e.g., stage of obesity), and the past and concurrent treatments being used.

Toxicity and therapeutic efficacy of compounds of the present invention can be determined by standard pharmaceutical procedures in experimental animals. Toxic doses may be determined as the maximum tolerated dose (MTD) or alternatively the LD50 (the dose lethal to 50% of the population). Efficacious doses may be determined as the ED50 (the dose therapeutically effective in 50% of the population) or dose required to provide some average amount of change in an animal (e.g. the dose required to provide an average reduction in systolic blood pressure of 10 mm Hg in a group of subjects).

Ideally, the efficacious and toxic doses may be determined in the same species. However if they are determined in different species, allometric scaling may be used to translate the efficacious or toxic dose to another species. The dose ratio between toxic and therapeutic effects is the therapeutic index and it can be expressed as the ratio LD50/ED50. In comparing mice to rats, the commonly accepted scaling factor is 2; the rat dose is estimated to be one-half the dose in mice. Thus if the toxic dose in a rat is 100 mg/kg and the efficacious dose in a mouse is 1 mg/kg, the therapeutic index in the rat may be calculated as efficacious dose in rat equals 1 mg/kg/2 or 0.5 mg/kg and the therapeutic index is 200. FDA defines a drug as having a narrow therapeutic range if: (a) less than 2-fold difference between median lethal and median effective dose, or (b) less than 2-fold difference between minimum toxic and minimum effective concentrations in the blood.

Compounds of the present invention which exhibit large therapeutic indices are preferred. While compounds of the present invention that exhibit toxic side effects may be used, care should be taken to design a delivery system that targets such compounds of the present invention to the site of affected tissue in order to minimize potential damage to uninfected cells and, thereby, reduce side effects.

The data obtained from animal studies can be used in formulating a range of dosage for use in humans. The dosage of such compounds of the present invention lies preferably within a range of circulating concentrations that include the efficacious dose range with little or no toxicity. The dosage may vary within this range depending upon the dosage form employed and the route of administration utilized. For compounds of the present invention with a MW less than 1000, the therapeutically effective dose can be estimated initially from cell culture assays while animal models will provide a better estimation of dose for conjugates where the linker requires cleavage to release an active moiety. Such information can be used to more accurately determine useful doses in humans. It is well known in the art that polymer conjugation dilutes the activity of the active moiety (polymer is a diluent). This is exemplified in the mouse dosing model of the anti-cancer drugs shown in the following Table.

| Parent Drug | Drug Dose (mg/kg) | Conjugate | Conjugate Dose (mg/kg) |
| --- | --- | --- | --- |
| TNP-470 | 30 (qod) | XMT-1107 | 800 |
| Docetaxel | 12 (Q4d) | Opaxio | 480 |
| CPT-11 | 20 (q2d) | EZN-2208 | 145 (q2d) |
| Doxorubicin | 5 (q4d) | PK1 | 62 (q7d) |
| Carboplatin | 60 (Qd) | AP-5356 | 2200 |

Thus, it is well understood that polymer conjugation increases clinical doses, where therapeutic index is not improved. This is exemplified in the human dosing model of the anti-cancer drugs shown in the following Table.

| Parent Drug | Drug Dose (mg/m$^2$) | Conjugate | Conjugate Dose (mg/m$^2$) |
| --- | --- | --- | --- |
| TNP-470 | 180 | XMT-1107 | tbd |
| Paclitaxel | 175 | Opaxio | 473 |
| CPT-11 | 125 | EZN-2208 | 260 |
| Doxorubicin | 75 | PK1 | 280 |
| Oxaliplatin | 85 | AP-5346 | 6400 |

The polymer conjugate and modified compounds of the present invention surprisingly provide superior efficacy and lower toxicity when compared to the unconjugated and or unmodified parent drug/active moiety.

For example, the fumagillol conjugates and modified fumagillol compounds of the present invention are surprisingly superior to fumagillol small molecules as they provide increased weight reduction in DIO mice at equivalent molar doses. The compounds of the present invention may be used at lower molar doses and with less frequent dosing to provide equivalent weight loss. Lower molar doses and reduced dosing frequency reduce systemic drug exposure and systemic drug toxicity. Additionally, the fumagillol conjugates and modified fumagillol compounds of the present invention provide the following action similar to fumagillol small molecules: preferential loss of fat in DIO mice and reduction in food consumption.

Traditional polymer conjugates dilute activity, increase doses by 5-20× and provide little change in therapeutic index (<2×). In contrast, the polymer conjugate compounds of the present invention surprisingly and unexpectedly provide an enhanced therapeutic index (order of magnitude improvement) and demonstrate increased activity at a reduced dose.

In the methods of the present invention, the polymer conjugate compounds of the present invention surprisingly demonstrate less frequent dose administration (e.g., q4d, dosing every fourth day, q7d, dosing every seventh day, q8d, dosing every eighth day), doses which are decreased at least 84 mole % fumagillol equivalent, reduced AUC in non-target compartments while therapeutic index is increased (>10×).

In another embodiment, provided herein are effective dosages, e.g. a daily dosage of a compound of the present invention. For example, provided here are methods that include administering doses of a compound of the present invention that are effective for weight loss. For example, contemplated dosage of a compound of the present invention in the methods described herein may include administering a dose independent of body weight of about 200 mg/day, about 80 mg/day, about 40 mg/day, about 20 mg/day, about 10 mg/day, about 5 mg/day, about 3 mg/day, about 2 mg/day, about 1 mg/day, about 0.5 mg/day, about 0.2 mg/day, about 0.05 mg/day, about 0.01 mg/day, or about 0.001 mg/day.

An effective amount of the drug for weight loss in a patient may also be dosed based on body weight or surface area and be about 0.0001 mg/kg to about 5 mg/kg of body weight per day. For example, a contemplated dosage may be from about 0.001 to 5 mg/kg of body weight per day, about 0.001 mg/kg to 1 mg/kg of body weight per day, about 0.001 mg/kg to 0.1 mg/kg of body weight per day, about 0.001 to about 0.010 mg/kg of body weight a day or about 0.007 mg/kg of body weight a day.

The compounds of the present invention can be administered in an amount sufficient to reduce the body weight of the patient by about 0.5 kg/week to about 1 kg/week (or about 0.5% of body weight per week to about 1% of body weight per week). In certain embodiments, the weekly reduction in body weight occurs for the duration of the treatment.

Administration of a compound of the present invention in accordance with the method in the present invention can be continuous or intermittent, depending, for example, upon the recipient's physiological condition, whether the purpose of the administration is therapeutic or prophylactic, and other factors known to skilled practitioners. The administration of a compound of the present invention may be essentially continuous over a preselected period of time or may be in a series of spaced doses.

For repeated administrations over several days or longer, depending on the condition, the treatment is sustained until a desired suppression of disease symptoms occurs or until sufficient therapeutic levels are achieved. For example, dosing from one to five times a week is contemplated. In certain embodiments, a compound of the present invention is administered about every fourth day. Other dosing regimens include a regimen of, 1 to 5 times per week, every three to four days, or less frequently. In some embodiments, a compound of the present invention is administered about once per week, once every two weeks, or about 1 to 4 times per month depending on the duration of the response to drug administration. Intermittent dosing regimen with staggered dosages spaced by 2 days up to 7 days or even 14 days may be used. In some embodiments, treatment may start with a daily dosing and later change to weekly even monthly dosing. The progress of this therapy is easily monitored by conventional techniques and assays, or by measuring MetAP2 as described in U.S. Pat. No. 6,548,477.

Frequency of administration may be determined and adjusted over the course of therapy. For example, frequency of administration may be determined or adjusted based on the type and severity of the disease to be treated, whether the agent is administered for preventive or therapeutic purposes, previous therapy, the patient's clinical history and response to the agent, and the discretion of the attending physician. Typically the clinician will administer a compound of the present invention until a dosage is reached that achieves the desired result Treatment can be continued for as long or as short a period as desired. A suitable treatment period can be, for example, at least about one week, at least about four weeks, at least about one month, at least about six months, at least about 1 year, at least about 2 years, or indefinitely. A treatment period can terminate when a desired result, for example a weight loss target, is achieved. For example, when loss of about 5% body weight, about 10% body weight, about 20% body weight, about 30% body weight or more has been achieved. A treatment regimen can include a corrective phase, during which a compound of the present invention is administered in dose, or dosing frequency, sufficient to provide reduction of excess adiposity is administered, followed by a maintenance phase, during which a lower compound dose, or decreased dosing frequency, sufficient to prevent re-development of excess adiposity is administered.

The compounds, or pharmaceutically acceptable salts, esters or pro-drugs thereof (or pharmaceutical compositions thereof) can be administered by any means known in the art. For example, the compounds or compositions of the present invention are administered orally, nasally, transdermally, topically, pulmonary, inhalationally, buccally, sublingually, intraperintoneally, subcutaneously, intramuscularly, intravenously, rectally, intrapleurally, intrathecally and parenterally. Administration can be systemic, e.g., intravenous administration, or localized. In certain embodiments, the route of administration may be intravenous, intramuscular, subcutaneous, intradermal, intraperitoneal, intrathecal, intrapleural, intrauterine, rectal, vaginal, topical, and the like. In certain embodiments, the compound is administered subcutaneously.

In one aspect, the compounds of the present invention, or pharmaceutically acceptable salts, solvates, diastereomers, and polymorphs thereof, are administered in a suitable dosage form or formulation prepared by combining a therapeutically effective amount (e.g., an efficacious level sufficient to achieve the desired therapeutic effect) of the compound of the present invention, or pharmaceutically acceptable salts, solvates, diastereomers, and polymorphs thereof (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

Parenteral dosage forms may be prepared by any means known in the art. For example, sterile injectable aqueous or oleaginous suspensions may be formulated according to the known art using suitable dispersing or wetting agents and suspending agents.

Oral dosage forms, such as capsules, tablets, pills, powders, and granules, may be prepared using any suitable process known to the art. For example, the compounds of the present invention may be mixed with enteric materials and compressed into tablets. Alternatively, formulations of the invention are incorporated into chewable tablets, crushable tablets, tablets that dissolve rapidly within the mouth, or mouth wash.

For pulmonary (e.g., intrabronchial) administration, the compounds of the present invention can be formulated with conventional excipients to prepare an inhalable composition in the form of a fine powder or atomizable liquid. For ocular administration, the compounds of the present invention can be formulated with conventional excipients, for example, in the form of eye drops or an ocular implant. Among excipients useful in eye drops are viscosifying or gelling agents, to minimize loss by lacrimation through improved retention in the eye.

Liquid dosage forms for oral or other administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Commercially available nebulizers for liquid formulations, including jet nebulizers and ultrasonic nebulizers are useful for administration. Liquid formulations can be directly nebulized and lyophilized powder can be nebulized after reconstitution. Alternatively, the compounds of the present invention can be aerosolized using a fluorocarbon formulation and a metered dose inhaler, or inhaled as a lyophilized and milled powder.

Dosage forms for topical or transdermal administration of an inventive pharmaceutical composition may include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, cutaneous routes of administration are achieved with aqueous drops, a mist, an emulsion, or a cream.

Transdermal patches may have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions for rectal or vaginal administration may be suppositories which can be prepared by mixing the compounds of the present invention with suitable non-irritating excipients or carriers such as cocoa butter, polyethylene glycol or a suppository wax which are solid at ambient temperature but liquid at body temperature and therefore melt in the rectum or vaginal cavity and release the active agent(s). Alternatively, contemplated formulations can be administered by release from a lumen of an endoscope after the endoscope has been inserted into a rectum of a subject.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

EXAMPLES

Examples are provided below to further illustrate different features of the present invention. The examples also illustrate useful methodology for practicing the invention. These examples do not limit the claimed invention.

General Procedures

Tangential Flow Filtration (TFF) was used to purify the polymer products of the invention. TFF was performed with a Pall Minimate™ Capsule and Minimate™ TFF system according to the manufacturer's instructions. Either a Minimate TFF Capsule with 5 kDa Omega membrane (5K) or Minimate TFF Capsule with 10 kDa Omega membrane (10K) cartridge was used for purification. In all cases, the permeate was discarded and the retentate lyophilized to yield the polymer product. Structures of products were confirmed by $^1$H NMR, small molecules were also characterized by MS. Polymer weights reported in the examples were not corrected for water content.

Carbamoylfumagillol and chloroacetylcarbamoylfumagillol can be prepared according to the methods disclosed in U.S. Pat. No. 5,166,172 (Kishimoto, et al., incorporated herein by reference). p-Nitrophenyl fumagill-6-yl carbonate can be prepared according to published procedures. (See Han, C. et al. Biorg. Med. Chem. Lett. 2000, 10, 39-43). MA-GFLG-ONp can be prepared according to the methods disclosed in U.S. Pat. No. 5,258,453 (Kopecek et al. incorporated herein by reference.)

Synthesis of poly(HPMA-co-MA-GFLG-ONp)

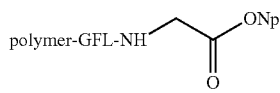

A mixture of hydroxypropylmethacrylamide (HPMA, 22.16 g, 155 mmol), N-methyacryl-gly-phe-leu-gly p-nitrophenyl ester (MA-GFLG-ONp, 10.00 g, 17.19 mmol), AIBN (1.484 g, 9.037 mmol) and acetone (225 g) was degassed (freeze, pump, thaw, 4 cycles). The resulting reaction mixture was stirred at 50° C. for 48 hours, then cooled to room temperature. The desired product was purified by trituration with acetone, then dried under vacuum to yield 17.6 g of poly(HPMA-co-MA-GFLG-ONp) as a white solid. The structure was verified by $^1$H NMR and the product shown to be free from substantial impurities (e.g., p-nitrophenol). Based on UV absorbance, the copolymer contained 0.47 mmoles of p-nitrophenyl ester per gram of polymer. The copolymer of this example is used in most of the subsequent examples. A wide range of copolymers based on different monomers and/or monomer ratios may be made following this procedure by adjusting the stoichiometry and/or using different monomers.

Synthesis of poly(HPMA-co-MA-GFLG-OH)

Poly(HPMA-co-MA-GFLG-ONp) (700 mg) was added portionwise to a solution of 0.1 M NaOH (11.3 mL) at 0° C. The yellow reaction mixture was stirred at 0° C. for 0.5 hours, then at room temperature for 4 hours. One-half of the solution was acidified with 0.1 M HCl to pH=6. The aqueous phase was extracted with ethyl acetate to remove excess p-nitrophenol. The aqueous phase was lyophilized to afford poly(HPMA-co-MA-GFLG-OH) as a colorless solid (360 mg).

Synthesis of poly(HPMA-co-MA-GG-ONp)

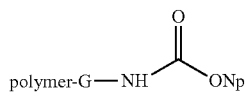

A mixture of hydroxypropylmethacrylamide (HPMA, 82.5 g), N-methyacryl-gly-gly p-nitrophenyl ester (MA-GG-ONp, 16.8 g), AIBN (5.7 g) and acetone (875 g) was sparged with argon for 90 min. The resulting reaction mixture was stirred at 50° C. for 48 hours, then cooled to room temperature. The desired product was purified by trituration with acetone, then dried under vacuum to yield 69.3 g of poly (HPMA-co-MA-GG-ONp) as a white solid. The structure was verified by $^1$H NMR and the product shown to be free from substantial impurities (e.g., p-nitrophenol). The amount of p-nitrophenyl ester per gram of polymer may be determined by UV absorbance. A wide range of copolymers based on different monomers and/or monomer ratios may be made following this procedure by adjusting the stoichiometry and/or using different monomers.

Synthesis of Poly(HPMA-Co-MA-GFLG-NHCH$_2$CH$_2$N(Me)BOC) and General Procedure A.

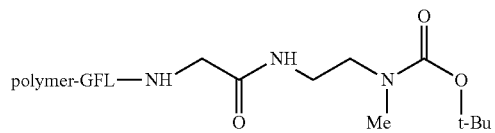

A solution of poly(HPMA-co-MA-GFLG-ONp) (1.0 g, 0.534 mmol) in DMF (6 mL) and H$_2$O (10 mL) was added dropwise over a 15 minute interval to a solution of tert-butyl N-(2-aminoethyl)-N-methylcarbamate (0.20 g, 1.15 mmol) in water (20 mL) at 0° C. The reaction mixture was stirred at 0° C. for 15 minutes, then warmed to room temperature and stirred for 12 hours. The solvents were evaporated under reduced pressure. The resulting residue was dissolved in water (50 mL), the pH was adjusted to approximately 8.0 with 0.1 M NaOH. The solution was filtered through a VacuCap filter, then purified using TFF (10 K). The polymer-containing solution was washed (as part of the TFF process) with 25 mM NaCl solution (800 mL) to remove p-nitrophenol, the pH of the solution was adjusted to approximately 4 with 0.1 M HCl, and then washed (as part of the TFF process) with water (400 mL). The polymer solution was lyophilized to isolate the compound poly (HPMA-co-MA-GFLG-NHCH$_2$CH$_2$N(Me)BOC) as a pale yellow solid (720 mg, 71%).

Synthesis of Fmoc-Phe-Gly-NH—(CH$_2$)$_6$NH—Boc:

To a solution of Fmoc-Phe-Gly-OH (0.66 g) in anhydrous THF (20 mL) at 0° C. under N$_2$ was added N,N'-dicyclohexylcarbodiimide (0.307 g) and 1-hydroxybenzotriazole hydrate (0.201 g). After stirring for 15 min, N-Boc-1,6-diaminohexane (0.322 g) was added. The reaction mixture was allowed to warm to RT and stirred overnight. Solids were filtered off and they were washed with EtOAc. The filtrate and washings were then concentrated under reduced pressure. The resulting residue was purified by flash column chromatography (0 to 10% MeOH in CH$_2$Cl$_2$) to afford Fmoc-Phe-Gly-NH—(CH$_2$)$_6$NH-Boc as a white solid (0.9 g).

Synthesis of Fmoc-Phe-Gly-NH—(CH$_2$)$_6$NH$_2$.TFA:

Fmoc-Phe-Gly-NH—(CH$_2$)$_6$NH-Boc (0.7 g) was dissolved in CH$_2$Cl$_2$ (4 mL) at 0° C. under N$_2$ and then trifluoroacetic acid (TFA) (4 mL) was added. The reaction mixture was allowed to warm to RT and stirred for 2 hours under N$_2$. The solvents were removed under reduced pressure and the residue dried at high vacuum to provide 0.71 g of Fmoc-Phe-Gly-NH(CH$_2$)$_6$—NH2.TFA. This crude material was used to prepare without further purification.

Synthesis of Fmoc-Phe-Gly-NH(CH$_2$)$_6$NH—CO-Fumagillol:

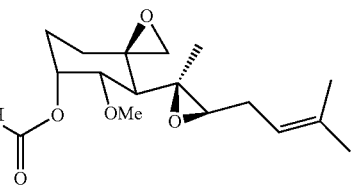

To a 0° C. solution of compound Fmoc-Phe-Gly-NH(CH$_2$)$_6$—NH2.TFA (0.71 g) in anhydrous CH$_2$Cl$_2$ (20 mL) and DMF (1 mL) under N$_2$ was added nitrophenyl fumagill-6-yl carbonate (0.536 g). Diisopropylethylamine (DIPEA) (0.74 mL) was then added. The reaction mixture was allowed to warm to RT and then stirred overnight at the same temperature. The solvents were removed under reduced pressure and the resulting residue was dissolved in EtOAc (70 mL). The EtOAc was washed with water and brine. The ethyl acetate solution was then dried over MgSO$_4$, filtered and concentrated under reduced pressure. The residue was purified by flash column chromatography (0 to 10% MeOH in CH$_2$Cl$_2$) to provide Fmoc-Phe-Gly-NH—(CH$_2$)$_6$NH—CO-fumagillol as an off white solid (0.81 g)

Synthesis of H-Phe-Gly-NH(CH$_2$)$_6$NH—CO-fumagillol

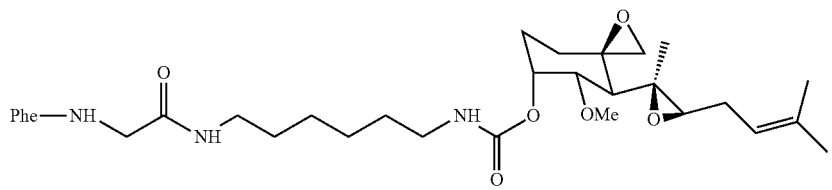

To a 0° C. solution of compound Fmoc-Phe-Gly-NH—(CH$_2$)$_6$NH—CO-fumagillol (0.80 g) in anhydrous CH$_2$Cl$_2$ (20 mL) under N$_2$ was added DBU (0.15 g). The reaction mixture was allowed to warm to RT. The solvent was removed under reduced pressure and the resulting residue was purified by flash column chromatography (0 to 10% MeOH in CH$_2$Cl$_2$) to provide H-Phe-Gly-NH—(CH$_2$)$_6$NH—CO-fumagillol as a pale yellow gum (0.45 g, 76%).

Synthesis of poly[HPMA-co-MA-GGFG-N-(6-aminohexyl)carbamoylfumagillol] and General Procedure B

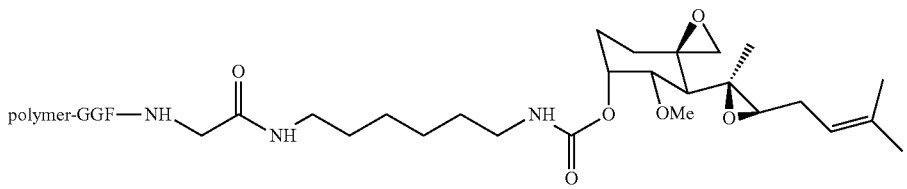

To a solution of poly(HPMA-co-MA-GG-ONp) (0.68 g) in anhydrous DMF (12 mL) at 0° C. under N$_2$ was added H-Phe-Gly-NH(CH$_2$)$_6$NHCO-fumagillol (0.45 g) in anhydrous DMF (5 mL) followed by the addition of diisopropylethylamine (DIPEA) (0.25 mL). The reaction mixture was allowed to warm to RT and after stirring overnight under N$_2$, 3-amino-1-propanol (0.032 g) was added. The mixture was allowed to stir for an additional hour. The solvent was removed under reduced pressure and the resulting residue was dissolved in 300 mL of distilled water and extracted with EtOAc (4×). A saturated aqueous NaCl solution (50 mL) was used to facilitate the phase separation. Traces of EtOAc were removed from the polymer solution by stirring under a flow of nitrogen gas. The polymer solution was filtered through a vacu cap filter (pH=5.56), concentrated to 30 mL by TFF with a 10K capsule and washed with water (700 mL) by TFF. The polymer was then lyophilized to provide the desired polymer conjugate poly[HPMA-co-MA-GGFG-N-(6-aminohexyl)carbamoylfumagillol] as a light pink foam (0.685 g). The spiroepoxide content was measured by reaction with 2-mercaptopyrimidine and determined to be 0.4 mmol/g.

Synthesis of Poly[HPMA-Co-MA-GGLG-N-(6-aminohexyl)carbamoylfumagillol]

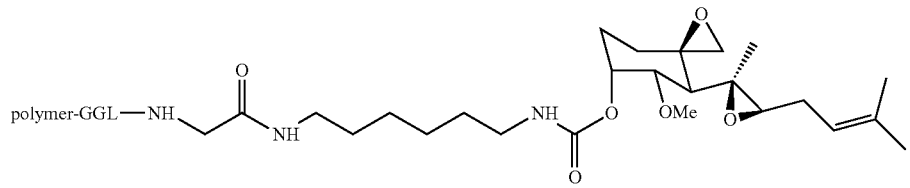

Using standard techniques, the dipeptide H-Leu-Gly-NH(CH$_2$)$_6$NHCO-Fum was prepared and coupled to poly(HPMA-co-MA-GG-ONp) using General Procedure B.

Synthesis of Poly[HPMA-Co-MA-GGVG-N-(6-aminohexyl)carbamoylfumagillol]

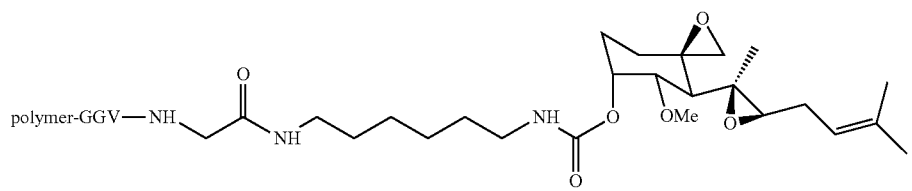

Using standard techniques, the dipeptide H-Val-Gly-NH(CH$_2$)$_6$NHCO-Fum was prepared and coupled to poly(HPMA-co-MA-GG-ONp) using General Procedure B.

Synthesis of poly[HPMA-co-MA-GGGG-N-(6-aminohexyl)carbamoylfumagillol]

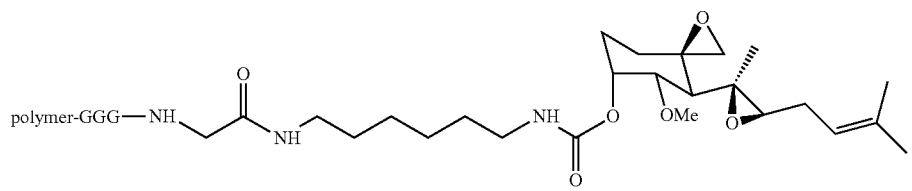

Using standard techniques, the dipeptide H-Gly-Gly-NH(CH$_2$)$_6$NHCO-Fum was prepared and coupled to poly(HPMA-co-MA-GG-ONp) using General Procedure B.

Synthesis of poly[HPMA-co-MA-GFLG-N-(cis-4-aminocyclohexyl)carbamoylfumagillol] via poly[HPMA-co-MA-GFLG-N-(cis-4-aminocyclohexylamine.HCl)]

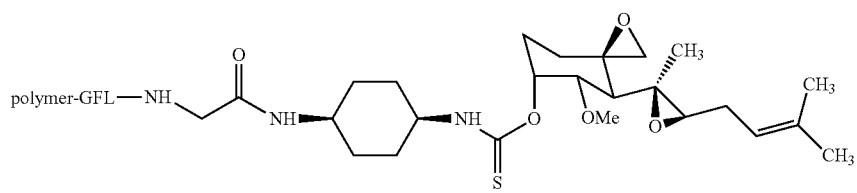

General Procedure C was followed using cis-1,4-diaminocyclohexane (0.914 g) and poly(HPMA-co-MA-GFLG-ONp) (1.5 g) to yield poly[HPMA-co-MA-GFLG-N-(cis-4-aminocyclohexylamine.HCl)] as an off-white solid (1.08 g).

General procedure F was followed using poly[HPMA-co-MA-GFLG-N-(cis-4-aminocyclohexylamine.HCl)] (0.98 g), p-nitrophenyl fumagill-6-yl carbonate (0.465 g) and DIEA (0.268 g) in DMF 16 mL. The solvent was evaporated and the solution diluted with water. The aqueous phase (500 mL total) was extracted with ethyl acetate (80 mL total) and purified by TFF using an additional 350 mL of water. The retentate was diluted with water, extracted with ethylacetate and lyophilized to yield poly[HPMA-co-MA-GFLG-N-(cis-4-aminocyclohexyl)carbamoylfumagillol] as a light pink solid (0.79 g).

$^1$H NMR (DMSO-d6): δ 7.90-8.35 (m, 4H, amide-NH), 7.0-7.70 (m, 25H, Phenylalanine and amide-NH), 5.26 (m, H-5-Fum), 5.18 (bt, alkene-Fum), 4.60-4.90 (m, 14H), 4.50-4.60 (m, 1H, phenylalanine alpha proton), 4.10-4.30 (m, 1H, leucine alpha proton), 3.40-3.80 (m, 21H), 3.26 (s, 3H, OMe-Fum), 2.80-3.10 (m, 31H), 2.17 (m, 2H, allylic-Fum), 0.37-2.0 [m, 166H {1.69 (s, 3H, Fum-Me), 1.59 (s, 3H, Fum-Me), 1.07 (s, 3H, Fum-Me)}].

Synthesis of poly(HPMA-co-MA-GFLG-NHCH$_2$CH$_2$NH$_2$HCl) and General Procedure C for the Reaction of Diamines with Poly(HPMA-Co-MA-GFLG-ONp)

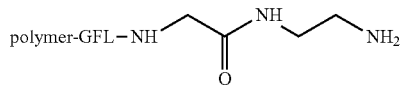

A solution of ethylenediamine (0.33 g, 5.49 mmole) in water (20 mL), pH 11.7, was adjusted to pH 9.1 by the addition of 37% aq HCl (17-18 drops). The solution was cooled in an ice bath and poly(HPMA-co-MA-GFLG-ONp) (1.03 g) in DMF (6 mL) was added dropwise over 20 minutes while maintaining the temperature below 4° C. The solution was stirred 20 minutes at 4° C., 50 minutes at room temperature to give a lemon yellow solution, pH 8.1. The solution was evaporated at 40° C. H$_2$O (3×10 mL) was added and evaporated. The product was diluted with water (60 mL), the solution adjusted with NaOH to pH 8.0. The solution was filtered through a VacuCap filter and purified by TFF as follows. The polymer solution was first washed with 25 mM NaCl solution (800 mL) to remove p-nitrophenol. The solution was washed with water (400 mL) then adjusted to pH 4 with 0.1 M HCl. The TFF retentate was collected and the filter was washed with 2×10 mL of water. The combined retentate and washes gave a polymer solution which was lyophilized to isolate the compound poly(HPMA-co-MA-GFLG-NHCH$_2$CH$_2$NH$_2$.HCl) as a pale yellow solid (0.71 g, 72%).

Synthesis of N-[(2R)-hydroxy-2-methylbutan-2-yl]carbamoylfumagillol and General Procedure D

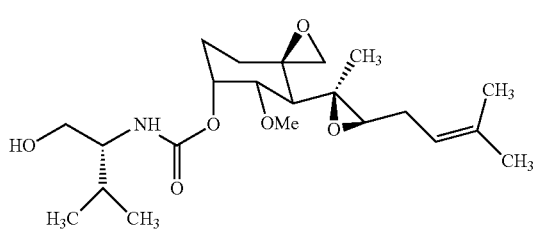

A solution of p-nitrophenyl fumagill-6-yl carbonate (400 mg, 0.89 mmol) and (R)-2-amino-3-methyl-1-butanol (280 mg, 2.71 mmol) were stirred in ethanol (10 mL) at room temperature for 12 hours. The yellow solution was concentrated and the residue purified by flash chromatography (methanol/methylene chloride) to yield N-[(2R)1-hydroxy-2-methylbutan-2-yl]carbamoylfumagillol (340 mg, 0.83 mmol) as a colorless oil.

Synthesis of N-(6-hydroxyhexyl)carbamoylfumagillol

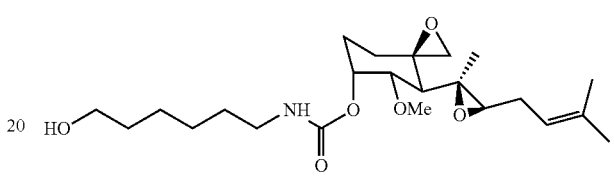

General Procedure D was followed using p-nitrophenyl fumagill-6-yl carbonate (150 mg) in ethanol (10 mL) and 6-aminohexanol (48 mg). The product was isolated as a colorless oil (110 mg, 78%).

Synthesis of N-[1-(hydroxymethyl)cyclopentyl]carbamoylfumagillol

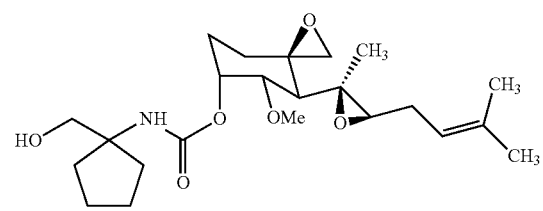

General Procedure D was followed using p-nitrophenyl fumagill-6-yl carbonate (100 mg) in ethanol (3 mL) and THF (1 mL) and cycloleucinol (52 mg) to afford N-[1-(hydroxymethyl)cyclopentyl]carbamoylfumagillol as an oil (50 mg).

Synthesis of N-(1-hydroxy-2-methylpropan-2-yl)carbamoylfumagillol

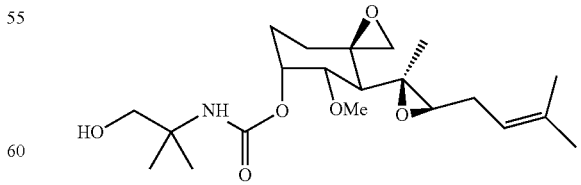

General Procedure D was followed using p-nitrophenyl fumagill-6-yl carbonate (100 mg) in ethanol (3 mL) and THF (2 mL) and 2-amino-2-methylpropanol (40 mg) to afford N-(1-hydroxy-2-methylpropan-2-yl)carbamoylfumagillol as an oil (37 mg).

Synthesis of fumagill-6-yl (2S)-2-(hydroxymethyl)pyrrolidine-1-carboxylate

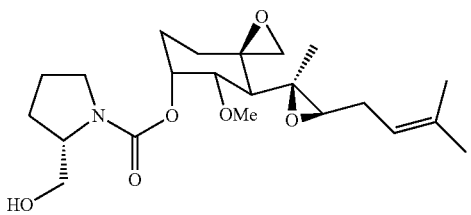

General procedure D was followed. The S-prolinol (68 mg, 0.67 mmol) was reacted with p-nitrophenyl fumagill-6-yl carbonate (150 mg, 0.335 mmol) in ethanol (4 mL) The product was purified by flash chromatography (methanol/methylene chloride) to yield fumagill-6-yl (2S)-2-(hydroxymethyl)pyrrolidine-1-carboxylate as a white foam (81 mg, 63%).

Synthesis of N-(6-aminohexyl)carbamoylfumagillol

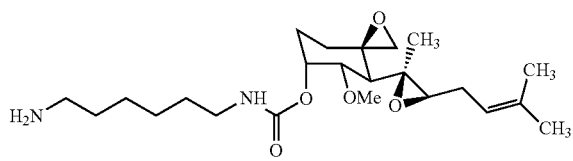

A solution of 1,6-diaminohexane (0.13 g) in methanol (8 mL) was cooled to 0° C. and p-nitrophenyl fumagill-6-yl carbonate (0.13 g) in methanol (2 mL) was added dropwise. The solvent was reduced to about 2 mL by rotary evaporation. Ethyl acetate was added and the organic phase was washed with water, 0.1 N NaOH, water, brine and dried with sodium sulfate. The solvent was evaporated and the residue dissolved in ethanol (15 mL). DL-tartaric acid (16 mg) was added, the solution was stored overnight and then evaporated to about 0.5 mL. Ether was added and a white solid formed. The solid was collected by filtration, washed with ether and dried to yield the tartrate salt of N-(6-aminohexyl)carbamoylfumagillol (74 mg).

Synthesis of Fumagill-6-yl[trans-(4-aminocyclohexyl)]carbamate

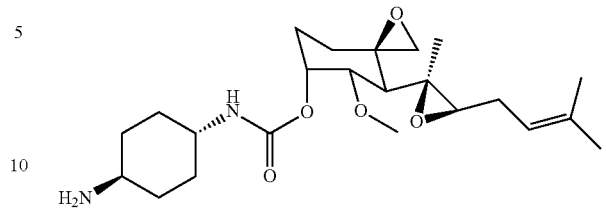

To a solution of trans-1,4-diaminocyclohexane (1.3 g) in methanol (80 ml) at 0-5° C. was added over 30 min a solution of fumagill-6-yl 4-nitrophenyl carbonate (1.0 g) in methanol (20 ml) and $CH_2Cl_2$ (20 ml) and then stirred for 30 minutes. After concentration to 20 ml on a rotavap and dilution with ethyl acetate (75 ml) the organic layer was washed with water (30 ml), 0.1 N NaOH (30 ml), water and brine (30 ml), dried ($MgSO_4$) and concentrated under reduced pressure to give 0.78 g of a solid. This was dissolved in ethanol (80 ml) and DL-tartaric acid (127 mg) was added. After 1 hour a solution formed which was allowed to stand overnight before being concentrated under reduced pressure to remove virtually all the ethanol. MTBE (100 ml) was added and concentrated followed by MTBE (30 ml). The solids were collected by filtration and washed with MTBE (2×10 ml) and dried under vacuum to give fumagill-6-yl[trans-(4-aminocyclohexyl)]carbamate hemitartrate (0.73 g); m.p. 180-185° C.

Synthesis of poly[HPMA-co-MA-GFLG-NH(CH$_2$)$_6$NH$_2$.HCl]

General Procedure C was followed using 1,6-diaminohexane (621 mg, 5.36 mmol) and poly(HPMA-co-MA-GFLG-ONp) (1.0 g). The crude product was purified by TFF (5 K) using aqueous NaCl (25 mM) and then acidified to pH 4.0 with 0.1 M HCl and further purified by TFF with water to yield poly[HPMA-co-MA-GFLG-NH(CH$_2$)$_6$NH$_2$.HCl] as an off-white solid (860 mg).

Synthesis of p-nitrophenyl N-[(2R)1-hydroxy-2-methylbutan-2-yl]carbamoylfumagill-6-yl carbonate and General Procedure E

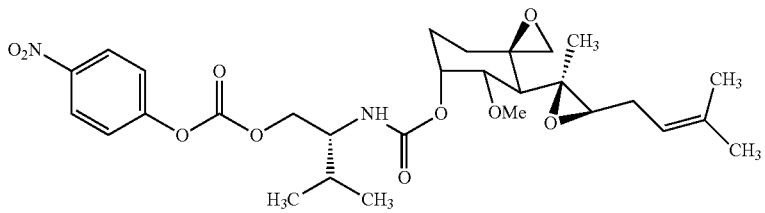

To a solution of the alcohol N-[(2R)1-hydroxy-2-methylbutan-2-yl]carbamoylfumagillol (1.11 g) in methylene chloride at 0° C. under $N_2$ was added DMAP (660 mg, 5.40 mmol) followed by the portionwise addition of p-nitrophenyl chloroformate (810 mg). The reaction mixture was stirred at 0° C. for 1 hour. The solvent was evaporated and the resulting residue was dissolved in EtOAc and washed with water, brine and dried ($Na_2SO_4$). Evaporation of EtOAc provided the crude product, which was purified by flash chromatography (silica, eluting with 100% hexanes and then with 2-30% EtOAc). The fractions containing pure product were combined and evaporated to isolate N-[(2R)1-(p-nitrophenolcarbonylhydroxy-2-methylbutan-2-yl]carbamoylfumagillol (1.25 g, 80%) as a white solid.

Synthesis of N-[1-(p-nitrophenoxycarbonylhy-droxymethyl)-2-methylpropan-2-yl)carbamoylfum-agillol

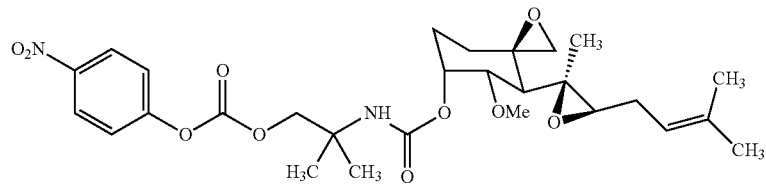

Following General Procedure E, dimethylalcohol (60 mg), p-nitrophenyl fumagill-6-yl carbonate (46 mg), and DMAP (37 mg) were reacted in methylene chloride (8 mL). The reaction mixture was diluted with ethyl acetate and washed with water (3×) and then brine. The organic phase was dried (Na$_2$SO$_4$) and evaporated to a yellow foam (87 mg) which was used without further purification.

Synthesis of N-[1-(p-nitrophenoxycarbonylhydroxymethyl) cyclopentyl]carbamoylfumagillol

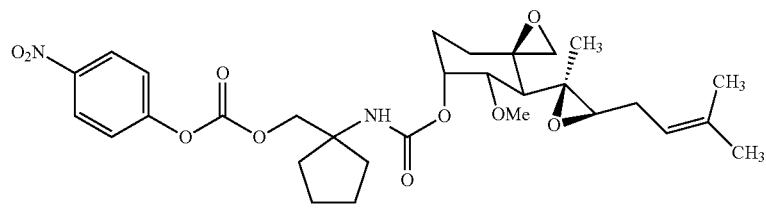

Following General Procedure E, N-[1-(hydroxymethyl) cyclopentyl]carbamoylfumagillol (product from Example 14, 74 mg), p-nitrophenyl chloroformate (53 mg), and DMAP (43 mg) were reacted in methylene chloride (5 mL). After the extractive workup, N-[1-(p-nitrophenoxycarbonyl-hydroxymethyl)cyclopentyl]carbamoylfumagillol (100 mg) was used without further purification.

Synthesis of poly[HPMA-co-MA-GFLG-NH(CH$_2$)$_6$ NHcarbamoyl-[1-hydroxy-3-methylbutan-2-yl]car-bamoylfumagillol] and General Procedure F

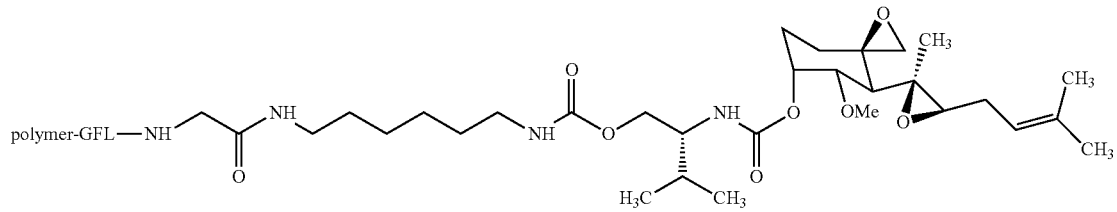

To a solution of polymer (400 mg) and p-nitrophenyl N-[(2R)1-hydroxy-3-methylbutan-2-yl]carbamoylfumagill-6-yl carbonate (240 mg) in DMF (8 mL) at 0° C. was added DIEA (0.11 g) dropwise. The solution was stirred at 0° C. for one hour and allowed to warm to room temperature. After 3 days, the solvent was evaporated and water (80 mL) was added. The aqueous phase was extracted with ethyl acetate (500 mL total) until none of the starting carbonate was detectable by MS. The aqueous phase was purified by TFF (10 K) and the retentate lyophilized to yield the conjugate as a white solid (380 mg, 77%).

$^1$H NMR (DMSO-d6): δ 8.25 (bs, 2H, amide-NH), 8.0 (bs, 1H, amide-NH), 7.70 (bs, 2H, amide-NH), 7.10-7.30 (m, 15H, Phenylalanine and amide-NH), 7.10 (bt, 1H, NH-Fum), 6.92 (bd, 1H, NH-Fum), 5.26 (m, H-5-Fum), 5.18 (bt, alkene-Fum), 4.50-4.80 (m, 1H, phenylalanine alpha proton), 4.0-4.21 (m, 1H, leucine alpha proton), 3.50-3.84 (m, 19H), 3.29 (s, 3H, OMe-Fum), 2.80-3.10 (m, 28H), 2.51 (d, 1H, J=4.4 Hz, H-2-Fum), 2.19 (m, 2H, allylic-Fum), 0.82-1.92 [m, 131H {1.84 (m, 2H, Fum), 1.72 (s, 3H, Fum-Me), 1.60 (s, 3H, Fum-Me), 1.09 (s, 3H, Fum-Me), 0.84 (dd, 6H, Fum-isopropyl}].

Synthesis of poly[HPMA-co-MA-GFLG-N-(2-aminoethyl)carbamoylfumagillol]

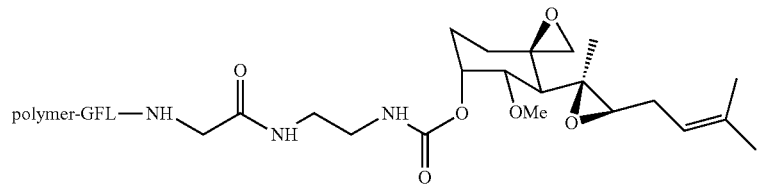

General procedure F was followed using poly(HPMA-co-MA-GFLG-NHCH$_2$CH$_2$NH$_2$.HCl) (200 mg), p-nitrophenyl fumagill-6-yl carbonate (100 mg) and DIEA (57 mg) in DMF (10 mL). The product was purified by TFF (10 K) with water and lyophilized to yield the conjugate as a pale yellow solid (160 mg).

Synthesis of poly[HPMA-co-MA-GFLG-N(Me)-(2-methylaminoethyl)carbamoylfumagillol]

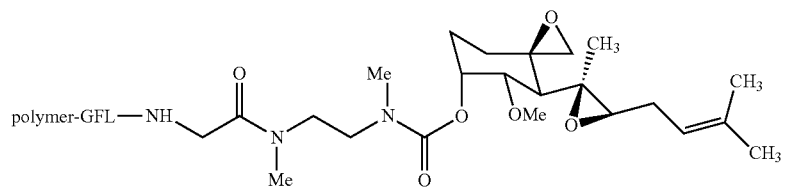

General procedure F was followed using poly(HPMA-co-MA-GFLG-N(Me)CH$_2$CH$_2$NHMe.HCl) (200 mg), p-nitrophenyl fumagill-6-yl carbonate (100 mg) and DIEA (57 mg) in DMF (5 mL). The product was purified using TFF (10 K) with water and lyophilized to yield the conjugate as an off-white solid (180 mg).

Synthesis of poly(HPMA-co-MA-GFLG-N-(2-aminoethyl)carbamoyldihydrofumagillol

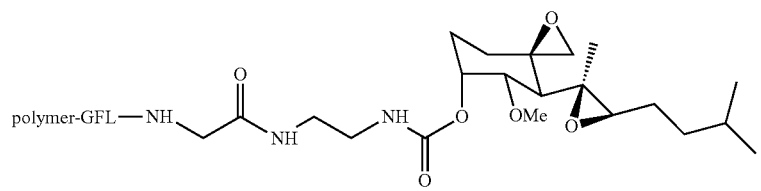

General procedure F was followed using poly(HPMA-co-MA-GFLG-NHCH$_2$CH$_2$NH$_2$.HCl) (200 mg), p-nitrophenyl dihydrofumagill-6-yl carbonate (200 mg) and DIEA (57 mg) in DMF (10 mL). The product was purified by TFF (10 K) with water (150 mL) and lyophilized to yield poly(HPMA-co-MA-GFLG-N-(2-aminoethyl)carbamoyldihydrofumagillol as a pale yellow solid (160 mg).

Synthesis of poly[HPMA-co-MA-GFLG-N-(3-aminopropyl)carbamoylfumagillol]

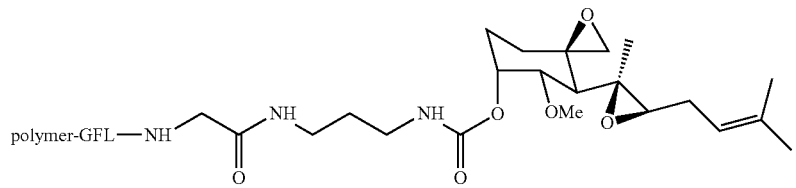

General procedure F was followed using poly(HPMA-co-MA-GFLG-NHCH$_2$CH$_2$CH$_2$NH$_2$.HCl) (220 mg), p-nitrophenyl fumagill-6-yl carbonate (110 mg) and DIEA (63 mg) in DMF (6 mL). The solvent was evaporated and the resulting solution diluted with water. The aqueous phase was extracted with ethyl acetate and purified by TFF using 350 mL of water. The retentate was lyophilized to yield poly [HPMA-co-MA-GFLG-N-(3-aminopropyl)carbamoylfumagillol] as a light pink powder (200 mg).

Synthesis of poly[HPMA-co-MA-GFLG-N-(6-aminohexyl)carbamoylfumagillol]

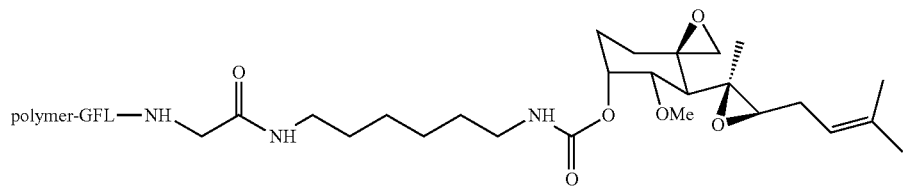

General procedure F was followed using poly[HPMA-co-MA-GFLG-N-(trans-4-aminocyclohexylamine.HCl)] (1.0 g), p-nitrophenyl fumagill-6-yl carbonate (0.48 g) and DIEA (0.27 g) in DMF (25 mL). The solvent was evaporated and the solution diluted with water. The aqueous phase (300 mL) was extracted with ethyl acetate (700 mL total) and purified by TFF using an additional 350 mL of water. The retentate was lyophilized to yield poly[HPMA-co-MA-GFLG-N-(4-aminocyclohexyl)carbamoylfumagillol] as a light pink solid (0.9 g).

$^1$H NMR (DMSO-d6): δ 8.10-8.35 (m, 3H, amide-NH), 7.90-8.10 (m, amide-NH), 7.05-7.32 (m, 22H, amide-NH) 5.27 (m, H-5-Fum), 5.18 (bt, alkene-Fum), 4.60-4.90 (m, 14H), 4.50-4.60 (m, 1H, phenylalanine alpha proton), 4.10-4.30 (m, 1H, leucine alpha proton), 3.40-3.80 (m, 21H), 3.27 (s, 3H, OMe-Fum), 2.80-3.20 (m, 33H), 2.56 (d, 1H, H=3.90 Hz, H-2-Fum), 2.18 (m, 2H, allylic-Fum), 0.37-2.0 [m, 147H {1.70 (s, 3H, Fum-Me), 1.60 (s, 3H, Fum-Me), 1.07 (s, 3H, Fum-Me)}].

Synthesis of poly[HPMA-co-MA-GFLG-N-(trans-4-aminocyclohexyl) carbamoylfumagillol]

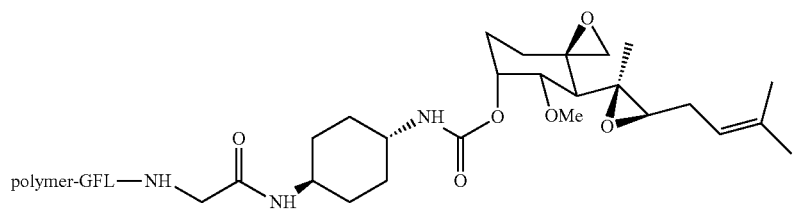

General procedure F was followed using poly[HPMA-co-MA-GFLG-N-(trans-4-aminocyclohexylamine.HCl)] (1.0 g), p-nitrophenyl fumagill-6-yl carbonate (0.48 g) and DIEA (0.27 g) in DMF 25 mL. The solvent was evaporated and the solution diluted with water. The aqueous phase (300 mL) was extracted with ethyl acetate (700 mL total) and purified by TFF using an additional 350 mL of water. The retentate was lyophilized to yield poly[HPMA-co-MA-GFLG-N-(3-aminohexyl)carbamoylfumagillol] as a light pink solid (0.9 g).

$^1$H NMR (DMSO-d6): δ 7.90-8.35 (m, 4H, amide-NH), 7.0-7.70 (m, 25H, Phenylalanine and amide-NH), 5.26 (m, H-5-Fum), 5.18 (bt, alkene-Fum), 4.60-4.90 (m, 14H), 4.50-4.60 (m, 1H, phenylalanine alpha proton), 4.10-4.30 (m, 1H, leucine alpha proton), 3.40-3.80 (m, 21H), 3.26 (s, 3H, OMe-Fum), 2.80-3.10 (m, 31H), 2.17 (m, 2H, allylic-Fum), 0.37-2.0 [m, 166H {1.69 (s, 3H, Fum-Me), 1.59 (s, 3H, Fum-Me), 1.07 (s, 3H, Fum-Me)}].

Synthesis of poly[HPMA-co-MA-GFLG-N-[2-(4-aminophenyl)ethyl]carbamoylfumagillol]

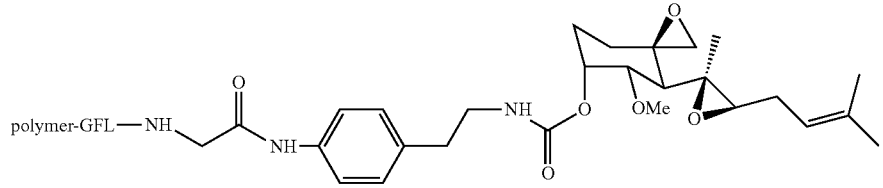

To a suspension of poly[HPMA-co-MA-GFLG-OH] (200 mg), N-[2-(4-aminophenyl)ethyl]carbamoylfumagillol] (100 mg) and DIEA (75 mg) in DMF (6 mL) at 0° C. was added EDCI (total 44 mg) in portions. The solution was allowed to warm to room temperature and stirred overnight. The solvent was evaporated, the residue was suspended in water and the suspension extracted with EtOAc (7 times, total 250 mL). The aqueous phase was purified by TFF (10 K) using water (350 mL). The retentate was lyophilized to afford the polymer as a white fluffy solid (170 mg).

Synthesis of poly[HPMA-co-MA-GFLG-NH-2-[(2-(2-aminoethoxy)ethoxy)ethyl]carbamoylfumagillol]

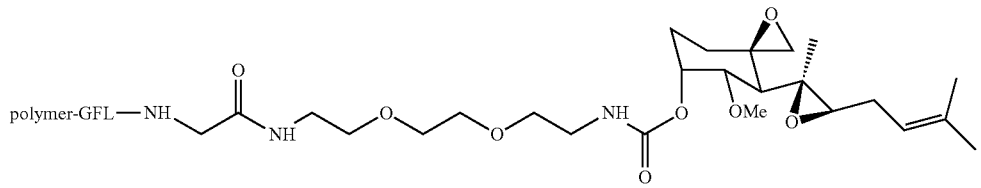

To a solution of 2,2'-(Ethylenedioxy)bis(ethylamine) (0.79 g, 5.34 mmol) in distilled water (20 mL) at 0° C. (pH=11.56) was added conc. HCl until pH of the solution was 9.01 (measured by pH meter). Poly(HPMA-co-MA-GFLG-ONp) (1.0 g, 0.534 mmol) in DMF (6 mL) and H$_2$O (10 mL) was added to the amine-containing solution dropwise over a period of 15 minutes and the reaction mixture was stirred at 0° C. for 15 minutes. The reaction mixture was then allowed to warm to room temperature and stirred for 2 hours. The pH of the solution was measured to be 8.15. The reaction mixture was diluted with distilled water (300 mL) and filtered through a VacuCap filter, reaction flask was washed with water (100 mL). The polymer solution was concentrated to 40 mL by TFF (10 K) and was washed with 25 mM NaCl (800 mL) to remove p-nitrophenol, the pH was then adjusted to 4 with 0.1 M HCl and finally washed with water (400 mL). The pure polymer solution was lyophilized to isolate poly[HPMA-co-MA-GFLG-NH-2-[2-(2-aminoethoxy)ethoxy]ethylamine.HCl] as a pink solid (800 mg, 78%).

To a mixture of p-nitrophenyl fumagill-6-yl carbonate (93 mg, 0.208 mmol) and poly[HPMA-co-MA-GFLG-N-2-[(2-(2-aminoethoxy)]ethoxy)ethylamine.HCl] (200 mg, 0.104 mmol) in anhydrous DMF (5 mL) at 0° C. under N₂ was added DIEA (57 mg, 0.416 mmol). The reaction mixture was allowed to warm to room temperature and stirred for 12 hours. The solvent was removed under reduced pressure and the resulting residue was suspended in water (30 mL) and extracted with EtOAc (aqueous and organic phases from the emulsion formed were separated using centrifuge) to remove excess of p-nitrophenyl fumagill-6-yl carbonate and p-nitrophenol. Nitrogen was passed through the aqueous solution to remove traces of EtOAc and it was purified using TFF (5K) by washing it with water (150 mL) to remove DIEA hydrochloride. The polymer solution was lyophilized to obtain the desired polymer conjugate poly[HPMA-co-MA-GFLG-N-2-[2-(2-aminoethoxy)ethoxyethyl]carbamoylfumagillol] (220 mg, 95%) as an off-white solid.

Synthesis of poly[HPMA-co-MA-GFLG-NH-(6-aminodecyl)carbamoylfumagillol]

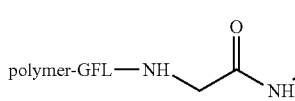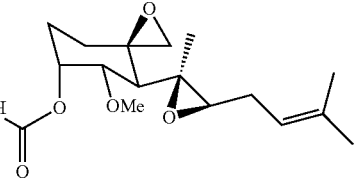

To a mixture of p-nitrophenyl fumagill-6-yl carbonate (300 mg, 0.67 mmol) and poly[HPMA-co-MA-GFLG-N-10-[decylamine.HCl] (300 mg, 0.15 mmol; made in a similar manner to Example 33 except 1,10-diaminodecane was used as the amine) in anhydrous DMF (6 mL) at 0° C. under N₂ was added DIEA (83 mg, 0.64 mmol). The reaction mixture was allowed to warm to room temperature and stirred for 12 hours. The solvent was removed under reduced pressure and the resulting residue was suspended in water (30 mL) and extracted with EtOAc (aqueous and organic phases from the emulsion formed were separated using a centrifuge) to remove excess of p-nitrophenyl fumagill-6-yl carbonate and p-nitrophenol. Nitrogen was passed through the aqueous solution to remove traces of EtOAc. The crude aqueous solution was purified using TFF (10K) by washing with water (150 mL) to remove DIEA hydrochloride. The polymer solution was lyophilized to obtain the desired polymer conjugate poly[HPMA-co-MA-GFLG-NH-(10-aminodecyl)carbamoylfumagillol] (300 mg, 87%) as an off-white solid.

Synthesis of N-(2-acetamidoethyl)carbamoylfumagillol

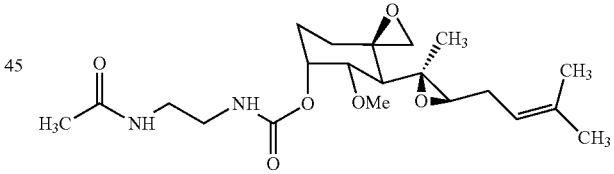

To a solution of p-nitrophenyl fumagill-6-yl carbonate (200 mg) in ethanol (5 mL) at 0° C. was added N-(2-aminoethyl)acetamide (0.132 mL). The solution was stirred at 0° C. for one hour and overnight at room temperature. The reaction was diluted with ethyl acetate, washed with water. The aqueous phase was back extracted with ethyl acetate and the combined organic phases dried (MgSO₄). The crude product was purified by flash chromatography. The product was a yellow solid (120 mg).

Synthesis of the Following Compound

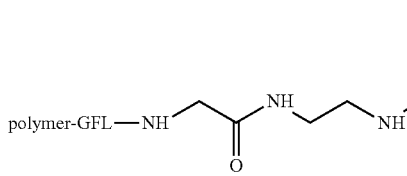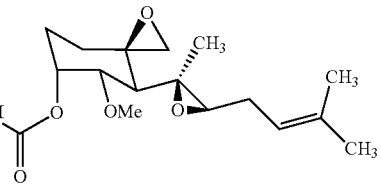

To a solution of poly(HPMA-co-MA-GFLG-NHCH$_2$CH$_2$NH$_2$—HCl) (200 mg) and N-(5-carboxypentyl)carbamoylfumagillol (96 mg) in DMF (6 mL) at 0° C. was added DIEA (104 mg) followed by N-(3-dimethylaminopropyl)-N'-ethylcarbodiimide hydrochloride (42 mg). The solution was allowed to warm to RT and stirred overnight. The solvent was evaporated and the residue dissolved in water (50 mL) and extracted with ethyl acetate (200 mL). The aqueous phase was purified by TFF with water (450 mL). The retentate was lyophilized to yield the polymer (200 mg) as a pale yellow solid.

Synthesis of the Following Compound

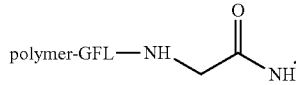
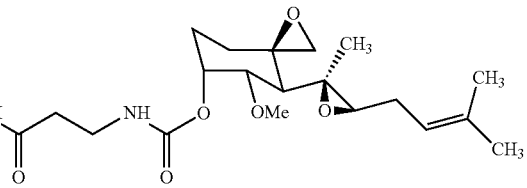

To a solution of poly[HPMA-co-MA-GFLG-N(CH$_2$)$_6$NH$_2$.HCl] (216 mg), 2-carboxyethylcarbamoylfumagillol (91 mg) in DMF (8 mL) at 0° C. was added DIEA (118 mg) followed by N-(3-Dimethylaminopropyl)-N'-ethylcarbodiimide hydrochloride (88 mg). The solution was allowed to warm to room temperature and stirred overnight. The solvent was evaporated and the residue dissolved in water (50 mL) and extracted with ethyl acetate (200 mL). The aqueous phase was purified by TFF (10 K) with water (1 L). The retentate was lyophilized to yield the polymer (170 mg) as a pale yellow solid.

Synthesis of the Following Compound

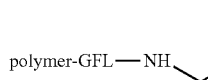
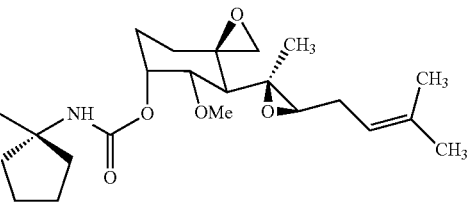

General Procedure F was followed using poly(HPMA-co-MA-GFLG-NHCH$_2$CH$_2$CH$_2$NH$_2$HCl) (220 mg) and carbonate (Example 24, 100 mg) in DMF (6 mL) with DIEA (63 mg). The reaction was extracted with ethyl acetate. Following TFF (10 K) purification with water, and lyophilization, the product was isolated as a light pink powder (140 mg).

BocNHCH$_2$CH$_2$N(Me)CH$_2$C(O)NHC(O)$_2$-fumagill-6-yl (Alkylation of N—BOC, N'-methylethylenediamine with chloroacetylcarbamoylfumagillol)

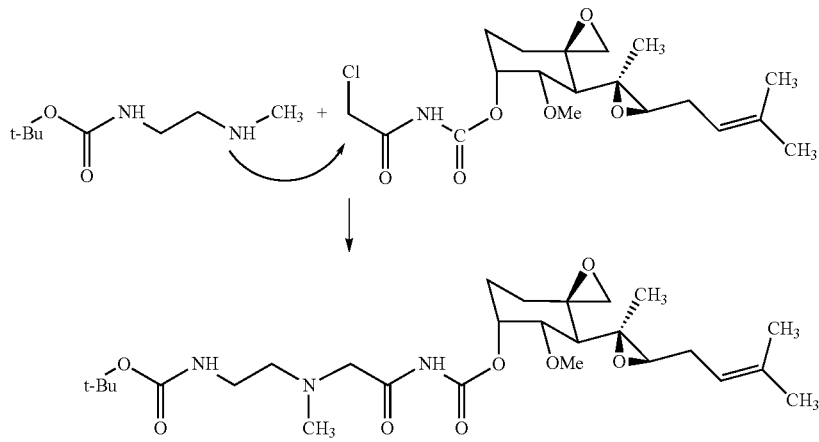

A solution of TNP-470 (0.2 g) and DIEA (0.105 g) in DMF (3 mL) was cooled to 0° C. A solution of tert-butyl N-[2-(methylamino)ethyl]carbamate (0.105 g) in DMF (3 mL) was added, and the mixture was stirred for 3 hours at 0° C. and then overnight. The reaction was diluted with ethyl acetate and extracted with water. The aqueous phase was back extracted with ethyl acetate, and the combined organic phases were extracted with brine, dried (MgSO$_4$) and evaporated to afford an oil. Purification by silica gel chromatography (methanol/methylene chloride) and evaporation of the product fractions gave BocNHCH$_2$CH$_2$N(Me)CH$_2$C(O)NHC(O)$_2$-fumagill-6-yl a white foam (0.16 g, 60%).

Reaction of tert-butyl N-[2-aminoethyl]carbamate with chloroacetylcarbamoylfumagillol

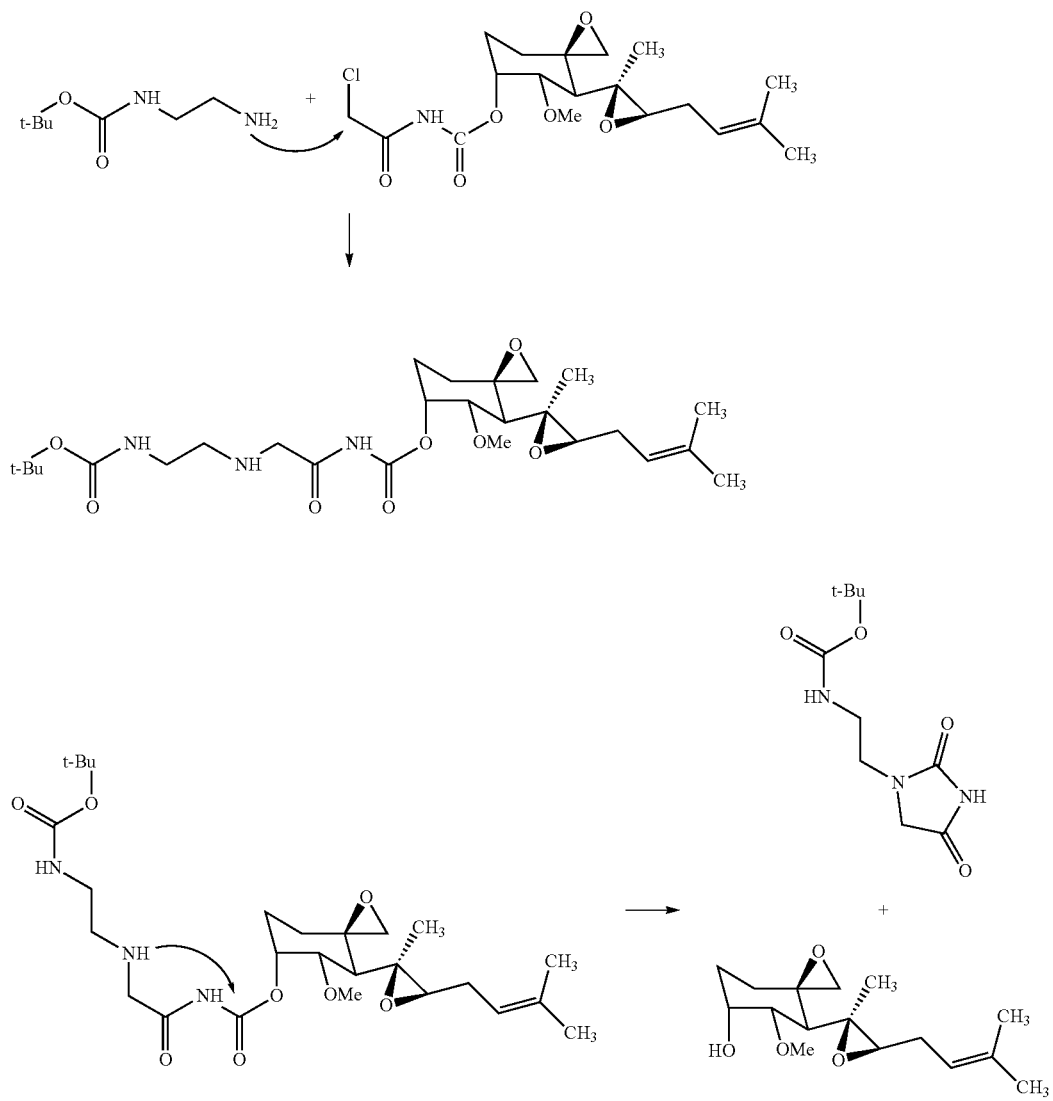

A 30 uL aliquot of a 1 M solution of Boc-ethylenediamine in DMF was added to DMF (270 uL). The solution was cooled to 0° C., and a solution of TNP-470 (48 mg) in DMF (600 uL) was added dropwise over 2 minutes. The reaction was monitored by LC/MS. The largest amount of the desired alkylation product observed was 34%. Carbamoylfumagillol was also produced. The ratio of desired product to carbamoylfumagillol was 1.0 to 0.4. Attempted isolation of the desired product resulted in the isolation of hydantoin and fumagillol. Thus, the desired product could not be isolated because of the rate of decomposition. Thus TNP-470 could not be alkylated according to the described method.

In Vivo Testing DIO C57Bl6 Mice—Weight Changes, Food Consumption, Body Composition C57Bl6 male mice (N=6) thirteen weeks old with an average of weight of 34 g were ad libitum fed TD.06414 a high fat diet composed of 60% Kcal from fat (Harlan diet). On study day 1 animals were randomized into groups so that the average weight of each group was 33.9 g. The mice were treated with either phosphate buffered saline (vehicle), TNP-470, or Compound 16 (dorsal, subcutaneous administration). Treatment was continued for 31 days at the doses and on the schedule shown in the Table below. Animals were weighed every other day. Food consumption was measured weekly. On day 33 gross pathology was performed to determine body composition.

FIG. 1 compares the weight loss in an obese DIO mouse following treatment with a fumagillol-conjugate compound of the present invention (Compound 16) or TNP-470 (synthetic fumagillin analog) at varying doses/regimens as recited in Table 2.

TABLE 2

| Body Weight Day 33 | Dose mg/kg/day | Dose* | Schedule | Drug |
|---|---|---|---|---|
| 39.6 | 0 | 0 | qod | Vehicle |
| 34.1 | 0.5 | 1.12 | qod | TNP-470 |
| 30.4 | 0.5 | 0.18 | qod | Compound 16 |
| 27.4 | 1.5 | 0.56 | q4d | Compound 16 |

*Daily Dose as micromoles/kg Fumagillol

The results in FIG. 1 show an increase in weight in the vehicle control group of 16% and a decrease in weight of 19% when administering Compound 16 in a q4d dosing regimen. Administration of compound 16 provides both therapeutic and prophylactic effects. Specifically, compound 16 induces or increases weight loss and it also prevents an increase in weight. Compound 16 is superior to TNP-470 in the degree of weight loss. Compound 16 is superior to TNP-470 in that fumagillol doses are reduced.

Table 3 compares the body fat composition in an obese DIO mouse following treatment with Compound 16 or TNP-470 at the varying doses/regimens described herein. Analysis was performed at Day 33 gross pathology. Total fat as a percentage of BW in the vehicle group was 13.2% while total fat in the groups treated with Compound 16 was 8.2% (1 mg/kg qod) or 5.6% (6 mg/kg q4d).

TABLE 3

| | Weights in grams, group averages | | | | | |
|---|---|---|---|---|---|---|
| | B.W. | Total Fat | Epididymal Fat | Inguinal Fat | Retroperitoneal Fat | Liver |
| Vehicle | 39.6 | 5.24 | 2.21 | 1.93 | 1.10 | 1.46 |
| TNP qod | 34.1 | 3.55 | 1.54 | 1.21 | 0.80 | 1.15 |
| Cmpd 16 1 mg/kg qod | 30.4 | 2.52 | 1.18 | 0.92 | 0.42 | 1.10 |
| Cmpd 16 6 mg/kg q4d | 27.4 | 1.55 | 0.78 | 0.53 | 0.23 | 1.17 |

Figure 2:
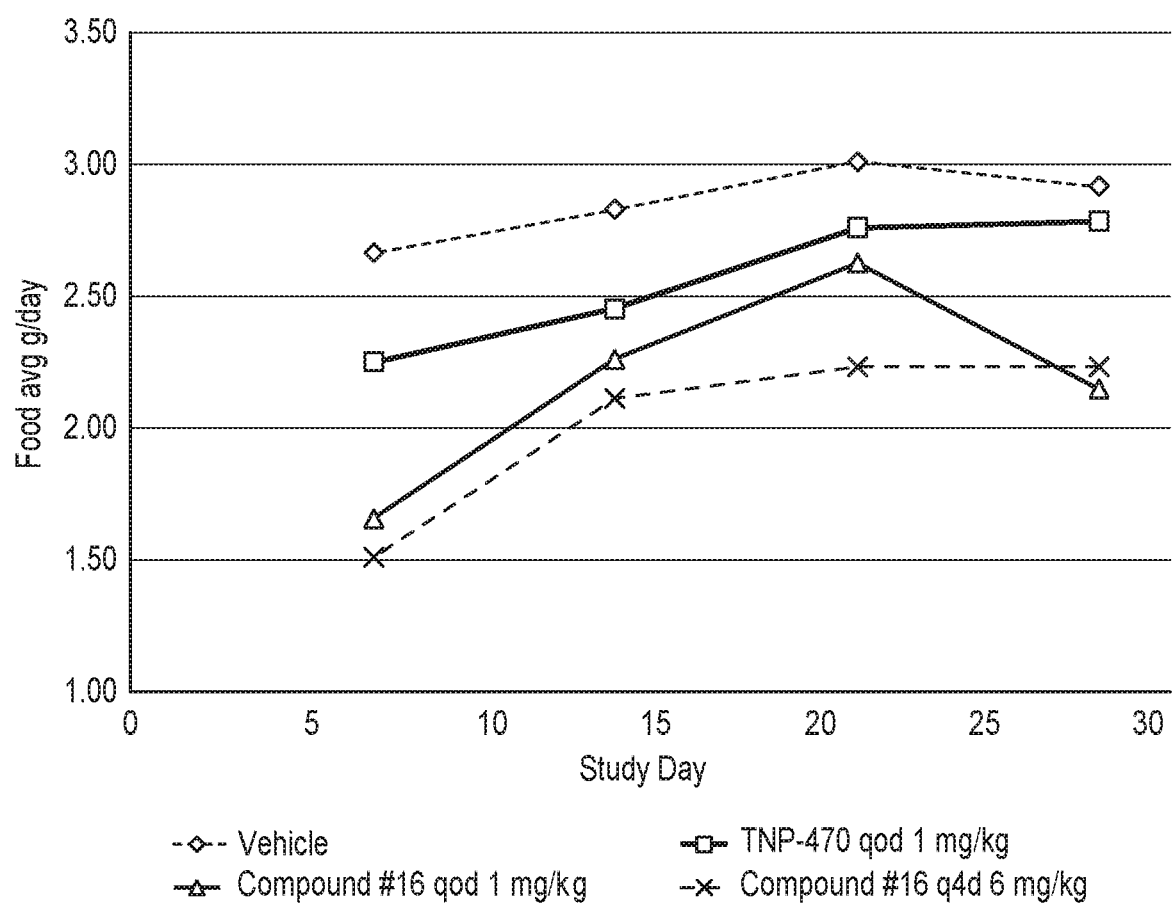
FIG. 2 is a graph showing average weekly food consumption following administration of compounds of the present invention.

FIG. 2 compares the average daily food consumption in an obese DIO mouse following treatment with Compound 16 or TNP-470 at varying doses/regimens. The results in FIG. 2 show decrease food consumption following treatment with Compound 16 and Compound 16 causes a greater reduction in food consumption than TNP-470.

Figure 3:
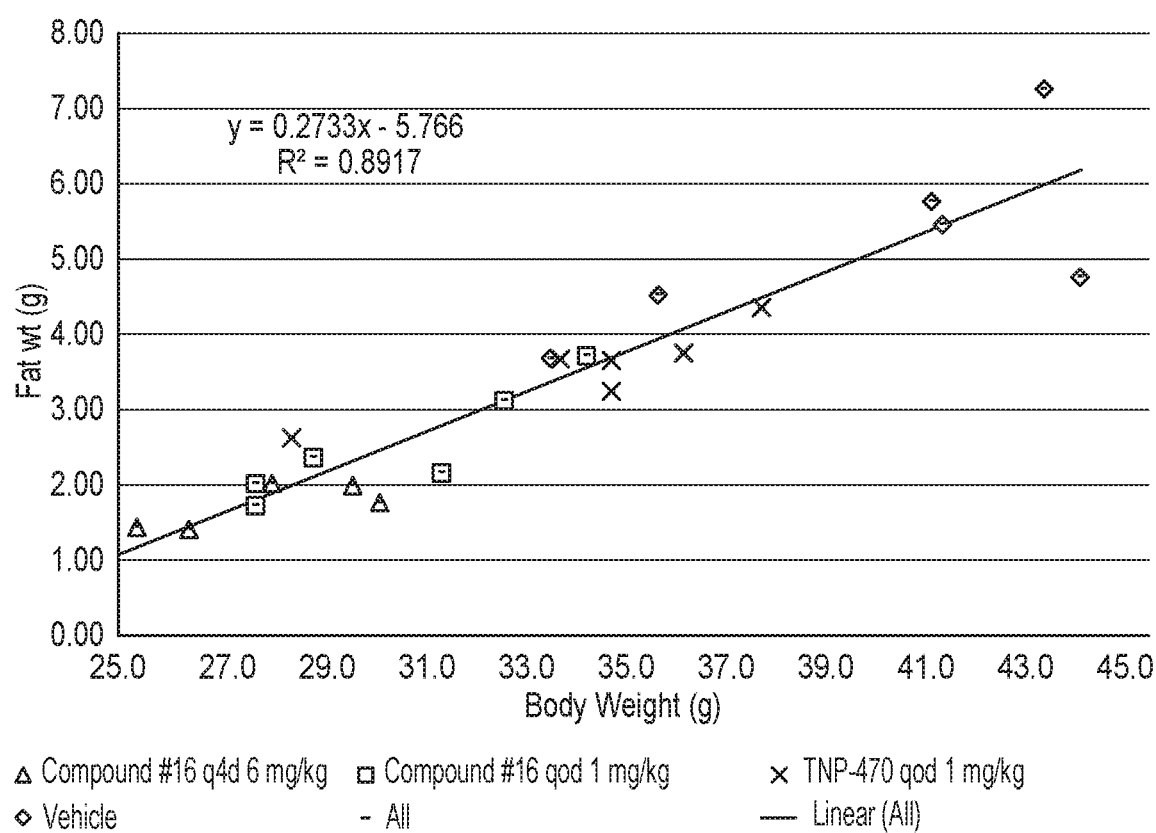
FIG. 3 is a graph showing the relationship between total fat weight and body weight following administration of compounds of the present invention.

FIG. 3 compares the body composition (fat v. body weight) in an obese DIO mouse following treatment with Compound 16 or TNP-470 at varying doses/regimens. The results in FIG. 3 show that the amount of body weight lost is directly correlated to fat loss.

In Vivo Testing DIO C57Bl6 Mice—Weight Changes, Food Consumption, Glucose Tolerance and Body Composition Dose Response C57Bl6 male mice (N=6) fifteen weeks old with an average of weight of 42 g were ad libitum fed TD.06414 a high fat diet composed of 60% Kcal from fat (Harlan diet). On study day 1 animals were treated with either phosphate buffered saline (vehicle), or Compound 16 at various doses (dorsal, subcutaneous administration). Treatment was continued for 29 days at the doses and on the schedule shown in the Table below. Animals were weighed every other day. Food consumption was measured weekly. On day 24 (mice had been most recently treated with Compound 16 on day 21) an overnight fasted IP-Glucose Tolerance Test (GTT) was administered to the vehicle group and the four Compound 16 treatment groups. Each animal was weighed and a baseline fasted glucose measurement collected. Each animal was given a 1 gram per kilogram dose of dextrose as a 25% solution by intraperitoneal injection. Blood glucose levels were measured at 15 minutes, 30 minutes, 60 minutes, 90 minutes and 120 minutes after IP administration of glucose (via tail vein blood samples by using an Alpha-TRAK blood glucose monitoring system (including glucose meter and test strips) from Abbott Laboratories, (North Chicago, Ill., USA). The AlphaTRAK meter displays results between 20 and 750 mg/dL (1.1-41.7 mmol/L). On day 32 (mice had been most recently dosed on day 29) animals were fasted for three hours, weighed, blood collected by cardiac puncture and gross pathology was performed to determine body composition. Blood analysis was performed by Idexx laboratories. Blood glucose was 278, 290, 265, 259 and 227 mg/dL for doses of 0, 0.2, 0.6, 2.0 and 6.0 respectively. BUN was 21.8, 22.0, 19.7, 15.3, and 16.5 for doses of 0, 0.2, 0.6, 2.0 and 6.0 respectively.

Figure 4:
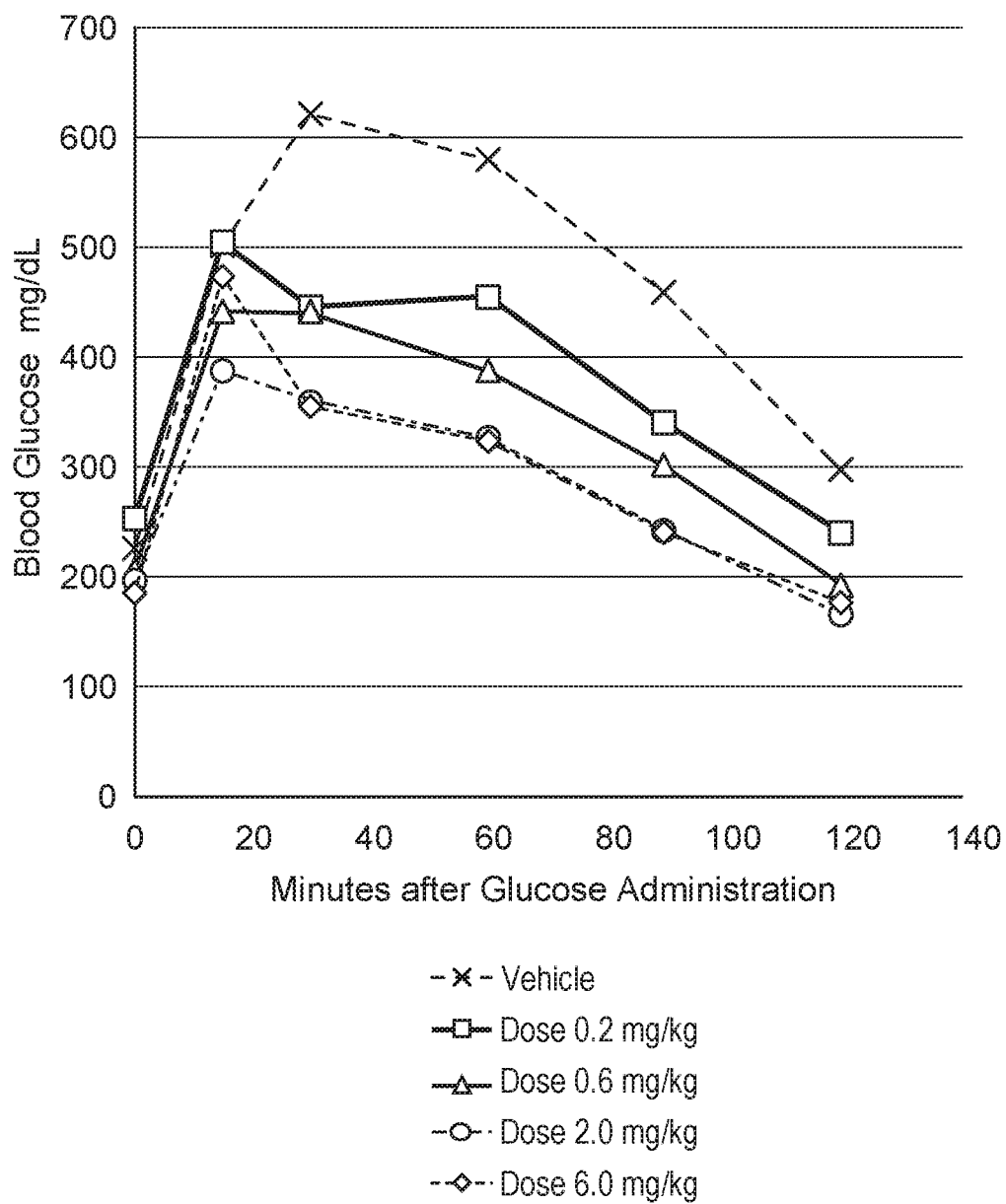
FIG. 4 is a graph showing blood glucose levels following administration of a glucose challenge during the treatment period of a murine study using compounds of the present invention.

Table 4 shows the blood glucose level as a function of time and the dose of Compound 16. Table 4 shows that higher doses of Compound 16 result in lower blood glucose levels even at the lowest dose of 0.2 mg/kg; these results are displayed in FIG. 4.

| 4 Blood Glucose, Group averages | | | | | | | |
|---|---|---|---|---|---|---|---|
| Dose | Average | Blood Glucose mg/dL group average ± SEM | | | | | |
| mg/kg | BW (g) | Fasting | 15 min | 30 min | 60 min | 90 min | 120 |
| Vehicle - 0 | 43.0 | 226 ± 22.9 | 502 ± 30.3 | 621 ± 38.4* | 580 ± 48.7* | 459 ± 54.0 | 297 ± 33.7 |
| 0.2 | 43.4 | 254 ± 5.8 | 505 ± 33.9 | 446 ± 20.5 | 456 ± 25.9 | 341 ± 15.5 | 241 ± 16.8 |
| 0.6 | 40.9 | 206 ± 14.9 | 442 ± 50.0 | 441 ± 35.54 | 388 ± 56.7 | 302 ± 43.3 | 192 ± 12.9 |
| 2.0 | 36.8 | 198 ± 11.6 | 388 ± 20.7 | 361 ± 24.3 | 327 ± 26.7 | 244 ± 24.0 | 166 ± 6.4 |
| 6.0 | 33.0 | 185 ± 6.5 | 473 ± 39.1 | 355 ± 23.8 | 324 ± 19.1 | 240 ± 6.7 | 177 ± 9.3 |

*one mouse in each group had blood glucose >750 mg/dL; treated as equal to 750 mg/dL Table 5 shows that increasing doses of Compound 16 result in significant increases in weight loss at doses greater than 0.2 mg/kg q4d. Table 6 shows that doses of 2 mg/kg q4d and 6 mg/kg q4d were associated with significant reductions in food consumption relative to vehicle controls and that food consumption is dose-responsive. From day 9-29, the weekly food consumption in the 2 mg/kg group was 90% of vehicle while the food consumption in the 6 mg/kg group was 75% of vehicle.

TABLE 5

Body Weights Day 32

| Dose mg/kg | Group BW (g) ± SEM | Weight Change from day 1 | Fumagillol* |
|---|---|---|---|
| Vehicle - 0 | 45.7 ± 1.12 | +8.3% | 0.00 |
| 0.2 | 46.5 ± 0.65 | +10.5% | 0.02 |
| 0.6 | 43.3 ± 0.42 | +2.9% | 0.06 |
| 2.0 | 38.8 ± 0.70 | −7.4% | 0.18 |
| 6.0 | 33.6 ± 0.72 | −20.0% | 0.54 |

*micromoles/kg/day; dosing q4d

TABLE 6

Weekly food consumption, Group Averages

| Group | Day 1-8 Food (g) | Day 9-15 Food (g) | Day 15-22 Food (g) | Day 22-29 Food (g) |
|---|---|---|---|---|
| Vehicle | 22.4 | 23.3 | 22.4 | 21.5 |
| 0.2 mg/kg | 25.8 | 22.6 | 20.3 | 19.7 |
| 0.6 mg/kg | 19.5 | 21.5 | 20.2 | 18.4 |
| 2 mg/kg | 14.3 | 22.2 | 19.9 | 18.5 |
| 6 mg/kg | 9.0 | 17.5 | 17.8 | 16.1 |

Table 7 shows that adipose tissue is lost in preference to other tissues as the mice in the control group are about 13% fat while the mice in the 2 mg/kg q4d group and 6 mg/kg q4d group are 11% and 10% fat, respectively.

TABLE 7

Tissue weights day 32, group averages

| Dose mg/kg | avg B.W. (g) | avg Total Fat | Epid. Fat | Ing. Fat | RP Fat | Liver | Fat % BW |
|---|---|---|---|---|---|---|---|
| 0.0 | 45.70 | 5.88 | 1.88 | 2.65 | 1.35 | 2.00 | 12.9% |
| 0.2 | 46.50 | 6.02 | 2.01 | 2.54 | 1.48 | 2.06 | 13.0% |
| 0.6 | 43.32 | 6.01 | 2.24 | 2.51 | 1.26 | 1.75 | 13.9% |
| 2.0 | 38.82 | 4.42 | 1.72 | 1.81 | 0.89 | 1.44 | 11.4% |
| 6.0 | 33.60 | 3.25 | 1.11 | 1.54 | 0.60 | 1.30 | 9.7% |

Figure 5:
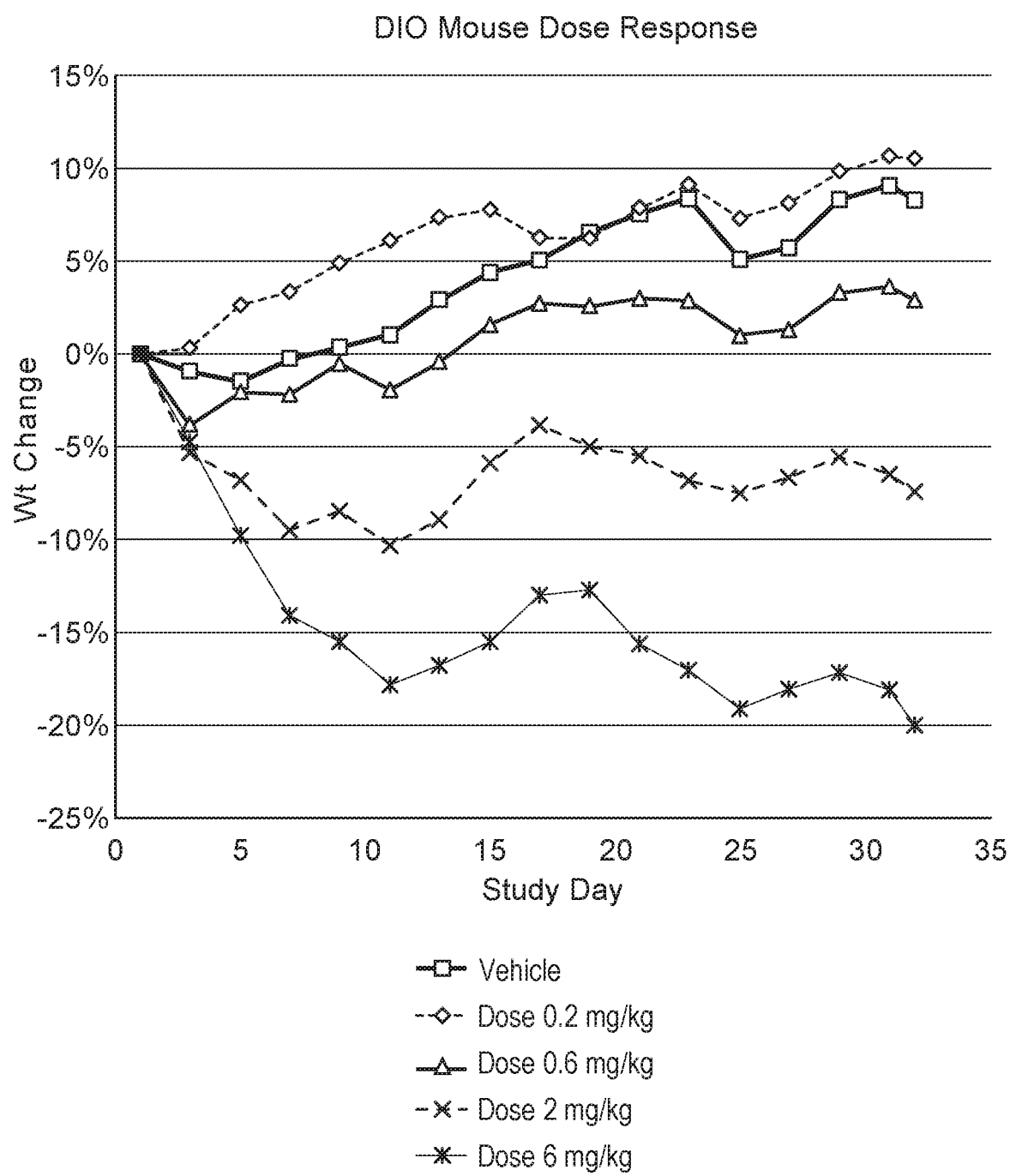
FIG. 5 is a graph showing body weight change over time following administration of various dosages of a compound of the present invention on a q4d dosing schedule.

The results in FIG. 5 show increasing weight loss following treatment with Compound 16 at doses greater than or equal to 0.6 mg/kg utilizing a q4d schedule. The weight loss is dose-responsive, higher doses cause greater weight loss.

Figure 6:
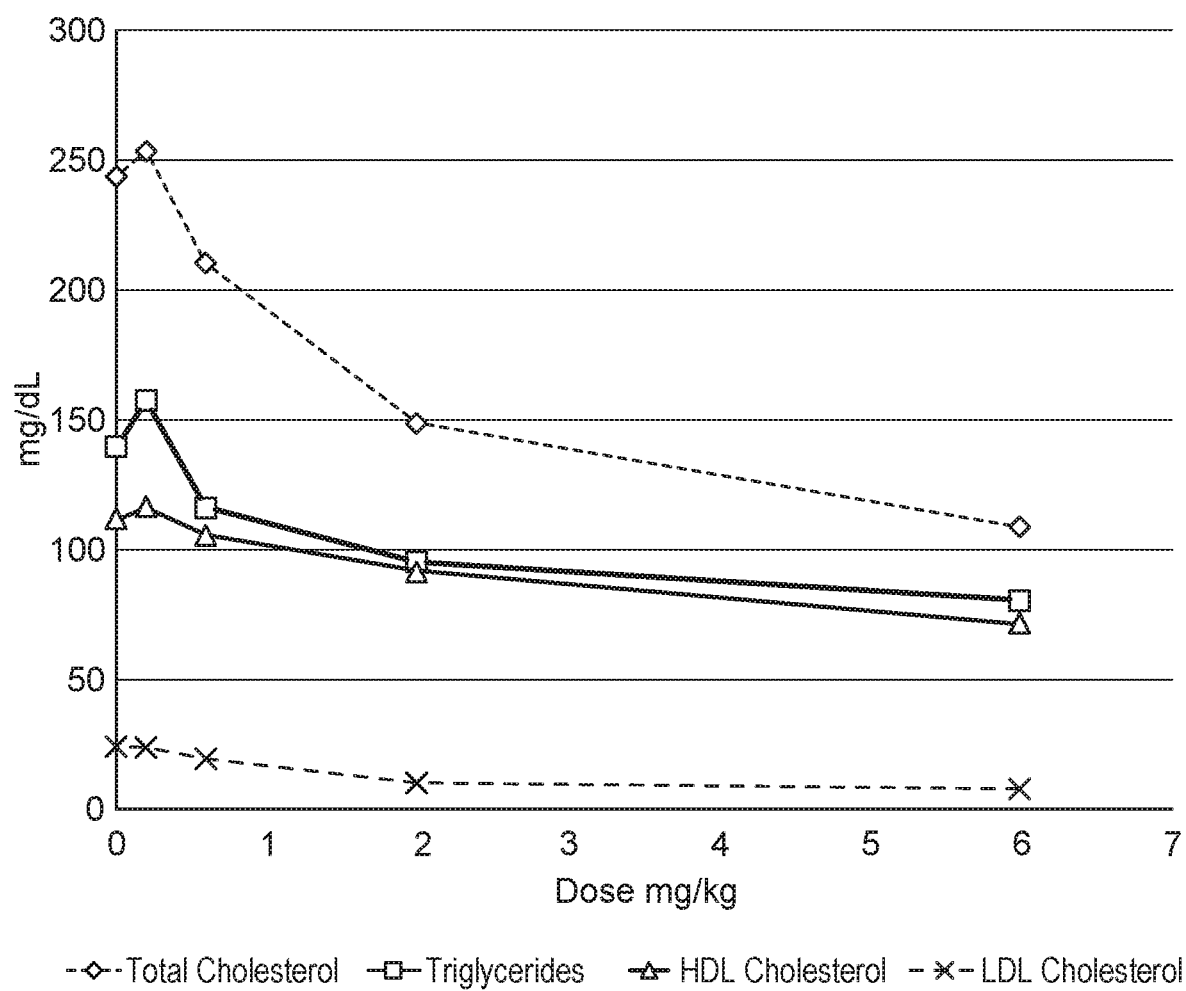
FIG. 6 is a graph showing changes in total cholesterol, triglycerides, HDL cholesterol and LDL cholesterol at the conclusion of a 32 day study as a function of dose level using compounds of the present invention.

The results in Table 8 show reductions in cholesterol, triglycerides, HDL, LDL and HDL/LDL ratios associated with increasing doses of Compound 16. These results are displayed in FIG. 6.

TABLE 8

Lipids in blood day 32

| Dose mg/kg | CHOLES-TEROL mg/dL | TRIGLYC-ERIDE mg/dL | HDL CHOLES-TEROL mg/dL | LDL mg/dL | HDL/LDL ratio |
|---|---|---|---|---|---|
| 0 | 244 ± 12.6 | 140 ± 7.7 | 112 ± 4.0 | 24 ± 2.2 | 4.8 ± 0.4 |
| 0.2 | 253 ± 8.4 | 158 ± 10.9 | 117 ± 2.7 | 24 ± 1.1 | 4.9 ± 0.2 |
| 0.6 | 210 ± 3.7 | 116 ± 3.1 | 106 ± 1.2 | 20 ± 0.3 | 5.4 ± 0.1 |
| 2 | 149 ± 4.7 | 95 ± 8.7 | 92 ± 2.6 | 10 ± 0.5 | 9.0 ± 0.4 |
| 6 | 109 ± 2.6 | 81 ± 13.6 | 72 ± 1.3 | 8 ± 0.5 | 9.0 ± 0.5 |

Values are ± SEM

The results in Table 9 show favorable changes in alkaline phosphatase, SGPT, SGOT and CPK associated with increasing doses of Compound 16.

TABLE 9

Blood enzyme analysis

| Dose mg/kg | ALKALINE PHOSPHATASE | SGPT (ALT) | SGOT (AST) | CPK |
|---|---|---|---|---|
| 0 | 61 ± 1.2 | 74 ± 11.2 | 72 ± 5.4 | 34 ± 2.5 |
| 0.2 | 51 ± 3.2 | 79 ± 16.8 | 77 ± 10.1 | 74 ± 18.5 |
| 0.6 | 44 ± 1.4 | 50 ± 2.3 | 57 ± 2.4 | 66 ± 11.3 |
| 2 | 43 ± 2.4 | 35 ± 3.1 | 53 ± 3.7 | 68 ± 17.8 |
| 6 | 36 ± 0.9 | 42 ± 5.9 | 59 ± 2.2 | 84 ± 13.3 |

EXAMPLE

Figure 10:
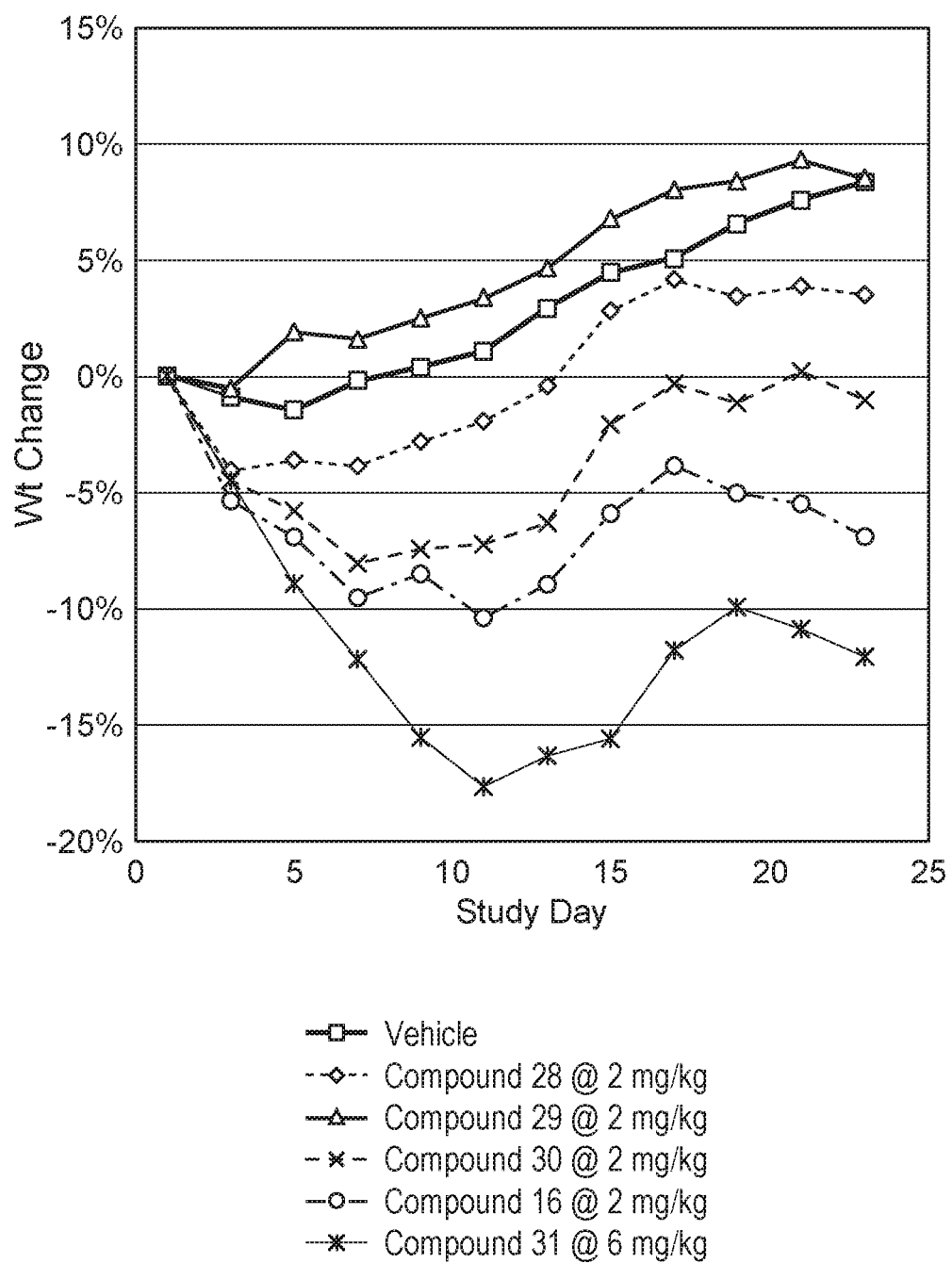
FIG. 10 is a graph showing body weight change over time following administration of various compounds of the present invention.

C57Bl6 male mice (N=6) fifteen weeks old with an average of weight of 42 g were ad libitum fed TD.06414 a high fat diet composed of 60% Kcal from fat (Harlan diet). On study day 1 animals were treated on a q4d schedule with either phosphate buffered saline (vehicle), or Compounds 16, 28, 29, or 30 at doses of 2 mg/kg or Compound 31 at 6 mg/kg (dorsal, subcutaneous administration). Animals were weighed every other day. FIG. 10 compares the weight loss in an obese DIO mouse following treatment for 23 days with various conjugates of the present invention. The results in FIG. 10 show that changes in the linker alone result in changes in the degree of weight loss.

EXAMPLE

Figure 7:
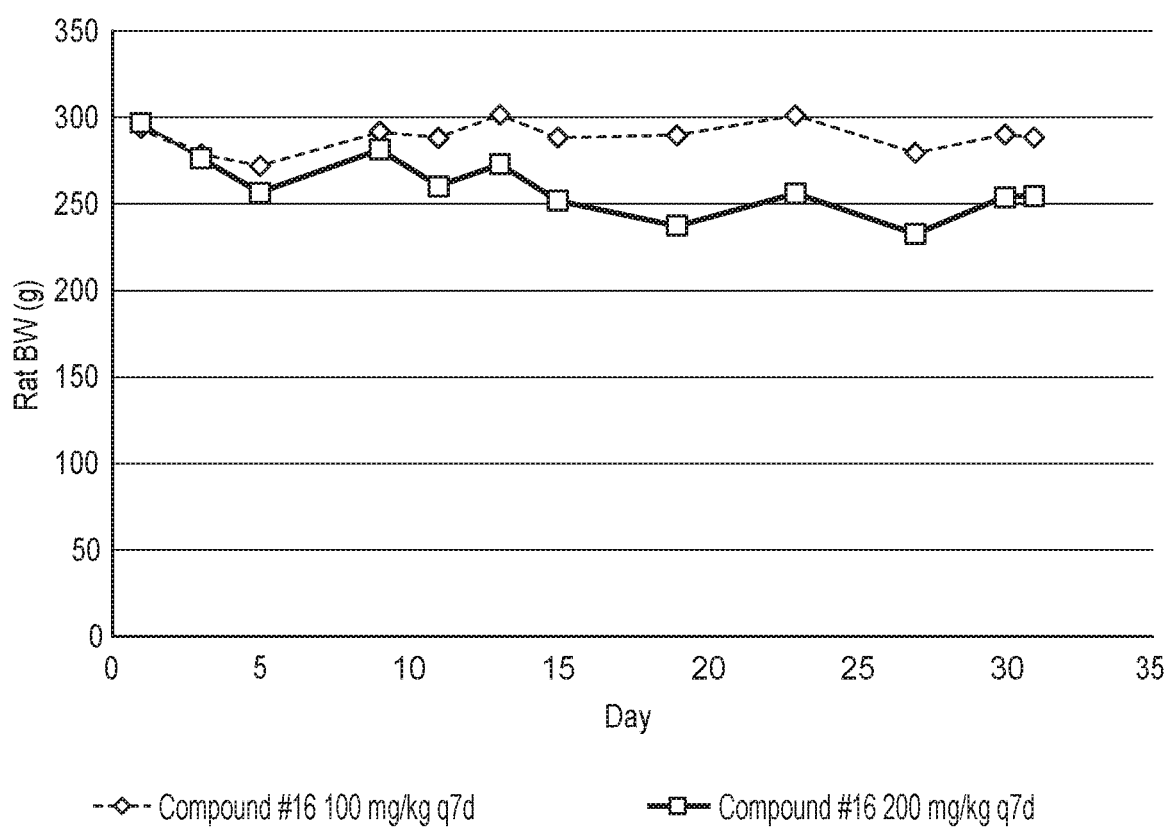
FIG. 7 is a graph showing body weight change over time following administration of various dosages of a compound of the present invention to rats on a q7d dosing schedule.
Figure 8:
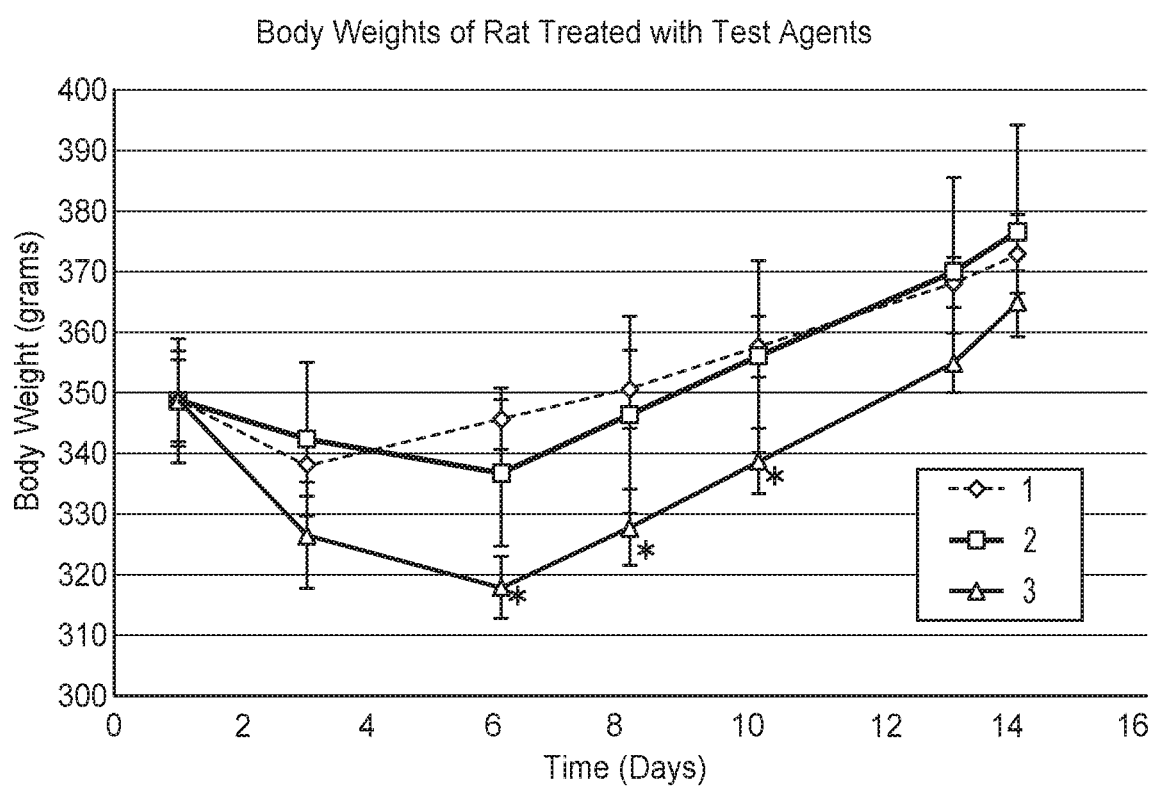
FIG. 8 is a graph showing the change in body weight of rats treated with a single dose of various test agents.

Sprague Dawley male rats (N=3) nine to ten weeks old with an average weight of 300 g were ad libitum fed standard rodent diet (PharmaServ lab diet 5001). FIG. 7—Rats were treated with Compound 16 at either 100 mg/kg or 200 mg/kg (IV, tail vein) on days 1, 8, 15, 22 and 29. The rats were weighed periodically and bled on day 10, day 17, day 24. For in-life blood collections, the rats were anesthetized with an inhalation mixture of 4% Isoflurane and 1.5% oxygen, then blood was collected via retro-orbital plexus puncture at a volume of at least 1 mL. On day 31 animals were weighed, blood collected by cardiac puncture and gross pathology was performed to determine body composition. Within the limits of comparison to normal ranges and pre-dose data, clinical findings for albumin, albumin/globulin ratio, alkaline, phosphatase, ALT (SGPT), AST (SGOT), bicarbonate, direct bilirubin, indirect bilirubin, total bilirubin, BUN, BUN/creatinine ratio, calcium, chloride, cholesterol, CK, creatinine, globulin, glucose, phosphorus, potassium, sodium, sodium/potassium ratio, total protein were unremarkable. Beyond weight loss and the other findings reported here, animals appeared to be grossly normal and did not exhibit any evidence of neurotoxicity such as ataxis, disorientation, tremor or convulsion. The results in FIG. 7 show that Compound 16 is tolerated at high doses on a q7d dosing schedule.

EXAMPLE

Figure 9:
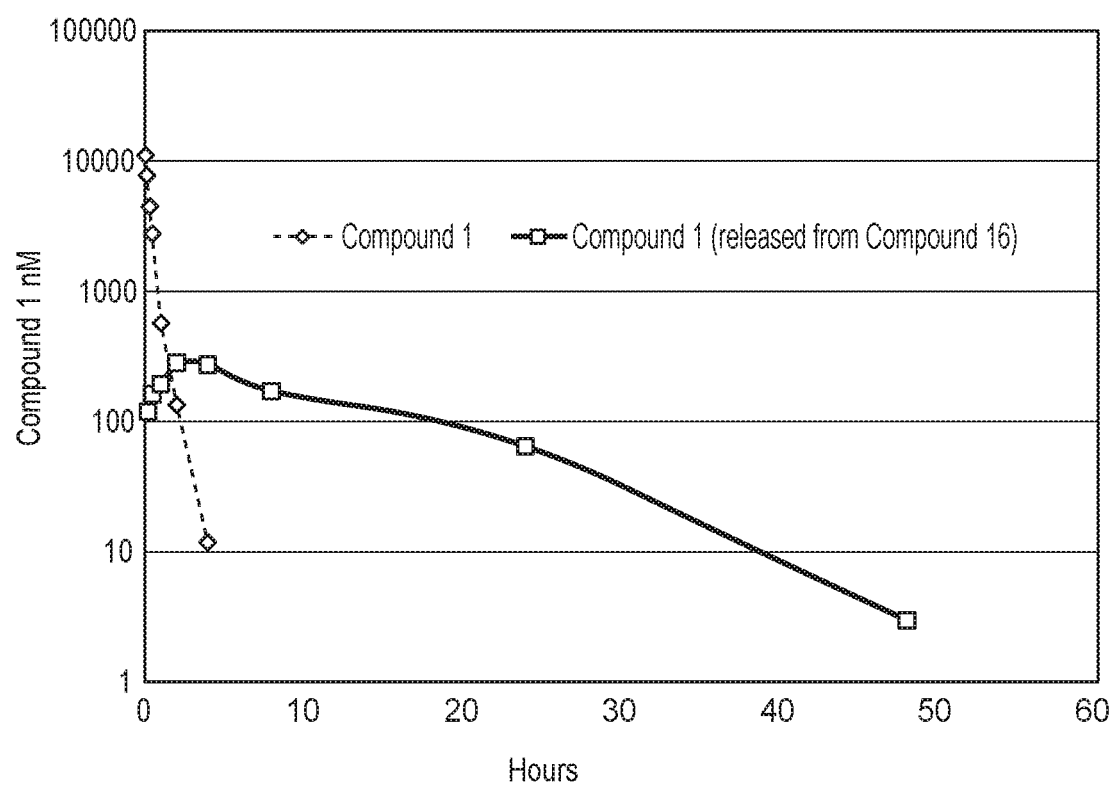
FIG. 9 is a graph showing the plasma concentration of a compound of the present invention over time based on administration of two different compounds.

Sprague Dawley male rats (N=3, average weight 350 g) were dosed by a single IV bolus with either vehicle, Compound 1 (30 mg/kg) or Compound 16 (200 mg/kg). Blood samples were collected via saphenous vein puncture at 0, 0.25, 0.5, 1, 2, 4, 8, 24 and 48 hours. An aliquot of each sample was diluted with methanol containing propranolol as an internal standard and analyzed by LC/MS/MS with a lower limit of quantitation of 2.5 nM. In the case of administering either Compound 1 or Compound 16, the analyte was Compound 1. The half-life of the small molecule Compound 1 is in the range of 10-15 minutes; Cmax is approximately 15 µM and occurs at $T_0$. For the polymer conjugate, Compound 16, the released small molecule exhibits a Cmax of approximately 0.3 µM at about 3 hours and a terminal elimination half-life of 10 hours. These results are displayed in FIG. 9.

Test articles were administered subcutaneously on an every 4 day (q4d) schedule in a diet-induced obesity (DIO) Levin-DS rat model. The efficacy of Compound 16 was also evaluated on a weekly (q7d) dosing schedule. A dietary intervention (Standard Chow, Labdiet 5001; 3.4 kcal/g) was included to compare to the drug interventions. Upon arrival at three weeks of age, the male rats received ad libitum pellets of Harlan Diet TD.06414, 60% of calories from fat, 21% of calories from carbohydrate; 5.1 kcal/g. Prior to dosing the rats were randomized into groups of three animals with an average body weight of 595 gm. The rats were treated with either phosphate buffered saline (vehicle), Compound 16 or Compound 1 or CKD-732 (dorsal, subcutaneous administration). Compound 16 was dissolved in vehicle. Compound 1 in the form of the hemitartrate and CKD-732 in the form of the hemitartrate were dissolved in ethanol prior to dilution with vehicle. All doses were administered at a volume of 5.0 ml/kg. Treatment was continued for 68 days at the doses and on the schedule shown in Table 10 below. Since the molecular weight of CKD-732 is 15% greater than the molecular weight of Compound 1, CKD-732 was dosed at 1.15 mg/kg while Compound 1 was dosed at 1 mg/kg for the purpose of comparison on a molar basis. On day 1, first dose, the rats were 14 weeks of age. Also on day 1, Group 2 was switched from the high fat diet to a standard chow diet; the remaining groups were maintained on a high fat diet for the duration of the study.

TABLE 10

| Group # | Test Article | # of rats | Route | Diet | Dose Frequency | Dose Volume (ml/kg) | Conc. (mg/ml) | Dose (mg/kg) |
|---|---|---|---|---|---|---|---|---|
| 1 | Vehicle | 3 | SC | 60% Fat | q4day | 5.0 | 0 | 0 |
| 2 | Vehicle | 3 | SC | Standard | q4day | 5.0 | 0 | 0 |
| 3 | Cmpd 16 | 3 | SC | 60% Fat | q4day | 5.0 | 0.067 | 0.3 |
| 4 | Cmpd 16 | 3 | SC | 60% Fat | q4day | 5.0 | 0.2 | 1.0 |
| 5 | Cmpd 16 | 3 | SC | 60% Fat | q4day | 5.0 | 0.6 | 3.0 |
| 6 | Cmpd 16 | 3 | SC | 60% Fat | q7day | 5.0 | 1.2 | 6.0 |
| 7 | Cmpd 1 | 3 | SC | 60% Fat | q4day | 5.0 | 0.2 | 1.0 |
| 8 | Cmpd 1 | 3 | SC | 60% Fat | q4day | 5.0 | 0.6 | 3.0 |
| 9 | CKD-732 | 3 | SC | 60% Fat | q4day | 5.0 | 0.23 | 1.15 |

Example In Vivo Testing DIO Levin Rats—Weight Changes, Food Consumption, Body Composition, Schedule-Dose Response, Leptin Levels A study was conducted to evaluate the relative efficacy of the fumagillol polymer conjugate, Compound 16, and the small molecule fumagillol derivatives, Compound 1, and CKD-732 (also known as beloranib and ZGN-433). CKD-732 as referred to herein is the hemitartrate salt of the following structure:

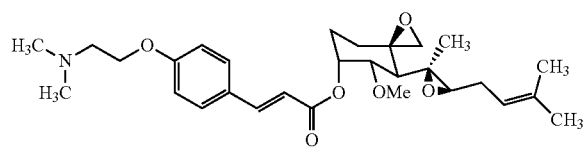

Compound 1 was also tested in the form of the hemitartrate salt.

Animals were weighed every other day. Food consumption was measured weekly. On an approximately weekly basis throughout the study, blood samples were taken for assessment of serum chemistries including glucose and insulin. On Day 48 all rats underwent a 4 hour fasted Oral Glucose Tolerance Test (OGTT). Animals were dosed orally (per os, PO) at 8 mL/kg 25% glucose (2 g/kg). On day 68, gross pathology was performed to determine body composition.

Figure 11:
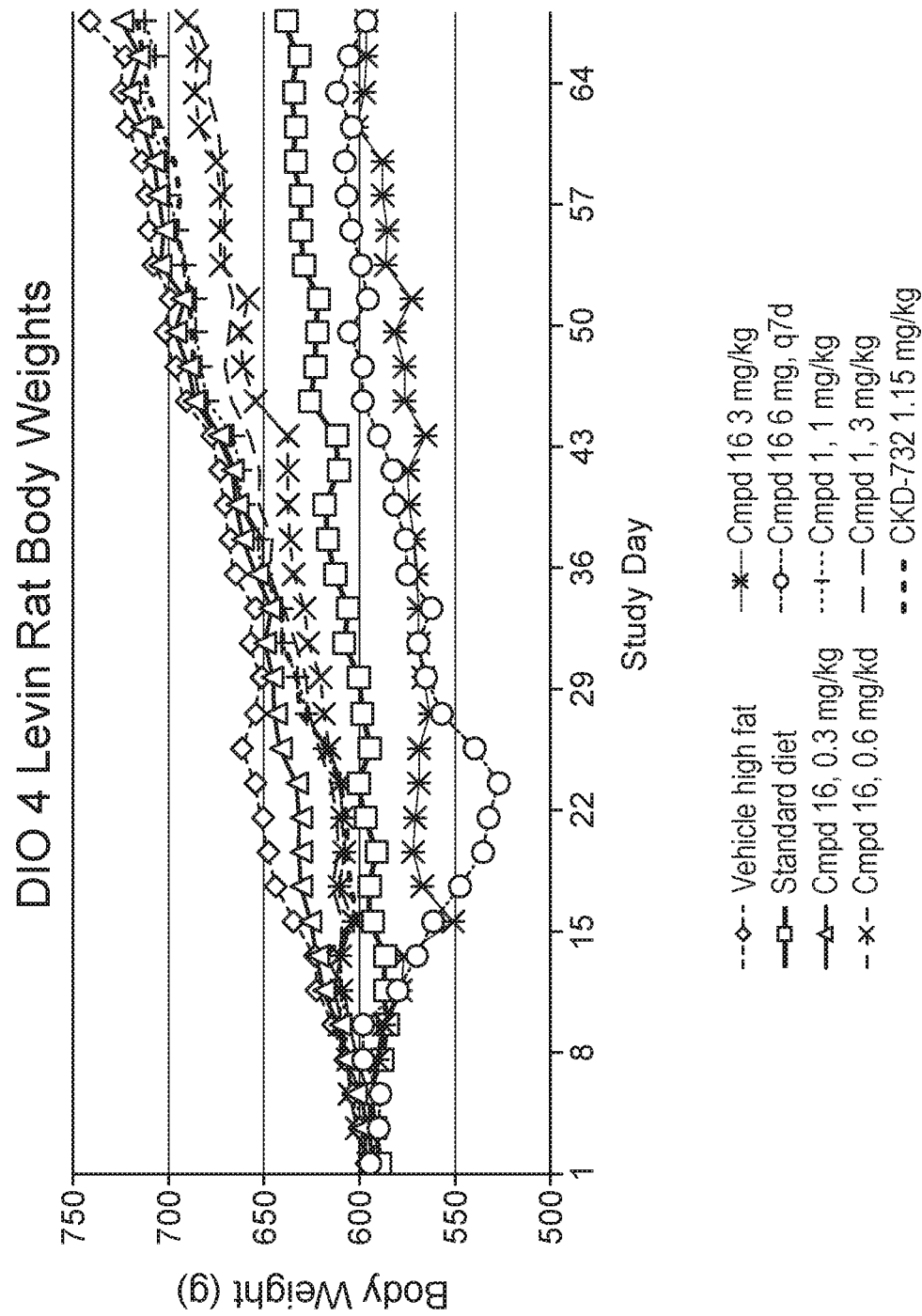
FIG. 11 is a graph showing body weight changes in male Levin rats on a high fat diet following administration of various compounds of the present invention.

FIG. 11 shows change in body weight versus study day for each group. Significant reduction in body weight was seen in both the Q4D and Q7D polymer conjugate dosed groups. Treatment with Compound 16 at 3 mg/kg (Q4D) or 6 mg/kg (Q7D) showed greater weight loss than the change to a standard chow. At the end of the study, Compound 16 at 3 mg/kg on a Q4D schedule showed a 22.1% lower body weight than the vehicle control, and a 6.2% lower body weight than rats on the standard chow diet. After about ten weeks, treatment with Compound 16 at 6 mg/kg on a Q7D schedule showed comparable body weight to treatment at 3 mg/kg dose on a Q4D schedule. Compound 1 dosed at 1 mg/kg and CDK-732 dosed at 1.15 mg/kg on a Q4D schedule showed 3.9% or 3.2% lower body weights than vehicle. Compound 1 dosed at 3 mg/kg on a Q4D schedule showed 8.9% lower body weight than vehicle. The polymer conjugates are approximately $\frac{1}{6}^{th}$ of the active fumagillol derivative by weight.

Figure 12:
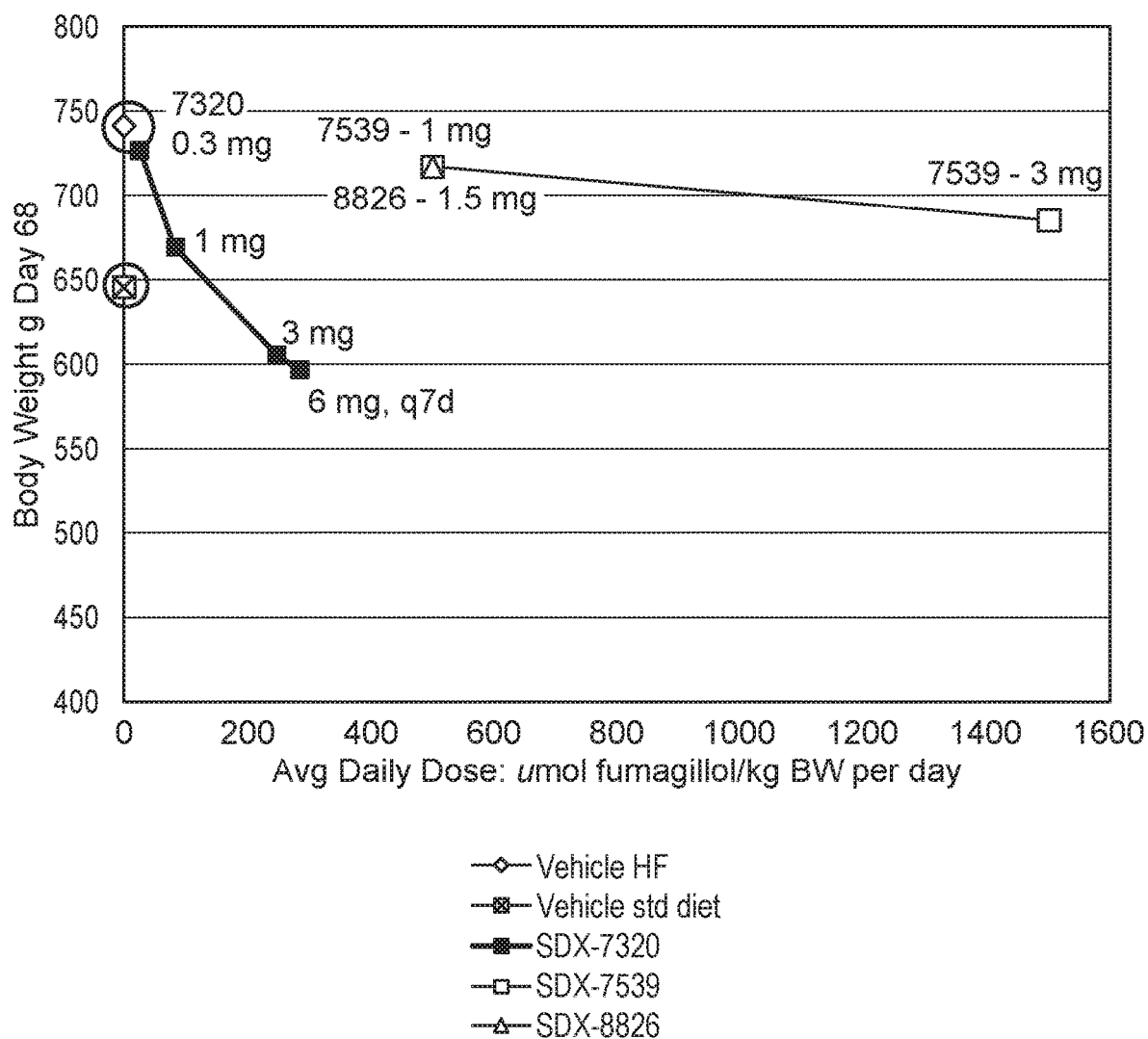
FIG. 12 is a graph showing fumagillol exposure versus weight loss in DIO rats following administration of various compounds of the present invention.

FIG. 12 shows day 68 final body weight for all groups as a function of the average daily fumagillol exposure. Both Vehicle and Standard Diet had no fumagillol exposure. Compound 16 shows greater weight loss with significantly lower fumagillol exposure as compared to Compound 1 or CKD-732 on the same schedule as the polymer conjugate. All groups were dosed on a Q4D schedule, except for Compound 16 at 6 mg/kg, which was dosed Q7D.

TABLE 11

Avg (n = 3) DIO Rat Final BW (g) as a function of fumagillol dose
Weight Loss vs. Exposure After 68 Days on Intervention

| Group | Dose (mg/kg) | Schedule | μM Fumagillol kg/day | Final BW (g) |
|---|---|---|---|---|
| Vehicle HF | 0 | q4d | 0 | 742.3 |
| Standard Diet | 0 | q4d | 0 | 645.0 |
| Cmpd 16 | 0.3 | q4d | 25 | 727.3 |
| Cmpd 16 | 1.0 | q4d | 83 | 668.6 |
| Cmpd 16 | 3.0 | q4d | 250 | 604.7 |
| Cmpd 16 | 6.0 | q7d | 286 | 596.7 |
| Cmpd 1 | 1.0 | q4d | 500 | 717.3 |
| Cmpd 1 | 3.0 | q4d | 1500 | 684.0 |
| CKD-732 | 1.15 | q4d | 500 | 714.0 |

Figure 13:
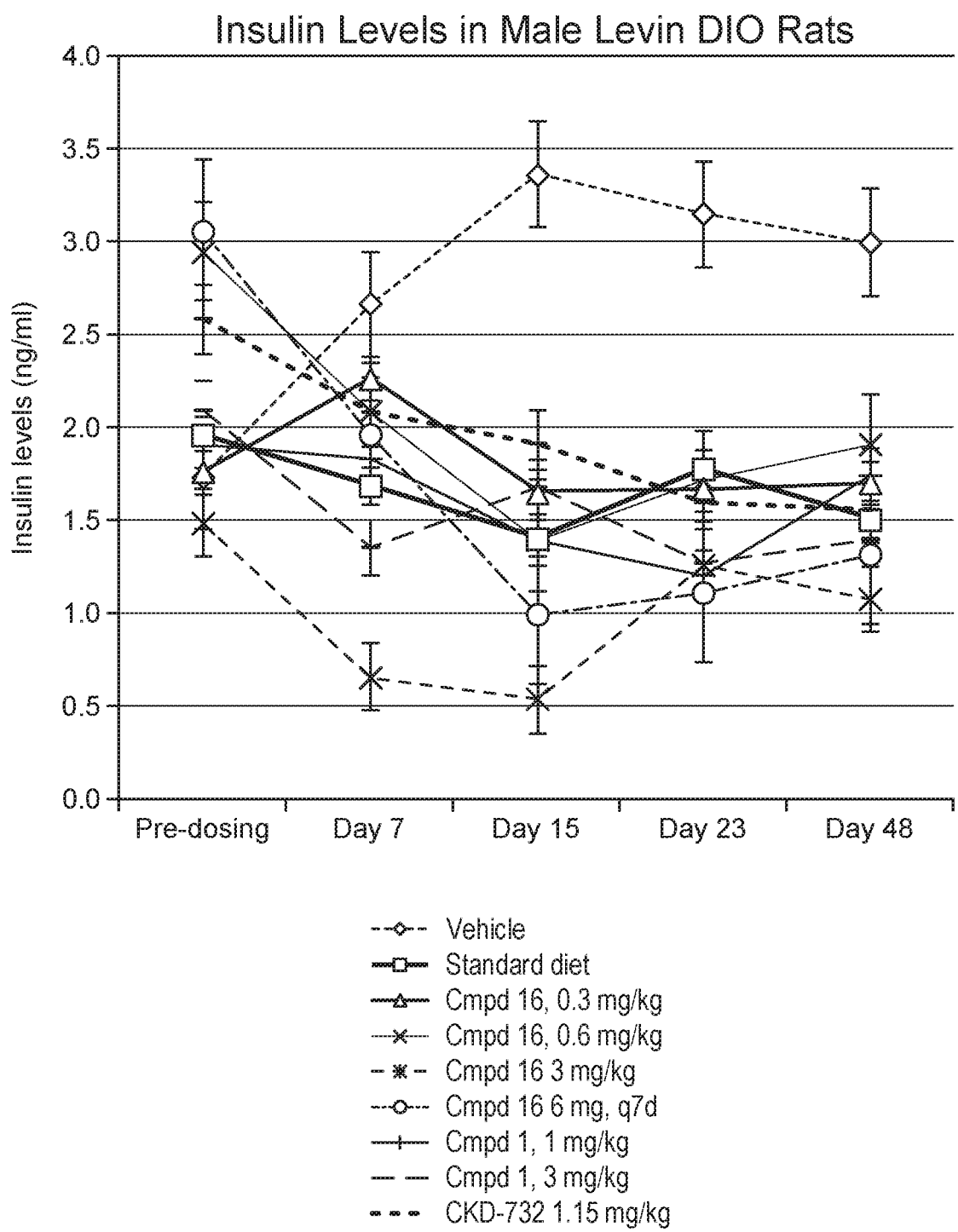
FIG. 13 is a graph showing changes in insulin levels in male Levin DIO rats on a high fat diet following administration of various compounds of the present invention.

FIG. 13 shows the reductions in serum insulin levels in male Levin DIO Rats maintained on a 60% fat diet and dosed with the compounds of the present invention on a q4d (3 mg/kg) and q7d (6 mg/kg) schedule compared to a standard diet intervention and the vehicle group.

TABLE 12

Avg (n = 3) DIO Rat Insulin as a function of time
Avg. Insulin (ng/mL) in Male Levin DIO Rats

| | Pre-dosing | Day 7 | Day 15 | Day 23 | Day 48 |
|---|---|---|---|---|---|
| Vehicle | 1.74 | 2.66 | 3.37 | 3.15 | 3.00 |
| Standad diet | 1.96 | 1.68 | 1.40 | 1.78 | 1.51 |
| Cmpd 16, 0.3 mg/kg | 1.76 | 2.27 | 1.65 | 1.66 | 1.70 |
| Cmpd 16, 0.6 mg/kd | 2.95 | 2.09 | 1.38 | 1.72 | 1.91 |
| Cmpd 16 3 mg/kg | 1.49 | 0.66 | 0.54 | 1.26 | 1.08 |
| Cmpd 16 6 mg, q7d | 3.06 | 1.96 | 1.00 | 1.11 | 1.32 |
| Cmpd 1, 1 mg/kg | 1.92 | 1.83 | 1.39 | 1.20 | 1.75 |
| Cmpd 1, 3 mg/kg | 2.10 | 1.35 | 1.68 | 1.27 | 1.40 |
| CKD-732, 1.15 mg/kg | 2.58 | 2.08 | 1.91 | 1.60 | 1.56 |

Table 12 shows the changes in fasting insulin levels for each group. All groups (except for the Vehicle control group) showed reduced insulin levels, demonstrating that the Compounds of the present invention lower insulin levels on an infrequent dosing schedule.

Figure 14:
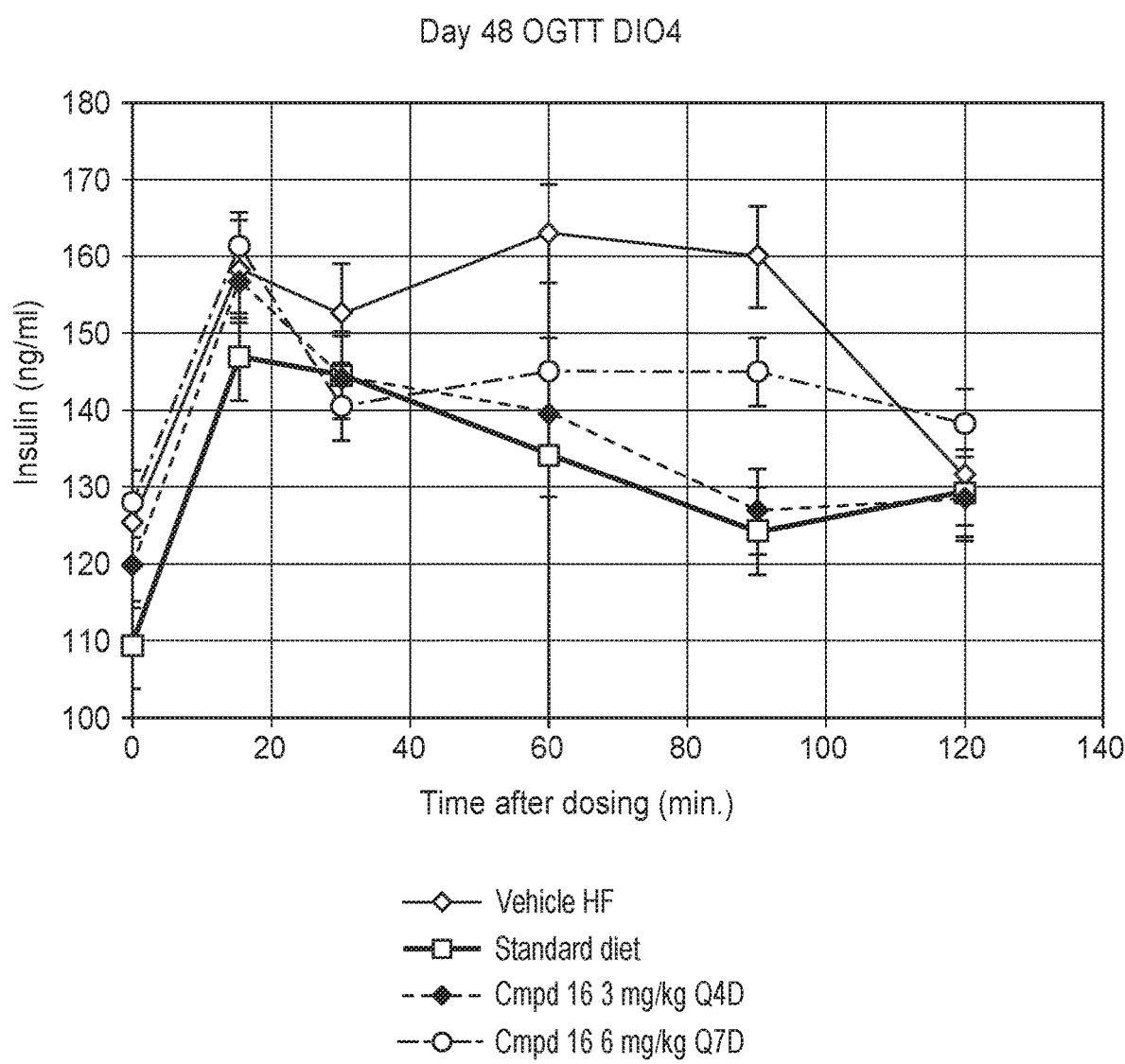
FIG. 14 is a graph showing insulin levels during an oral glucose challenge (OGTT) following administration of various compounds of the present invention.

FIG. 14 shows the results of an oral glucose tolerance test (OGTT) on insulin levels in rats treated with the compounds of the present invention on a q4d and q7d schedule compared to the standard diet intervention and the vehicle groups. The standard diet intervention also resulted in lower insulin levels. Insulin levels remained reduced versus vehicle, in the presence of abnormally high glucose levels indicating that lower levels of insulin were needed to reduce blood glucose (see FIG. 15) suggesting improved/restored insulin sensitivity.

Figure 15:
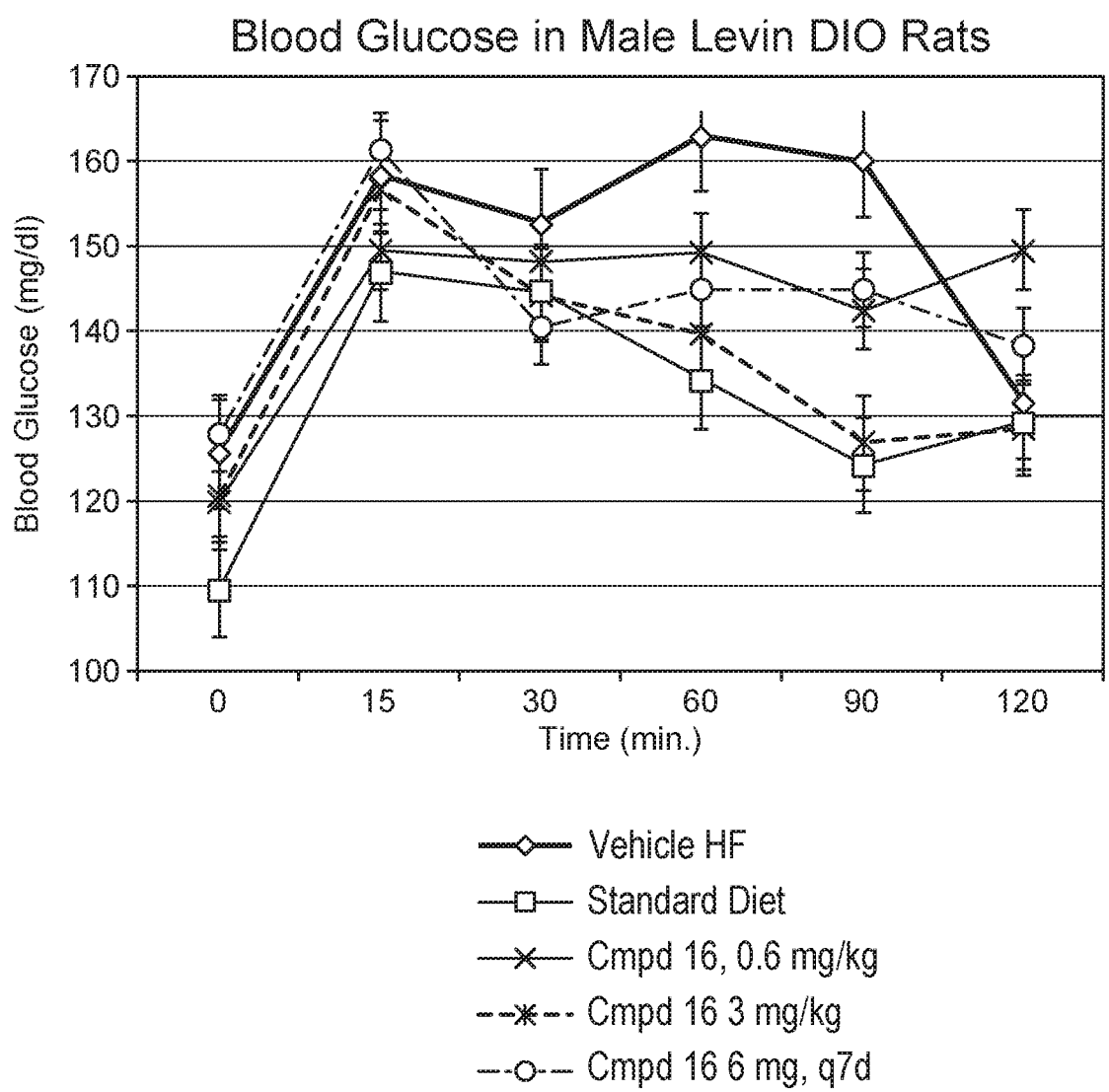
FIG. 15 is a graph showing reductions in blood glucose in DIO rats during an oral glucose challenge (OGTT) following administration of various compounds of the present invention.

FIG. 15 shows reduced glucose levels versus time for various treatments following an oral glucose challenge.

TABLE 13

Blood Glucose Levels, following an oral glucose
tolerance test (OGTT) in DIO Rats on a 60% high fat diet.
Blood Glucose (mg/dl) in Male Levin Rats During a Glucose Challenge

| | Time | | | | | |
|---|---|---|---|---|---|---|
| Group | pre-OGTT | 15 | 30 | 60 | 90 | 120 | BW (g) |
| Vehicle HF | 126 | 158 | 153 | 163 | 160 | 132 | 702 |
| Standard Diet | 110 | 147 | 145 | 134 | 124 | 129 | 617 |
| Cmpd 16, 0.3 mg/kg | 121 | 156 | 145 | 157 | 149 | 147 | 697 |
| Cmpd 16, 0.6 mg/kd | 121 | 150 | 148 | 149 | 143 | 150 | 662 |
| Cmpd 16 3 mg/kg | 120 | 157 | 144 | 140 | 127 | 129 | 582 |
| Cmpd 16 6 mg, q7d | 128 | 161 | 141 | 145 | 145 | 138 | 604 |
| Cmpd 1, 1 mg/kg | 124 | 156 | 142 | 152 | 151 | 142 | 686 |
| Cmpd 1, 3 mg/kg | 123 | 175 | 171 | 149 | 147 | 129 | 668 |
| CKD-732, 1.15 mg/kg | 123 | 174 | 171 | 158 | 153 | 144 | 686 |

Figure 16:
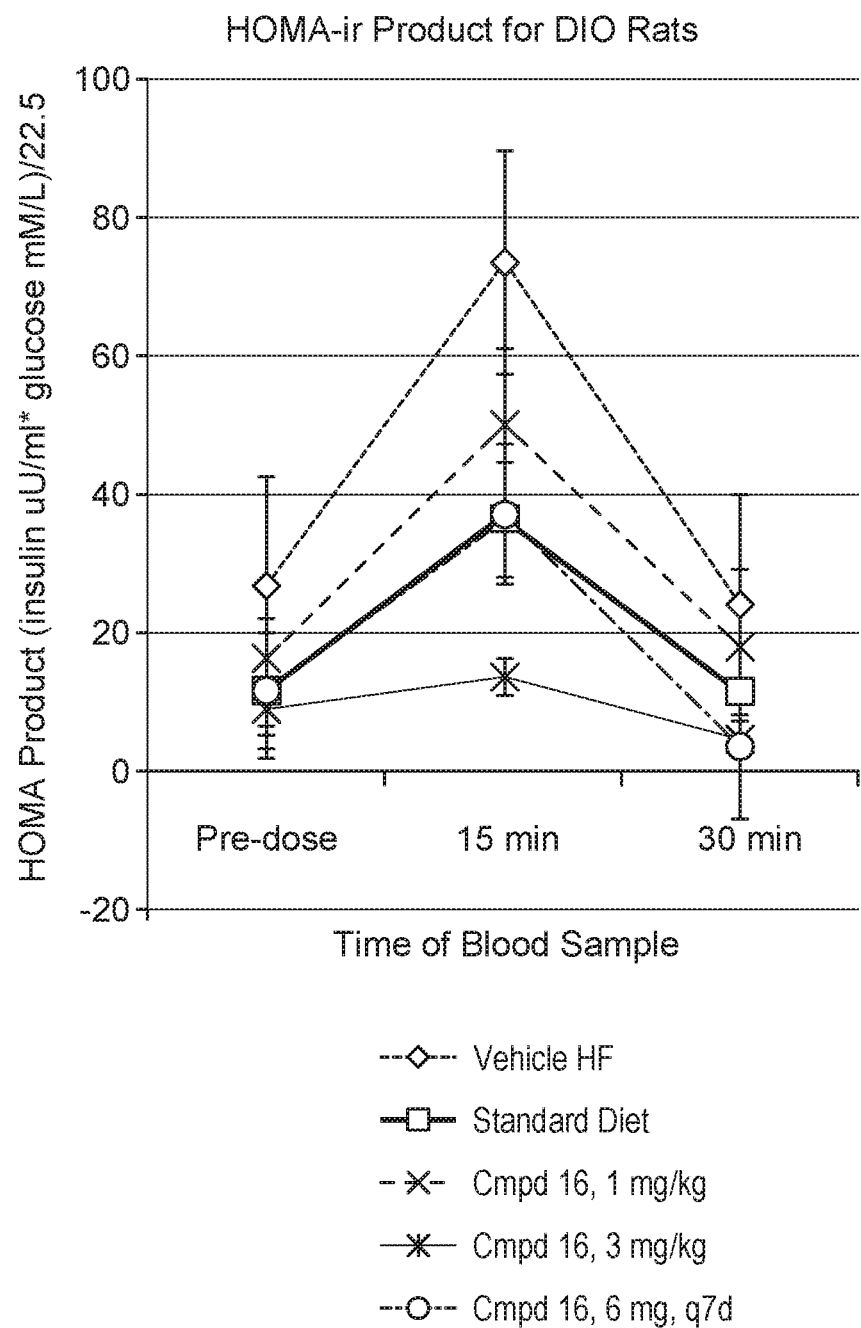
FIG. 16 is a graph showing HOMA-ir product during an OGTT in DIO rats following administration of various compounds of the present invention.

FIG. 16 shows the product of glucose (mM/L) x insulin (uU/ml)/22.5 in male Levin DIO rats as an accepted measure of insulin sensitivity (Matthews et al., Diabetologia (1985) 28, 412±419; Pickavance et al., British Journal of Pharmacology (1999) 128, 1570±1576).

TABLE 14

HOMA-ir Calculation for DIO Rats
HOMA-ir (Insulin Sensitivity)

| | Pre-dose | 15 min | 30 min |
|---|---|---|---|
| Vehicle HF | 26.7 | 73.6 | 24.3 |
| Standard Diet | 11.7 | 36.5 | 11.7 |
| Cmpd 16 0.3 mg/kg | 14.6 | 40.1 | 10.8 |
| Cmpd 16, 1 mg/kg | 16.4 | 50.1 | 18.1 |
| Cmpd 16, 3 mg/kg | 9.2 | 13.7 | 4.6 |
| Cmpd 16, 6 mg, q7d | 12.0 | 37.2 | 3.5 |
| Cmpd 1, 1 mg/kg | 15.4 | 42.7 | 21.1 |
| Cmpd 1, 3 mg/kg | 12.2 | 29.2 | 9.5 |
| CKD-732, 1.15 mg/kg | 13.6 | 49.0 | 35.9 |

Figure 17:
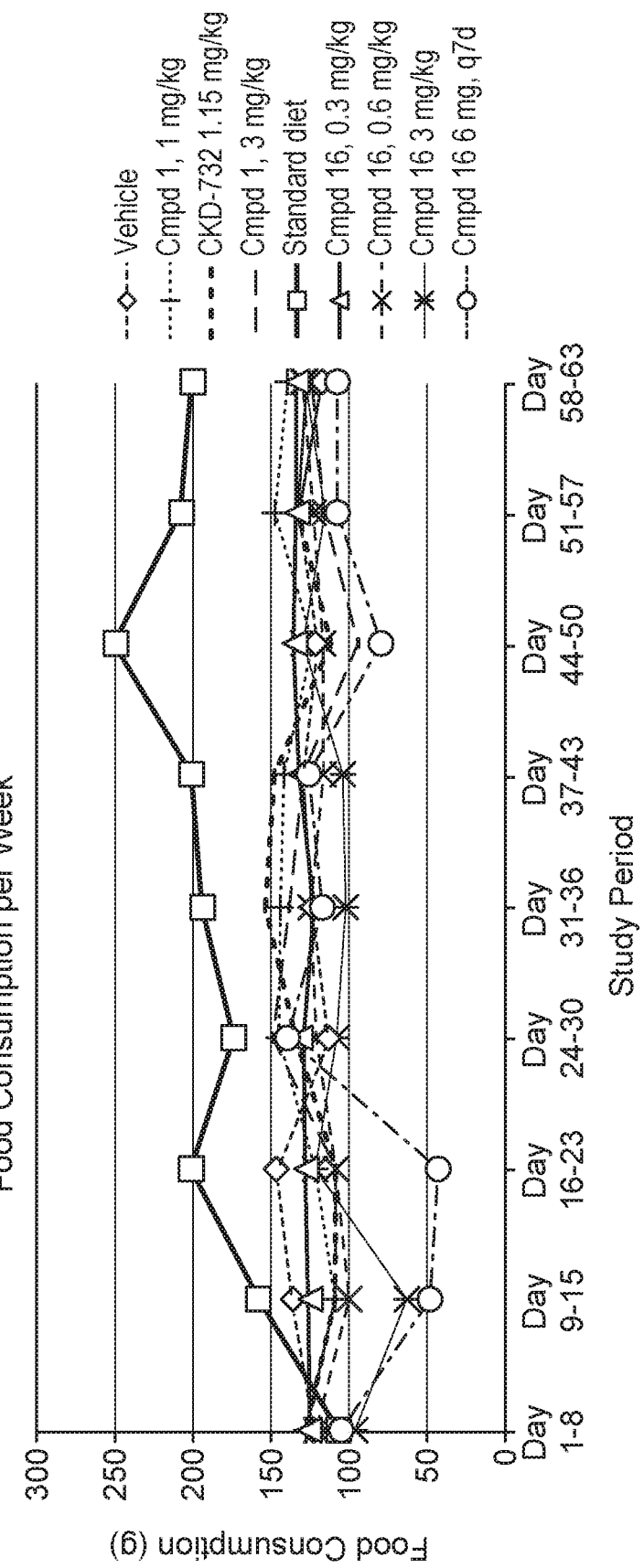
FIG. 17 is a graph showing weekly food consumption following administration of various compounds of the present invention.

The adipocyte hormone leptin is a known suppressor of appetite. Leptin resistance (abnormally high levels independent of food intake) is known to occur for patients and animals with dietary obesity (Levin et al., Am J Physiol Regul Integr Comp Physiol. 2002 October; 283(4):R941-8). Low levels of leptin have been associated with dietary hyperphagia (Sindelar et al., 1999, Enriori et al., 2006). Food consumption was measured on a weekly basis. Serum leptin levels were measured on day 29 and plotted against food consumption for the week containing day 29. Animals on a standard chow diet were hyperphagic, and showed significantly greater food intake versus leptin levels than did the compounds of the present invention. Treatment with Compound 1 did not result in significant reductions in leptin levels. FIG. 17 shows the weekly food consumption in grams for each group. The Standard chow group showed a significant increase in food intake following the switch from a high fat diet to a standard diet. Hyperphagia is known to occur in order to maintain caloric intake.

TABLE 15

Food Consumption
Group Average Food Consumption

| Dose | Day 1-8 Food (g) | Day 9-15 Food (g) | Day 16-23 Food (g) | Day 24-30 Food (g) | Day 31-36 Food (g) | Day 37-43 Food (g) | Day 44-50 Food (g) | Day 51-57 Food (g) | Day 58-63 Food (g) | Day 63-68 Food (g) |
|---|---|---|---|---|---|---|---|---|---|---|
| Vehicle | 119.7 | 136.8 | 146.9 | 113.8 | 124.0 | 129.4 | 120.9 | 131.8 | 117.9 | 99.0 |
| Standad diet | 108.1 | 158.6 | 201.7 | 174.6 | 194.8 | 201.8 | 250.4 | 208.3 | 201.1 | 120.6 |
| Cmpd 16, 0.3 mg/kg | 126.2 | 125.9 | 128.2 | 129.3 | 122.4 | 131.9 | 135.6 | 134.5 | 134.2 | 57.6 |
| Cmpd 16, 0.6 mg/kd | 121.2 | 101.0 | 109.7 | 122.1 | 125.8 | 116.6 | 118.2 | 123.1 | 130.7 | 45.9 |
| Cmpd 16 3 mg/kg | 97.3 | 63.2 | 123.4 | 108.7 | 102.6 | 105.5 | 129.9 | 115.2 | 128.0 | 43.3 |
| Cmpd 16 6 mg, q7d | 105.2 | 48.3 | 43.9 | 139.8 | 117.4 | 126.3 | 81.2 | 107.5 | 107.7 | 19.8 |
| Cmpd 1, 1 mg/kg | 128.6 | 109.3 | 121.1 | 145.9 | 144.6 | 141.7 | 122.4 | 147.7 | 140.7 | 55.1 |
| Cmpd 1, 3 mg/kg | 123.6 | 98.9 | 110.1 | 149.3 | 138.8 | 130.9 | 94.7 | 116.2 | 124.9 | 49.8 |
| CKD-732 1.15 mg/kg | 131.8 | 110.5 | 108.7 | 133.9 | 153.9 | 148.7 | 112.3 | 135.0 | 125.5 | 61.9 |

Figure 18:
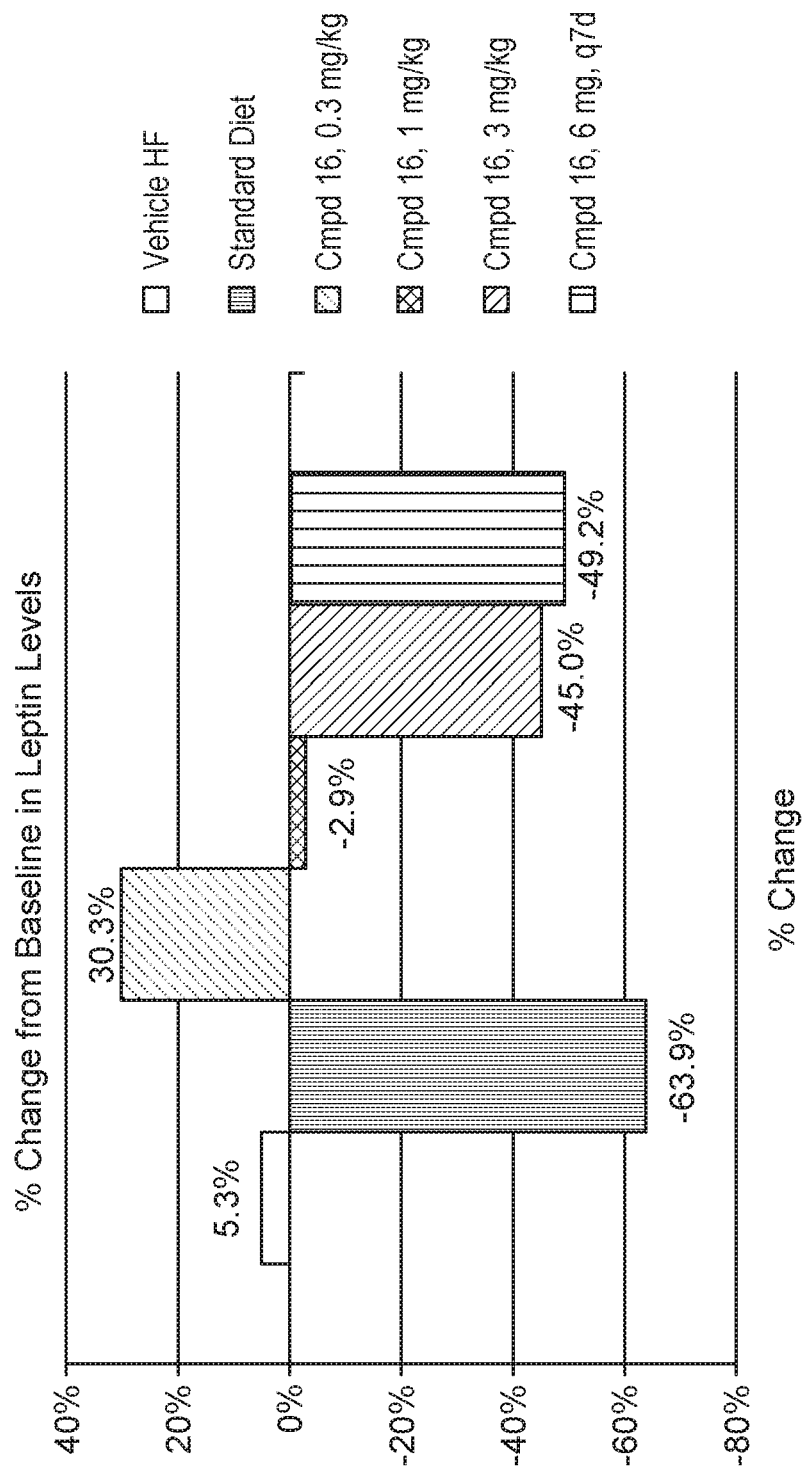
FIG. 18 is a graph showing changes in leptin levels from baseline following administration of various compounds of the present invention.

FIG. 18 shows changes from baseline in leptin levels in male Levin DIO rats kept on a high fat diet and treated with conjugates of the present invention or a standard chow intervention. A dose-dependent response was observed in the change in leptin levels from baseline for Compound 16.

TABLE 16

Changes in Leptin Levels from Baseline
Leptin Levels, Day 29, Changes from Baseline

| Group | % Change | Pre-dose | Day 29 |
|---|---|---|---|
| Vehicle HF | 5.3% | 4.43 | 4.67 |
| Standard Diet | -63.9% | 3.33 | 1.20 |
| Cmpd 16 0.3 mg/kg | 30.3% | 2.53 | 3.30 |
| Cmpd 16, 1 mg/kg | -2.9% | 4.67 | 4.53 |
| Cmpd 16, 3 mg/kg | -45.0% | 2.47 | 1.36 |
| Cmpd 16, 6 mg, q7d | -49.2% | 3.93 | 2.00 |
| Cmpd 1, 1 mg/kg | -1.3% | 2.50 | 2.47 |
| Cmpd 1, 3 mg/kg | 11.3% | 3.23 | 3.60 |
| CKD-732, 1.15 mg/kg | -3.0% | 4.43 | 4.30 |

Example: In Vivo Testing DIO Mice—Weight Changes, Food Consumption, Schedule-Dose Response Male C57Bl/6 mice (N=9/group) 21 weeks old with an average weight of 46.8 g were ad libitum fed a high fat diet composed of 60% Kcal from fat. Animals were dosed according to the schedule in Table 17 below.

TABLE 17

| Group | Treatment | Dose mg/kg | Vehicle | Frequency |
|---|---|---|---|---|
| 1 | Vehicle-1 | 0 | PBS | q4d |
| 2 | Polymer | 12 | PBS | q4d |
| 3 | Compound 16 | 2 | PBS | q4d |
| 4 | Compound 16 | 6 | PBS | q4d |
| 5 | Compound 16 | 12 | PBS | q8d* |
| 6 | CKD-732 | 1 | Vehicle-2 | qod |
| 7 | Vehicle-2 | 0 | Vehicle-2 | qod |
| 8 | CKD-732 | 2 | Vehicle-2 | q4d |
| 9 | Vehicle-2 | 0 | Vehicle-2 | q4d |

*vehicle-1 on alternate q4d

Compound dosing occurred between 9 and 10 am on the day of dosing. Groups 6 and 7 received a total of 17 doses. The q4d groups (1, 2, 3, 4, 8, 9) received a total of 9 doses. The q8d group (5) received a total of 5 drug doses. Body weight and food intake were measured every other day. Blood glucose was measured on Day -7, Day 0, Day 7, Day 14, Day 21 and Day 28 at 9:00 am in fed state (BG measured before dose on dosing days). BG was measured by glucometer. An intraperitoneal glucose tolerance test (ipGTT, 6 h fasting) was performed.

The study was terminated on day 34. Liver and epididymal white adipose tissues (eWAT) were harvested, weighed and stored at -80° C. Sera was collected to determine: AST, ALT, ALP, CK, BUN, creatinine, calcium, potassium, sodium, chloride, total protein, albumin, total bilirubin, glucose, triglyceride and cholesterol. Insulin samples were measured using a commercial kit.

Polymer as referred to in this example refers to poly [HPMA-co-MA-GFLG-N-(6-aminohexyl)acetamide, a polymer which does not contain fumagillol. The synthesis of poly[HPMA-co-MA-GFLG-N-(6-aminohexyl)acetamide is described in WO/2011/150022, which is included by reference in its entirety.

Structure of poly[HPMA-co-MA-GFLG-N-(6-aminohexyl)acetamide]

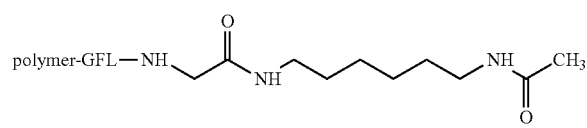

Figure 19:
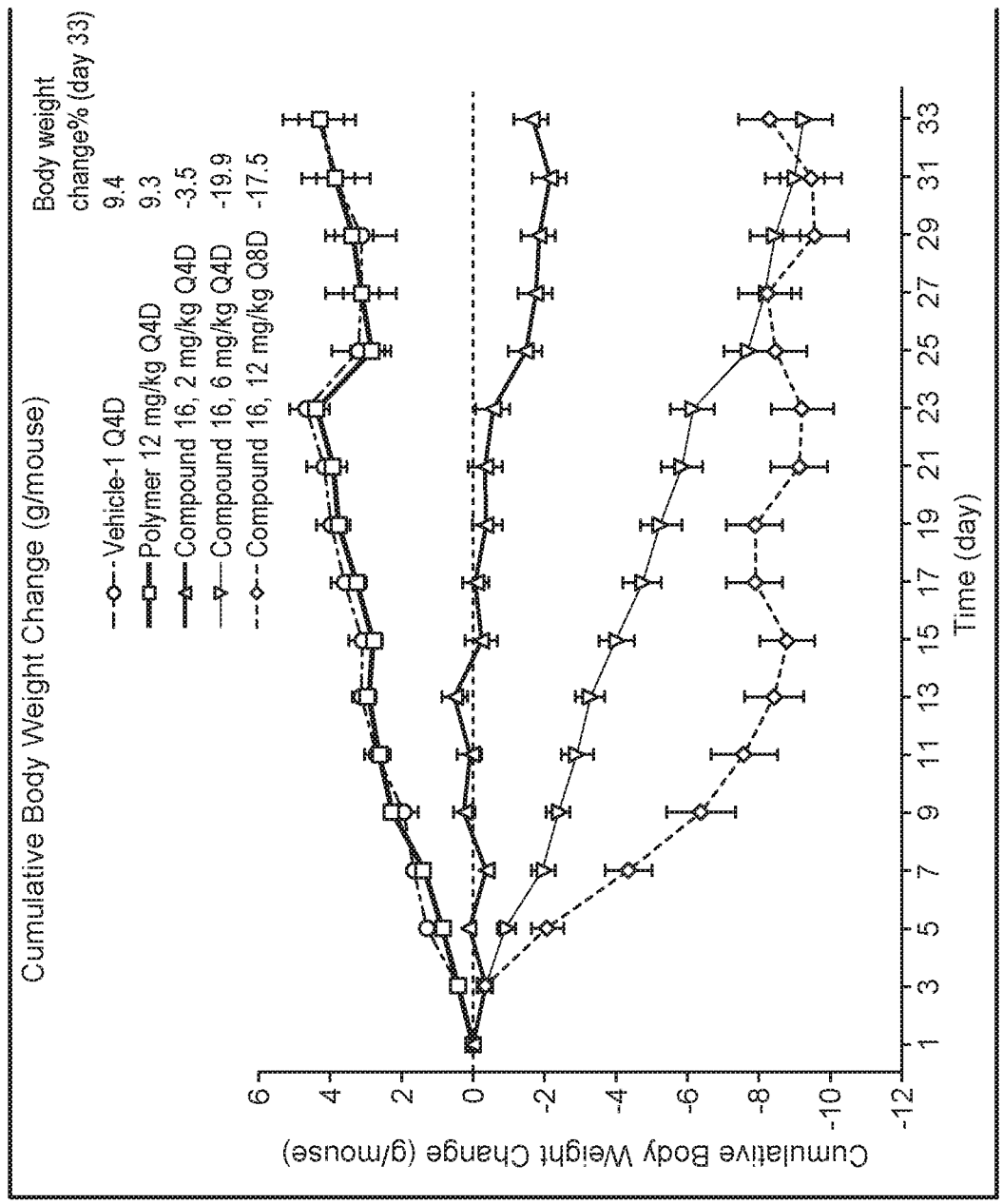
FIG. 19 is a graph showing body weight changes in DIO mice following administration of various compounds of the present invention on Q4D and Q8D schedules.

FIG. 19 shows the surprising and unexpected finding that 12 mg/kg dose on a Q8D schedule resulted in greater initial weight loss than the 6 mg/kg dose on a Q4D schedule. By study termination, the Q8D group had ceased to lose weight while the 6 mg/kg group appeared to continue to lose weight. The polymer which contains no fumagillol shows weight changes similar to vehicle.

Figure 20:
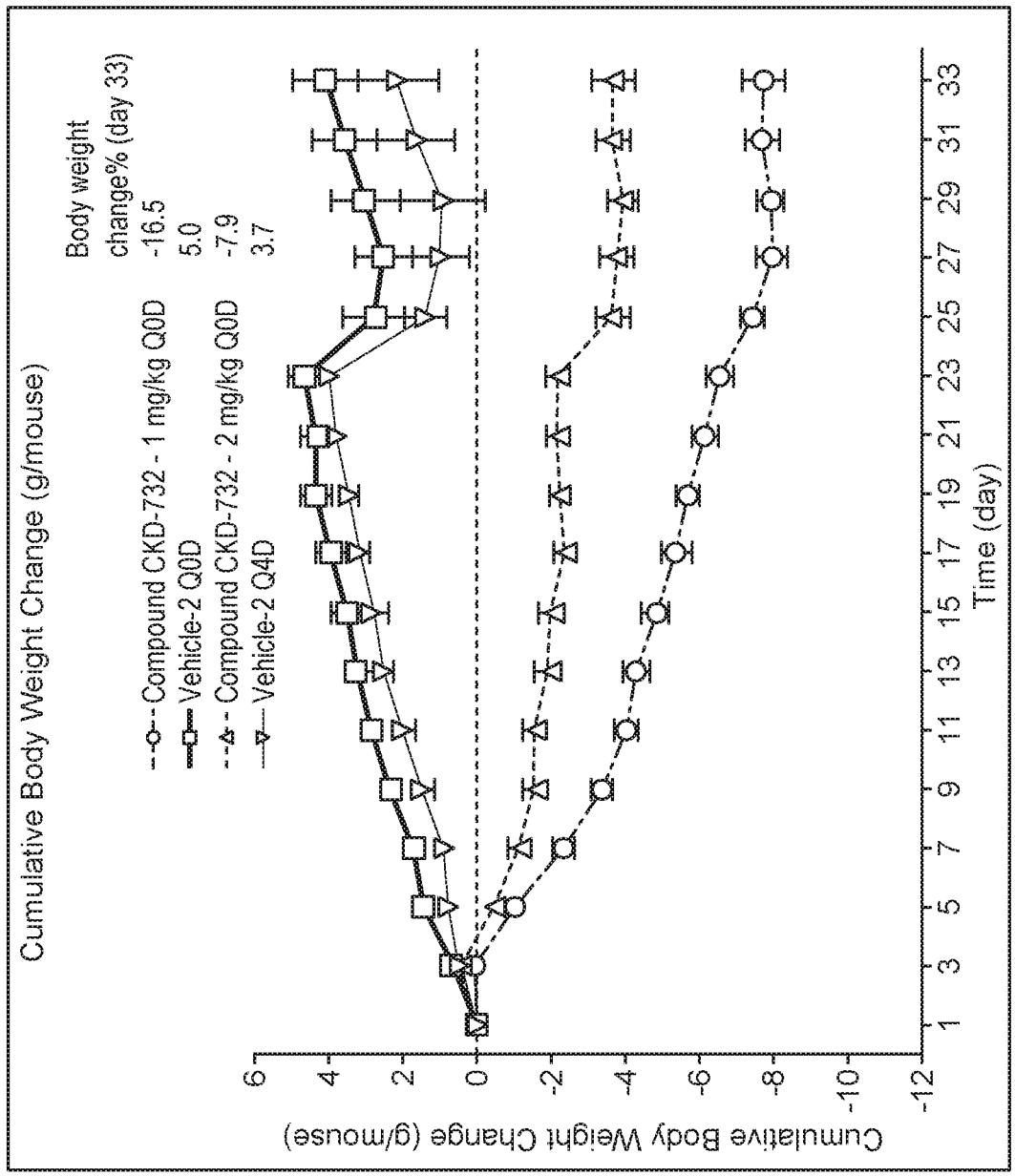
FIG. 20 is a graph showing weight loss following administration of CKD-732 on a Q2D and Q4D Schedule.

FIG. 20 shows that the small molecule CKD-732 (Compound B) dosed on a Q2D (QOD) schedule showed better response than the same average daily dose administered on a Q4D schedule. As expected, the small molecules show better responses with more frequent dosing.

Figure 21:
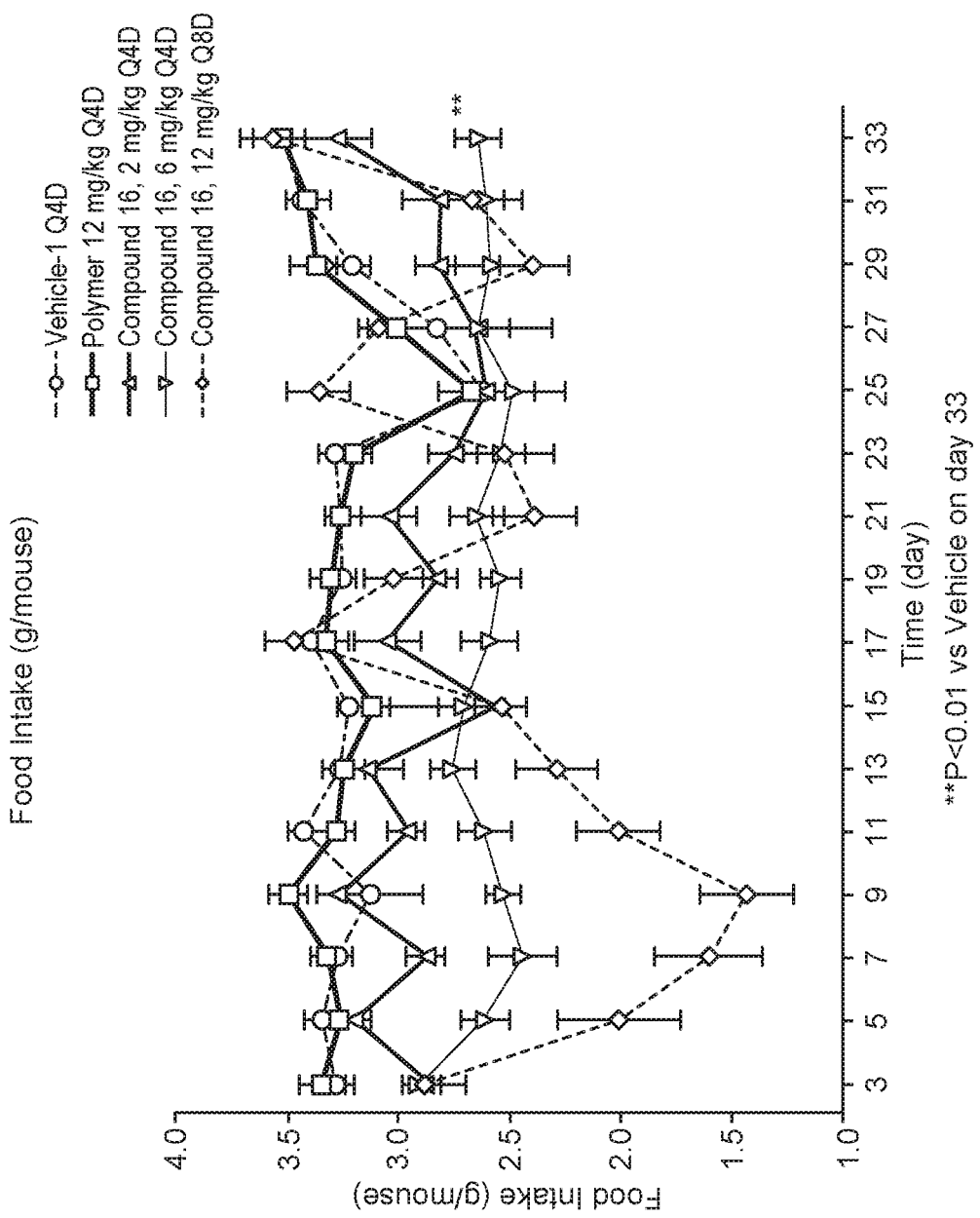
FIG. 21 is a graph showing the reductions in food intake following administration of various compounds of the present invention.

FIG. 21 shows reduction in food intake for the compounds of the present invention. Note the initial, significant reduction in food intake for the 12 mg/kg group on the Q8D schedule, and the subsequent recovery followed by a cyclical reduction-recovery pattern.

Figure 22:
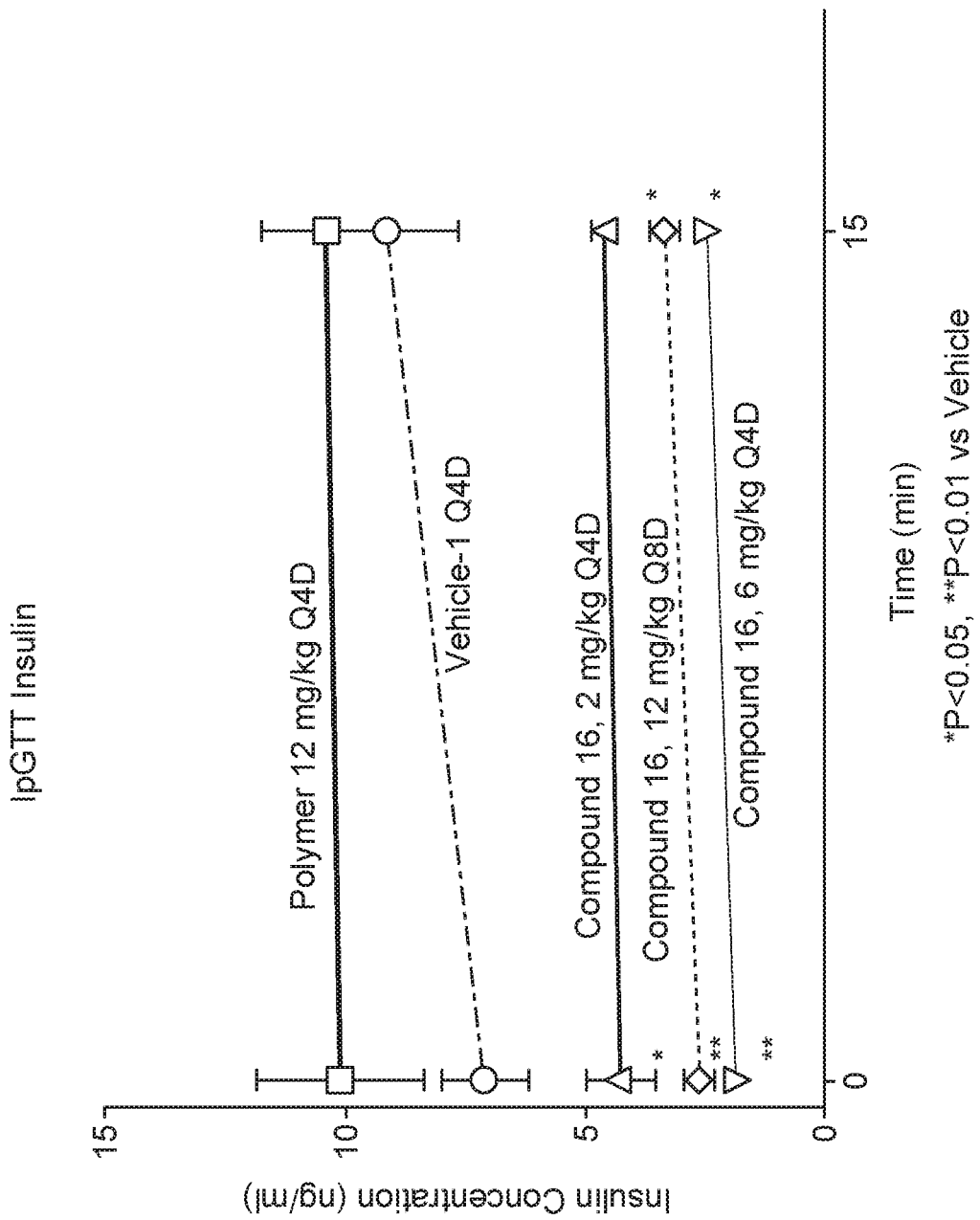
FIG. 22 is a graph showing significantly reduced insulin levels during an ipGTT in male C57Bl6 mice kept on a high fat diet for 25 weeks following administration of various compounds of the present invention.

FIG. 22 shows significantly reduced insulin levels during an ipGTT in male C57Bl6 mice kept on a high fat diet. The compounds of the present invention greatly reduce the amount of insulin excreted by the β cells in the presence of elevated glucose indicating reduced resistance and improved insulin sensitivity. Also note that fasting insulin was also reduced in the mice for all Compound 16 groups.

Figure 23:
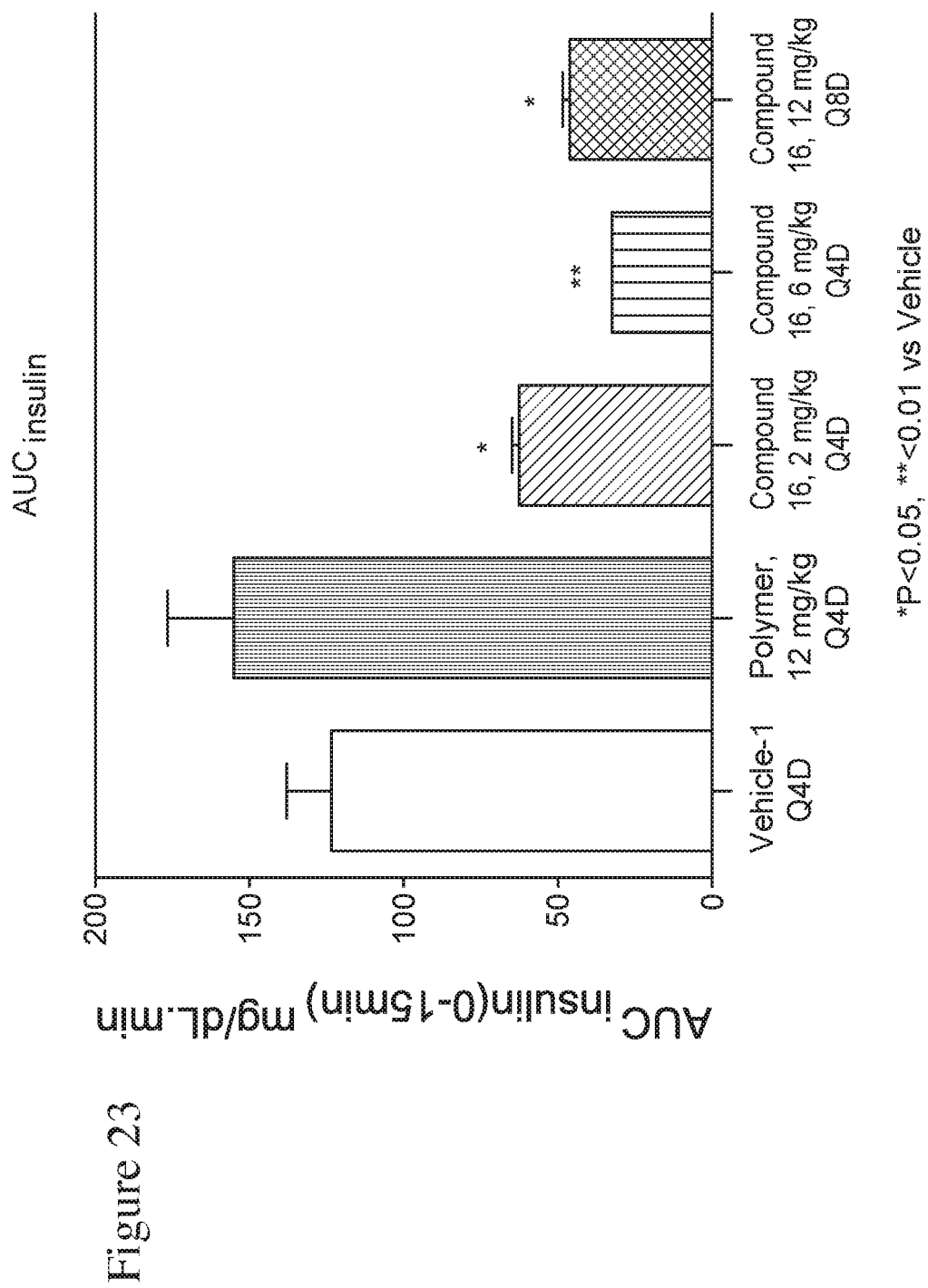
FIG. 23 is a graph showing insulin AUC during a glucose challenge in male DIO mice following administration of various compounds of the present invention.

FIG. 23 shows changes in the total insulin AUC in male C57Bl6 mice maintained on a high fat diet during a glucose challenge as a function of treatment group.

Figure 24:
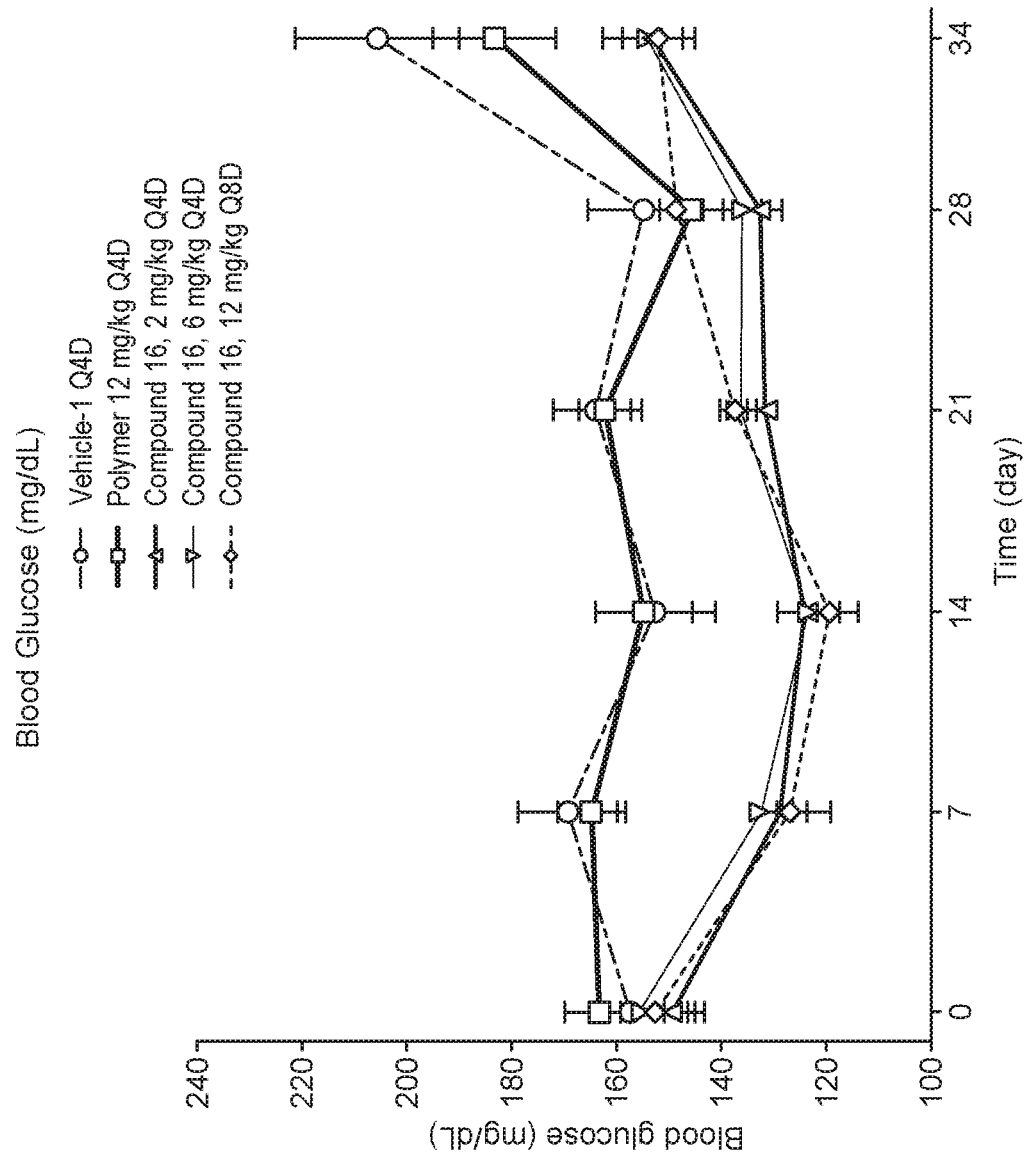
FIG. 24 is a graph showing blood glucose levels in male C57Bl6 mice on a high fat diet following administration of various compounds of the present invention.

FIG. 24 shows a lowering of blood glucose versus Vehicle and Polymer groups throught the treatment period.

Figure 25:
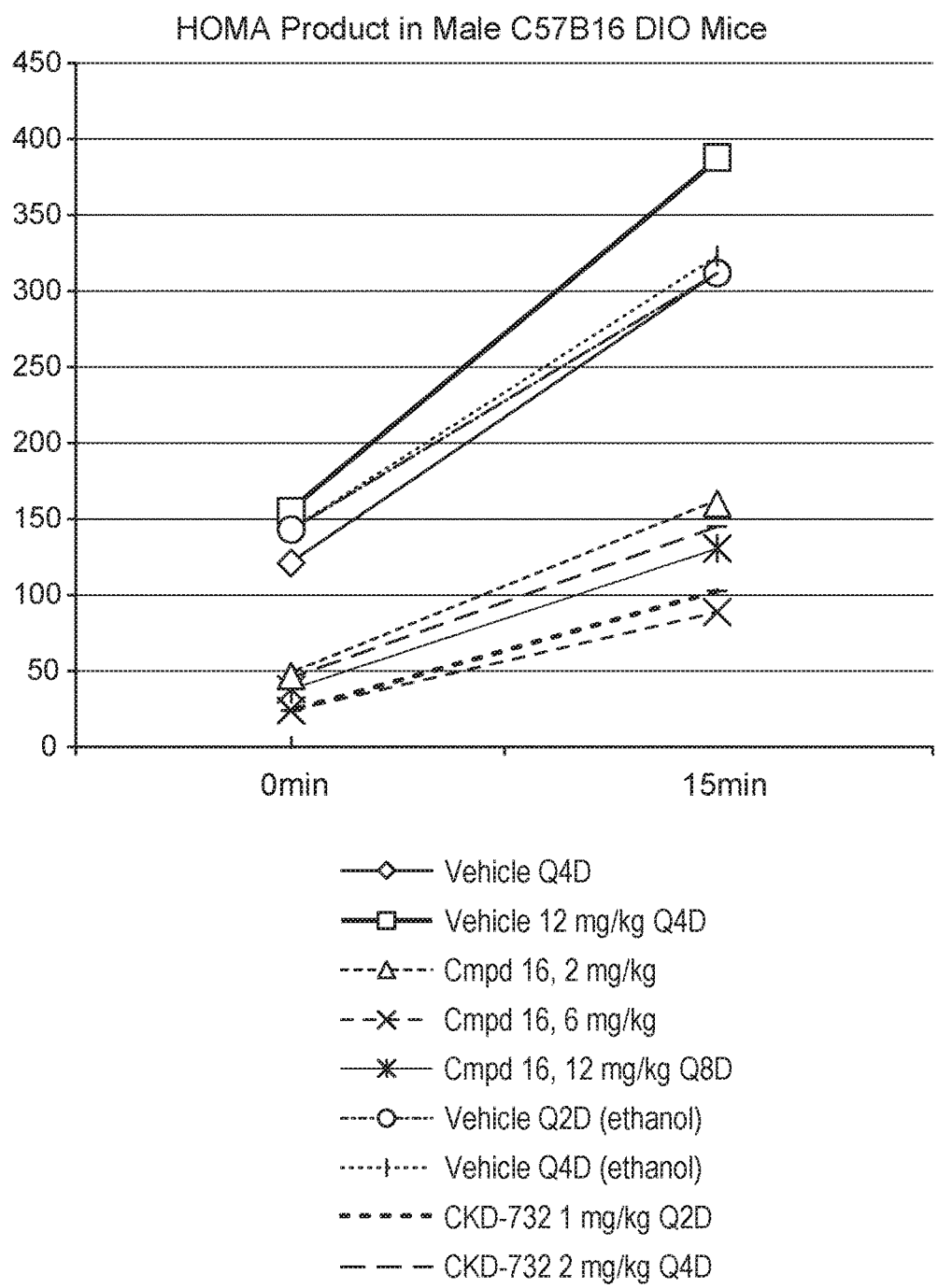
FIG. 25 is a graph showing HOMA product during an ipGTT in C57Bl6 Mice on a high fat diet following administration of various compounds of the present invention.

FIG. 25 shows the product of glucose (mg/dl) x insulin (µU/ml)/405 (Akagiri et al., A Mouse Model of Metabolic Syndrome, J. Clin. Biochem. Nutr., 42, 150-157, March 2008) or the HOMA-ir measurement, which is an accepted measurement of insulin resistance and a predictor of cardiovascular disease (Bonora et al., Diabetes Care. 2002, 25, 1135-1141).

TABLE 18

Data Used for the HOMA-ir Calculation

|  | Insulin (µU/ml) | | Glucose (mg/dl) | |
| --- | --- | --- | --- | --- |
| ipGTT | 0 min | 15 min | 0 min | 15 min |
| Vehicle Q4D | 205.0 | 263.4 | 239.2 | 482.0 |
| Vehicle 12 mg/kg Q4D | 291.9 | 299.4 | 215.6 | 525.9 |
| Cmpd 16, 2 mg/kg | 104.6 | 133.4 | 182.8 | 488.6 |
| Cmpd 16, 6 mg/kg | 53.2 | 64.3 | 179.8 | 557.3 |
| Cmpd 16, 12 mg/kg Q8D | 75.9 | 96.0 | 204.0 | 553.1 |
| Vehicle Q2D (ethanol) | 264.7 | 241.8 | 218.0 | 521.9 |
| Vehicle Q4D (ethanol) | 249.4 | 264.9 | 231.0 | 493.6 |
| CKD-732 1 mg/kg Q2D | 54.8 | 89.3 | 161.3 | 469.2 |
| CKD-732 2 mg/kg Q4D | 99.8 | 118.3 | 182.6 | 498.6 |

Example Efficacy of Various Compounds in DIO Mouse Model

C57Bl6 male mice (N=6) were ad libitum fed TD.06414 a high fat diet composed of 60% Kcal from fat (Harlan diet). On study day 1 animals were randomized into groups so that the average weight of the mice in each group was 47 g. The mice were treated with either phosphate buffered saline (vehicle), or compounds as listed in Table 19 dissolved in vehicle (dorsal, subcutaneous administration). Treatment was continued for 26 days at the doses and on the schedule shown in the Table 19 below. Polymer as referred to in this example refers to poly[HPMA-co-MA-GFLG-N-(6-aminohexyl)acetamide, a polymer which does not contain fumagillol.

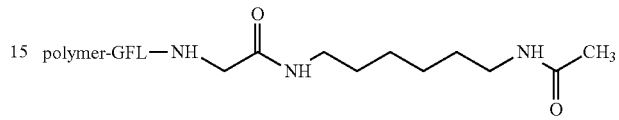

Compound cis-16 is Compound 16 where the 1,4-diaminocyclohexane is in the cis configuration rather than the trans configuration as depicted for Compound 16.

Compound aa is the reaction product of a 2 KDa MW methoxyterminated PEG amine and p-nitrophenyl fumagill-6-yl carbonate:

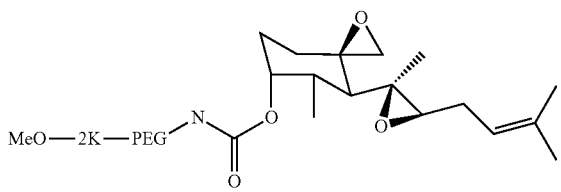

Compound bb is:

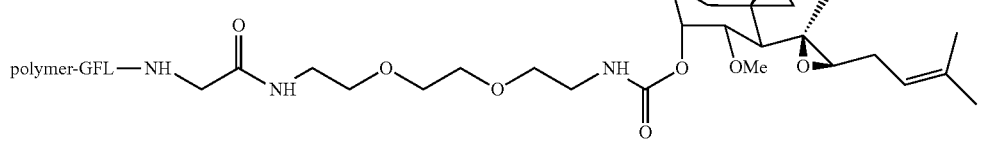

The synthesis of poly[HPMA-co-MA-GFLG-NH-2-[(2-(2-aminoethoxy)ethoxy)ethyl]carbamoylfumagillol] is described in WO/2011/150022, which is included by reference in its entirety.

TABLE 19

Body weight versus time in a DIO mouse model

| Group | Dose (q4d) mg/kg | Schdedule | Group Avg. BW (g) by Study Day | | | | | BW change vs. vehicle |
| --- | --- | --- | --- | --- | --- | --- | --- | --- |
|  |  |  | 1 | 7 | 15 | 21 | 26 |  |
| Vehicle | 0 | q4d | 47.0 | 45.0 | 45.8 | 46.1 | 46.1 | 0.0% |
| Compound 16 | 2 | q4d | 47.0 | 43.4 | 43.2 | 42.0 | 41.7 | −9.6% |
| Compound 16 q8d | 12 | q8d | 47.0 | 41.3 | 38.3 | 36.2 | 38.0 | −17.5% |
| Compound 32 | 2 | q4d | 47.0 | 42.0 | 40.6 | 41.6 | 40.5 | −12.1% |
| Compound 48 | 2 | q4d | 47.0 | 44.3 | 43.8 | 42.9 | 43.6 | −5.5% |
| Polymer | 12 | q4d | 47.0 | 44.8 | 46.1 | 46.3 | 46.5 | 0.8% |
| Compound cis-16 | 2 | q4d | 47.0 | 42.7 | 42.6 | 40.9 | 40.6 | −12.0% |

TABLE 19-continued

Body weight versus time in a DIO mouse model

| Group | Dose (q4d) mg/kg | Schdedule | Group Avg. BW (g) by Study Day 1 | 7 | 15 | 21 | 26 | BW change vs. vehicle |
|---|---|---|---|---|---|---|---|---|
| Compound aa | 2 | q4d | 47.0 | 44.3 | 45.2 | 45.4 | 45.8 | −0.8% |
| Compound bb | 2 | q4d | 47.0 | 43.6 | 43.9 | 42.2 | 42.5 | −7.8% |

What is claimed is:

1. A method for lowering or decreasing blood glucose levels in a subject in need thereof, comprising administering at least one compound, or a pharmaceutically acceptable salt thereof, selected from the group consisting of

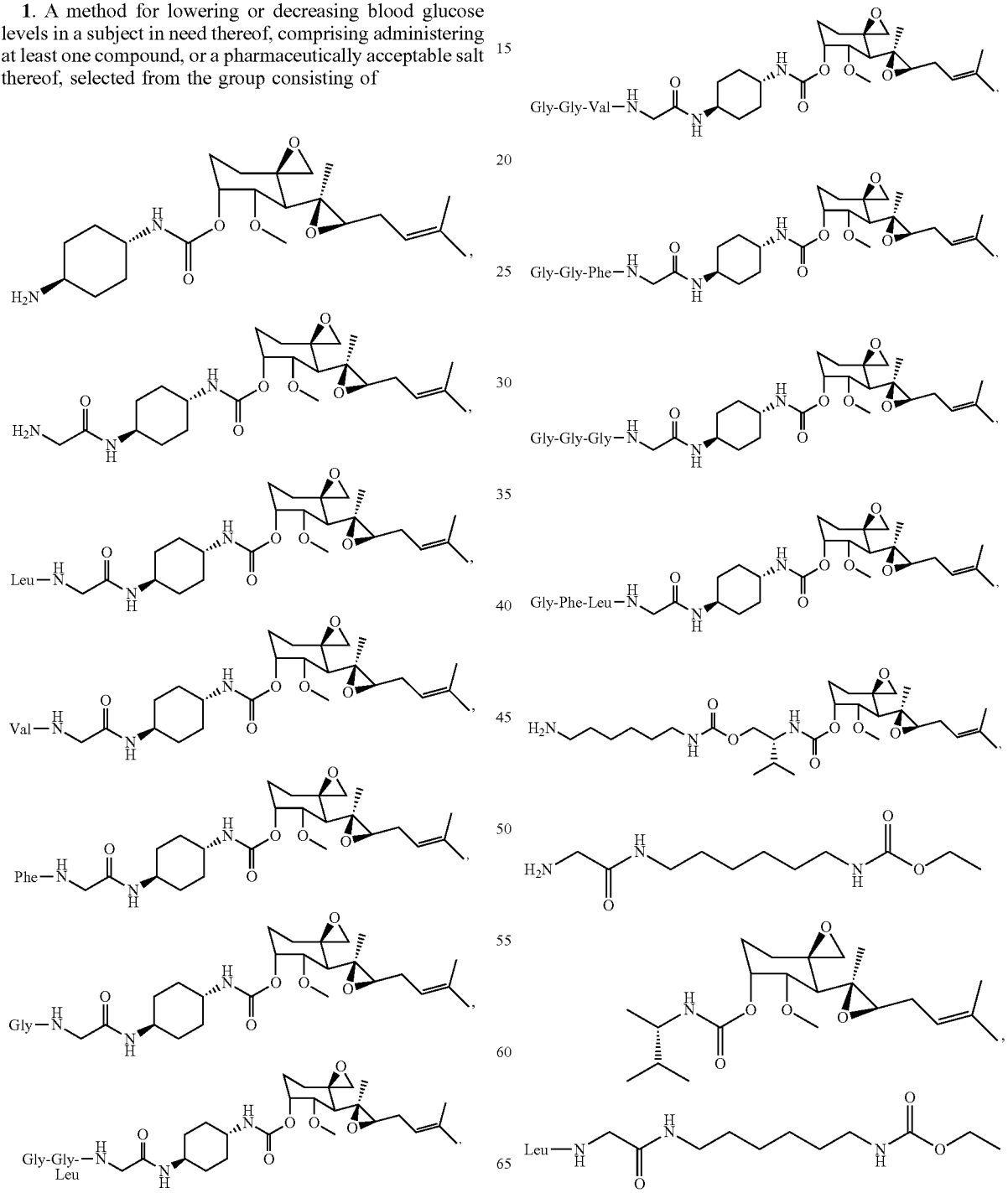

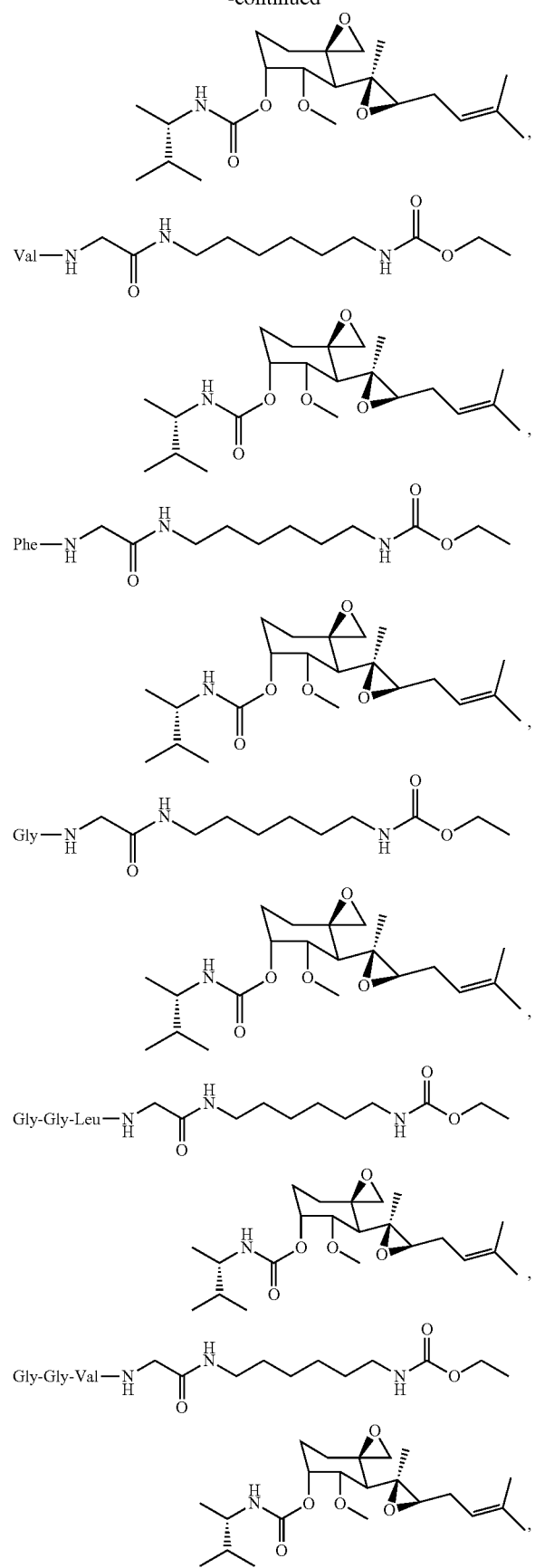
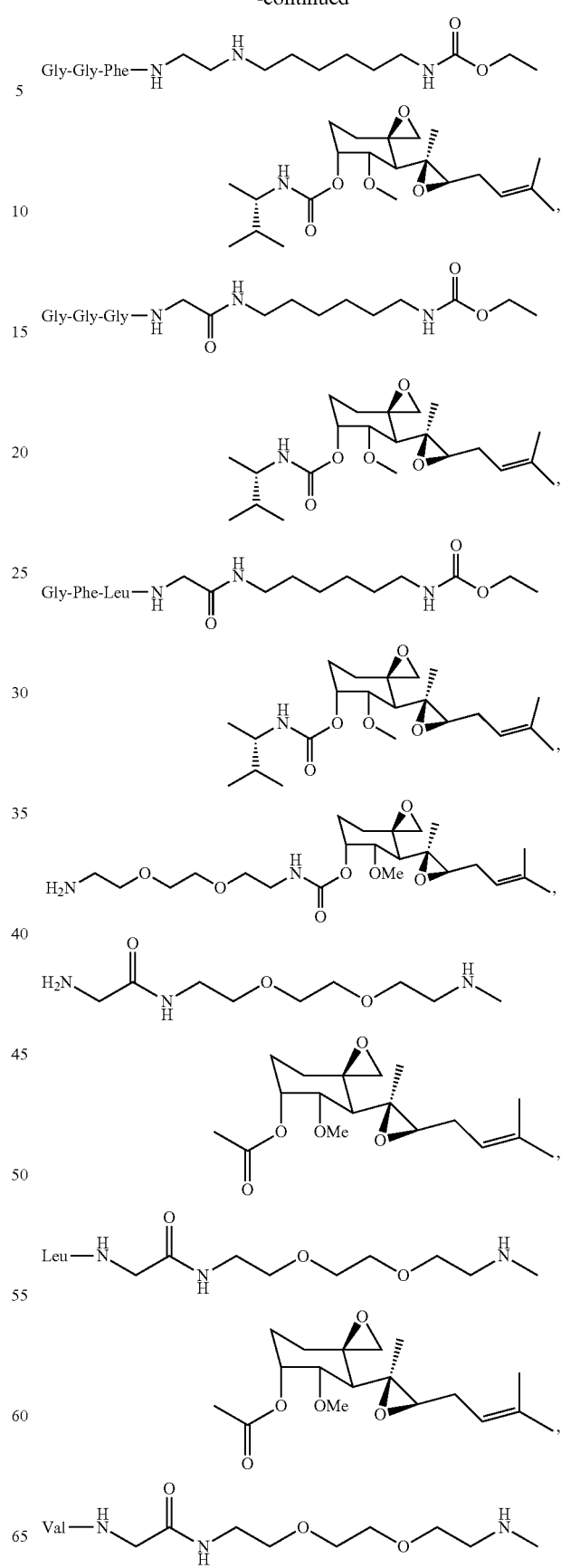

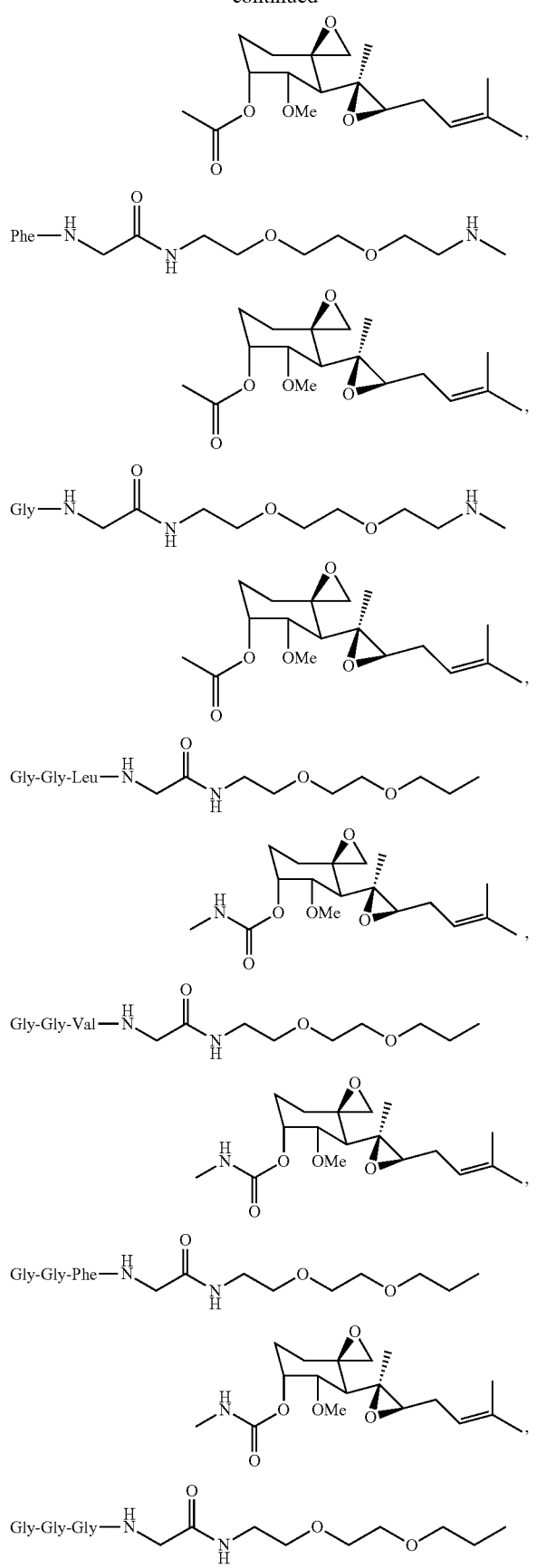

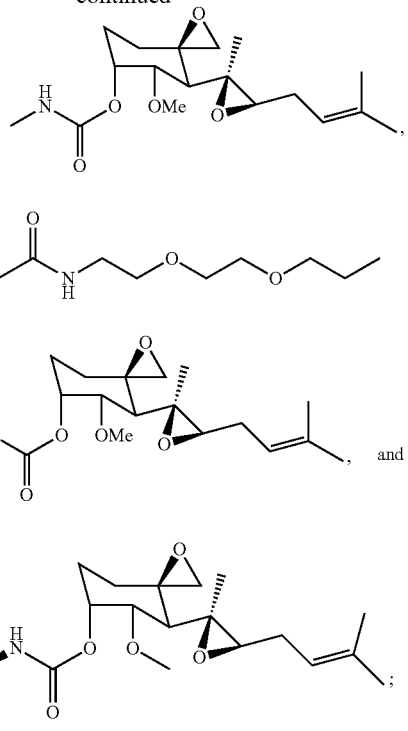

and

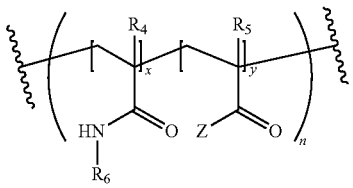

in a therapeutically effective amount to the subject.

2. A method for lowering or decreasing blood glucose levels in a subject in need thereof comprising administering at least one compound, or a pharmaceutically acceptable salt thereof, of the Formula wherein, independently for each occurrence, $R_4$ is H or $C_1$-$C_6$ alkyl;
$R_5$ is H or $C_1$-$C_6$ alkyl;
$R_6$ is $C_2$-$C_6$ hydroxyalkyl;
Z is —NH-$AA_1$-$AA_2$-$AA_3$-$AA_4$-$AA_5$-$AA_6$-C(O)-Q-X-Y—C(O)—W;
$AA_1$ is glycine, alanine, or $H_2N(CH_2)_mCO_2H$, wherein m is 2, 3, 4 or 5;
$AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

$AA_5$ is a bond, or glycine, valine, tyrosine, tryptophan, phenylalanine, methionine, leucine, isoleucine, or asparagine;

$AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5;

Q is NR, O, or S;

X is $M-(C(R)_2)_p-M-J-M-(C(R)_2)_p-M-V$;

M is a bond, or C(O);

J is a bond, or $((CH_2)_qQ)_r$, $C_5$-$C_8$ cycloalkyl, aryl, heteroaryl, NR, O, or S;

Y is NR, O, or S;

R is H or alkyl;

V is a bond or

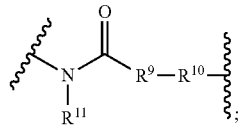

$R^9$ is alkyl, aryl, aralkyl, or a bond; or $R^9$ taken together with Y forms a heterocyclic ring;

$R^{10}$ is amido or a bond;

$R^{11}$ is H or alkyl;

W is a methionine aminopeptidase-2 inhibitor moiety according to the following structure:

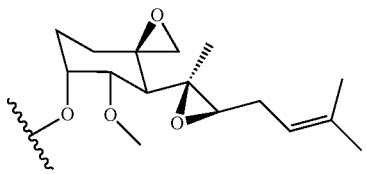

x is in the range of 1 to about 450;
y is in the range of 1 to about 30;
n is in the range of 1 to about 50;
p is 0 to 20;
q is 2 or 3; and
r is 1, 2, 3, 4, 5, or 6;
in a therapeutically effective amount to the subject.

3. The method of claim 2, wherein $R_4$ is methyl.

4. The method of claim 2, wherein $R_5$ is methyl.

5. The method of claim 2, wherein $R_6$ is 2-hydroxypropyl.

6. The method of claim 2, wherein Z is —NH-$AA_6$-C(O)-Q-X-Y—C(O)—W.

7. The method of claim 6, wherein $AA_6$ is glycine.

8. The method of claim 2, wherein Z is —NH-$AA_5$-$AA_6$-C(O)-Q-X-Y—C(O)—W.

9. The method of claim 8, wherein $AA_5$ is leucine and $AA_6$ is glycine.

10. The method of claim 8, wherein $AA_5$ is valine and $AA_6$ is glycine.

11. The method of claim 8, wherein $AA_5$ is phenylalanine and $AA_6$ is glycine.

12. The method of claim 8, wherein $AA_5$ is glycine and $AA_6$ is glycine.

13. The method of claim 2, wherein Z is —NH-$AA_3$-$AA_4$-$AA_5$-$AA_6$-C(O)-Q -X-Y—C(O)—W.

14. The method of claim 13, wherein $AA_5$ is leucine and each of $AA_3$, $AA_4$, or $AA_6$ is glycine.

15. The method of claim 13, wherein $AA_5$ is valine and each of $AA_3$, $AA_4$, or $AA_6$ is glycine.

16. The method of claim 13, wherein $AA_5$ is phenylalanine and each of $AA_3$, $AA_4$, or $AA_6$ is glycine.

17. The method of claim 13, wherein $AA_3$ is glycine, $AA_4$ is phenylalanine, $AA_5$ is leucine and $AA_6$ is glycine.

18. The method of claim 13, wherein each of $AA_3$, $AA_4$, $AA_5$ and $AA_6$ is glycine.

19. The method of claim 2, wherein -Q-X-Y is

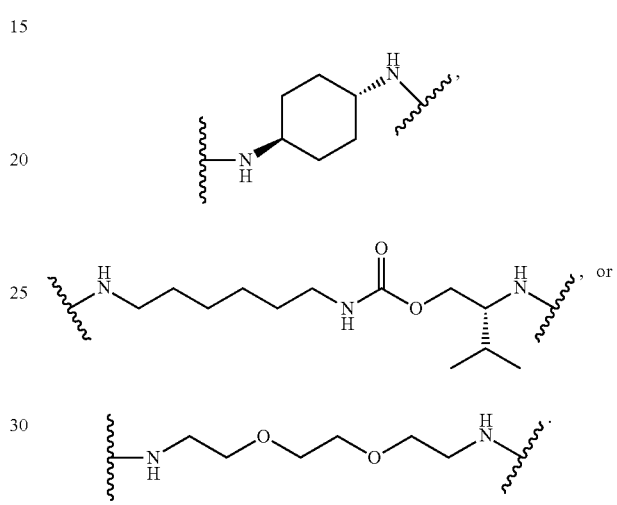

20. The method of claim 2, wherein the ratio of x to y is in the range of about 20:1 to about 4:1.

21. The method of claim 2, wherein the ratio of x to y is about 11:1.

22. The method of claim 2, wherein the subject has a BMI of 25 kg/m$^2$ to 29.9 kg/m$^2$.

23. The method of claim 2, wherein the subject has a BMI of 30 kg/m$^2$ or greater.

24. The method of claim 2, wherein the subject has a BMI of 35 kg/m$^2$ or greater.

25. The method of claim 2, wherein the subject has a BMI of 40 kg/m$^2$ or greater.

26. The method of claim 2, wherein the subject has at least one disorder selected from the group consisting of diabetes, non-insulin dependent diabetes mellitus-type II, impaired glucose tolerance, impaired fasting glucose, elevated plasma insulin concentrations, insulin resistance syndrome, hyperlipidemia, dyslipidemia, hypertension, hyperuricacidemia, gout, coronary artery disease, cardiac disease, myocardial infarction, angina pectoris, sleep apnea, obstructive sleep apnea, Pickwickian syndrome, fatty liver, cerebral infarction, stroke, cerebral thrombosis, respiratory complications, cholelithiasis, gallbladder disease, kidney disease, gastroesophageal reflux, stress urinary incontinence, arteriosclerosis, heart disease, abnormal heart rhythms, heart arrhythmias, transient ischemic attack, orthopedic disorders, osteoarthritis, arthritis deformans, lumbodynia, emmeniopathy, endocrinopathies, hormonal imbalances and infertility.

27. The method of claim 2, further comprising administering a second active agent.

28. The method of claim 2, further comprising decreasing body weight in said subject, wherein said body weight is decreased from about 1% to about 50%.

29. The method of claim 28, wherein decreasing body weight comprises decreasing body fat in said subject.

30. The method of claim 29, comprising decreasing body fat while substantially maintaining muscle mass in said subject.

31. The method of claim 28, wherein decreasing body weight comprises decreasing adipocytes in said subject.

32. The method of claim 28, wherein decreasing body weight comprises decreasing food intake in said subject.

33. The method of claim 2, wherein said subject does not have cancer or a hyper-proliferative disorder.

34. The method of claim 2, wherein said therapeutically effective amount is from about 0.0001 mg/kg to about 5 mg/kg of body weight per day.

35. The method of claim 2, wherein said therapeutically effective amount is from or about 0.001 to about 1 mg/kg of body weight per day.

36. The method of claim 2, wherein said compound is administered from about 1 to about 5 times per week.

37. The method of claim 2, wherein said compound is administered in a q4d dosing schedule.

38. The method of claim 2, wherein said compound is administered in a q7d dosing schedule.

39. The method of claim 2, wherein said compound is administered once every two weeks.

40. The method of claim 2, wherein said subject is treated for at least about six months.

41. The method of claim 2, wherein said subject is treated for at least about two years.

42. The method of claim 2, wherein said compound is administered parenterally.

43. The method of claim 2, wherein said compound is administered subcutaneously.

44. The method of claim 2, wherein said compound is provided as a pharmaceutical composition comprising said compound and a pharmaceutically acceptable carrier.

45. The method of claim 2, wherein Z is represented by:

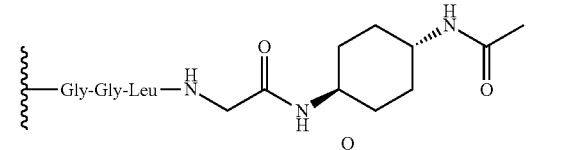

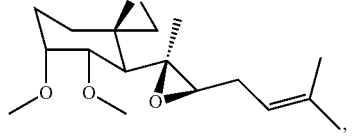

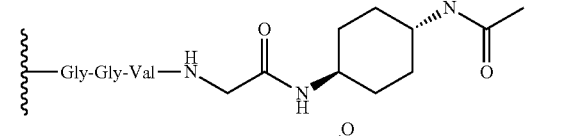

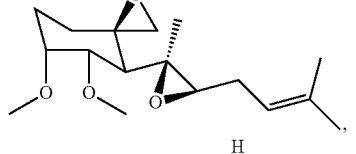

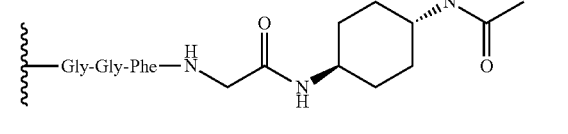

-continued

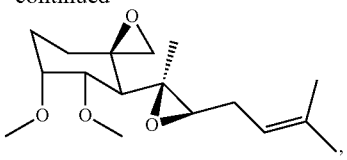

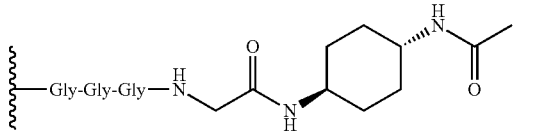

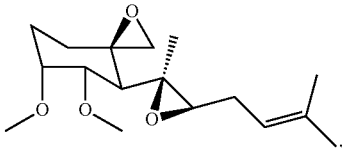

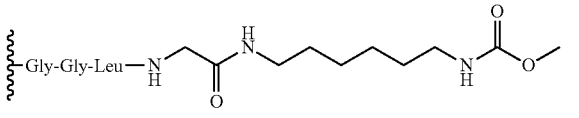

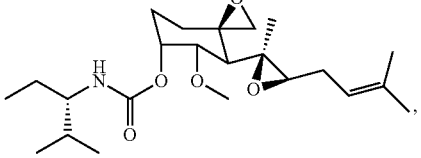

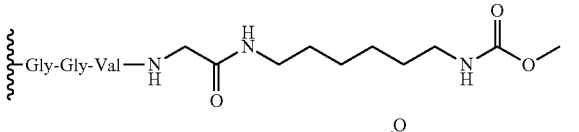

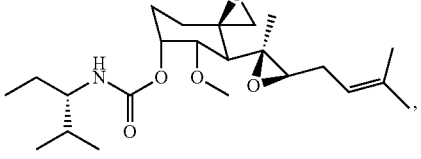

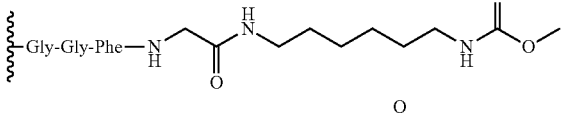

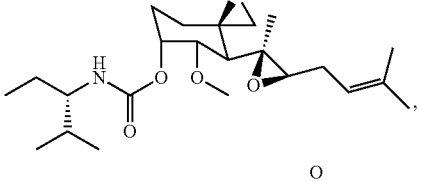

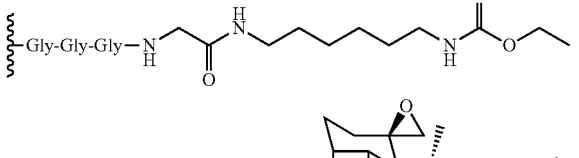

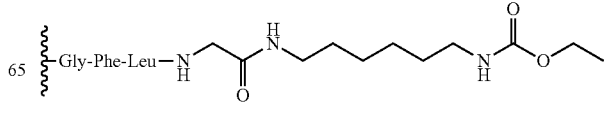

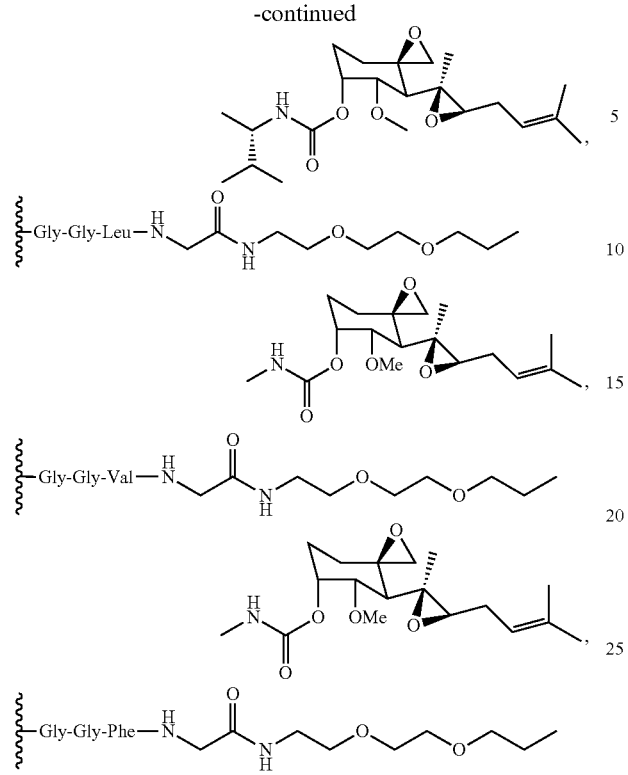
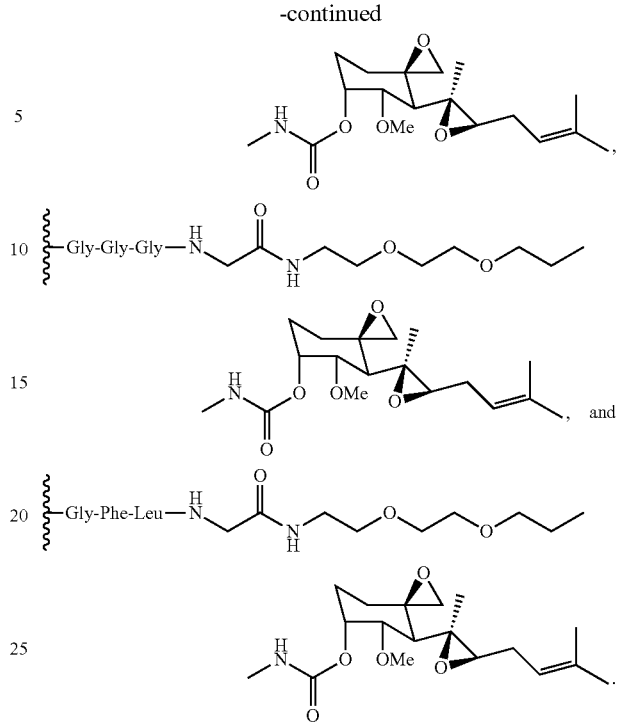
46. The method of claim 2, wherein Z is represented by
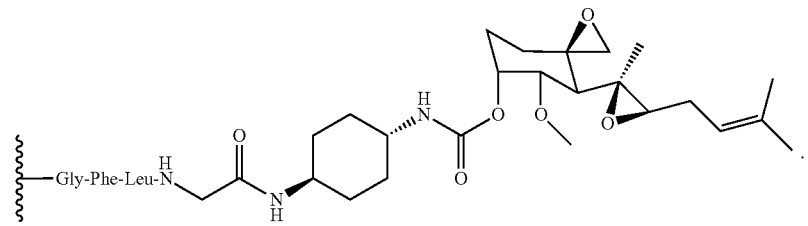
47. The method of claim 2, wherein the compound has a molecular weight of less than about 60 kDa.
* * * * *